United States Patent
Unger et al.

(10) Patent No.: US 6,443,898 B1
(45) Date of Patent: Sep. 3, 2002

(54) THERAPEUTIC DELIVERY SYSTEMS

(75) Inventors: Evan C. Unger; Thomas A. Fritz; Terry Matsunaga; VaradaRajan Ramaswami; David Yellowhair; Guanli Wu, all of Tucson, AZ (US)

(73) Assignee: Imarx Pharmaceutical Corp., Roy, UT (US)

( * ) Notice: Subject to any disclaimer, the term of this patent is extended or adjusted under 35 U.S.C. 154(b) by 0 days.

(21) Appl. No.: 08/485,998

(22) Filed: Jun. 7, 1995

Related U.S. Application Data

(60) Division of application No. 08/160,232, filed on Nov. 30, 1993, now Pat. No. 5,542,935, which is a continuation-in-part of application No. 08/159,687, filed on Nov. 30, 1993, now Pat. No. 5,585,112, which is a continuation-in-part of application No. 08/159,674, filed on Nov. 30, 1993, now abandoned, which is a continuation-in-part of application No. 08/076,250, filed on Jun. 11, 1993, now Pat. No. 5,580,575, which is a continuation-in-part of application No. 07/716,899, filed on Jun. 18, 1991, now abandoned, which is a continuation-in-part of application No. 07/717,084, filed on Jun. 18, 1991, now Pat. No. 5,228,446, which is a continuation-in-part of application No. 07/569,828, filed on Aug. 20, 1990, now Pat. No. 5,088,499, which is a continuation-in-part of application No. 07/455,707, filed on Dec. 22, 1989, now abandoned.

(51) Int. Cl.[7] .............................. A61B 8/00; A61K 9/127
(52) U.S. Cl. ....................... 600/458; 424/450; 424/9.51
(58) Field of Search ................................ 600/437, 439, 600/458; 424/9.5–9.52, 450

(56) References Cited

U.S. PATENT DOCUMENTS

| | | | |
|---|---|---|---|
| 3,015,128 A | 1/1962 | Sommerville et al. | 18/2.6 |
| 3,291,843 A | 12/1966 | Fritz et al. | 260/614 |
| 3,293,114 A | 12/1966 | Kenaga et al. | 162/168 |
| 3,479,811 A | 11/1969 | Walters | 57/153 |

(List continued on next page.)

FOREIGN PATENT DOCUMENTS

| | | |
|---|---|---|
| AU | 641363 | 3/1990 |
| AU | B-30351/89 | 3/1993 |
| DE | 25 21 003 | 8/1976 |
| DE | 3803972 | 8/1989 |
| EP | 0 052 575 | 5/1982 |
| EP | 0 107 559 | 5/1984 |
| EP | 0 077 752 B1 | 3/1986 |
| EP | 0 243 947 | 4/1987 |
| EP | 0 224 934 | 6/1987 |
| EP | 0 231 091 | 8/1987 |
| EP | 0 272 091 | 6/1988 |
| EP | 0 320 433 A2 | 12/1988 |

(List continued on next page.)

OTHER PUBLICATIONS

Feinstein, Steven B., "Myocardial Perfusion Imaging: Contrast Echocardiography Today and Tomorrow," *Journal of the American College of Cardiology*, 8(1):251–253 (1986).

Keller et al., "The Behavior of Sonicated Albumin Microbubbles Within the Microcirculation: A Basis for Their Use During Myocardial Contrast Echocardiography", *Circulation Res.*, 65(2):458–465 (1989).

Lincoff et al., "Perfluoro–n–butane: A Gas for the Maximum Duration Retinal Tamponade," *Arch Ophthalmology*, 101:460–462 (1983).

(List continued on next page.)

*Primary Examiner*—Francis J. Jaworsid
(74) *Attorney, Agent, or Firm*—Woodcock Washburn Kurtz Mackiewicz & Norris LLP

(57) ABSTRACT

Therapeutic delivery systems comprising gaseous precursor-filled microspheres comprising a therapeutic are described. Methods for employing such microspheres in therapeutic delivery applications are also provided. Therapeutic delivery systems comprising gaseous precursor-filled liposomes having encapsulated therein a contrast agent or drug are preferred. Methods of and apparatus for preparing such liposomes and methods for employing such liposomes in therapeutic delivery applications are also disclosed.

96 Claims, 23 Drawing Sheets

U.S. PATENT DOCUMENTS

| | | |
|---|---|---|
| 3,488,714 A | 1/1970 | Walters et al. ............... 161/161 |
| 3,532,500 A | 10/1970 | Priest et al. .................... 96/91 |
| 3,557,294 A | 1/1971 | Dear et al. .................. 424/342 |
| 3,594,326 A | 7/1971 | Himmel et al. ............. 252/316 |
| 3,615,972 A | 10/1971 | Morehouse et al. .......... 156/79 |
| 3,650,831 A | 3/1972 | Jungermann et al. ......... 134/27 |
| 3,732,172 A | 5/1973 | Herbig et al. ............... 252/316 |
| 3,873,564 A | 3/1975 | Schneider et al. ....... 260/309.6 |
| 3,945,956 A | 3/1976 | Garner ................... 260/2.5 B |
| 3,960,583 A | 6/1976 | Netting et al. .............. 106/122 |
| 3,968,203 A | 7/1976 | Spitzer et al. ................ 424/47 |
| 4,027,007 A | 5/1977 | Messina ...................... 424/46 |
| 4,089,801 A | 5/1978 | Schneider ................... 252/316 |
| 4,108,806 A | 8/1978 | Cohrs et al. ................. 521/54 |
| 4,138,383 A | 2/1979 | Rembaum et al. ..... 260/29.7 H |
| 4,162,282 A | 7/1979 | Fulwyler et al. ................ 264/9 |
| 4,179,546 A | 12/1979 | Garner et al. ................. 521/56 |
| 4,192,859 A | 3/1980 | Mackaness et al. ............ 424/5 |
| 4,224,179 A | 9/1980 | Schneider ................... 252/316 |
| 4,229,360 A | 10/1980 | Schneider et al. .......... 260/403 |
| 4,265,251 A | 5/1981 | Tickner ....................... 128/660 |
| 4,276,885 A | 7/1981 | Tickner et al. .............. 128/660 |
| 4,310,505 A | 1/1982 | Baldeschwieler et al. ....... 424/1 |
| 4,310,506 A | 1/1982 | Baldeschwieler et al. ....... 424/1 |
| 4,315,514 A | 2/1982 | Drewes et al. .............. 128/653 |
| 4,331,654 A | 5/1982 | Morris ......................... 424/38 |
| 4,342,826 A | 8/1982 | Cole ............................... 435/7 |
| 4,344,929 A | 8/1982 | Bonsen et al. ................. 424/15 |
| 4,420,442 A | 12/1983 | Sands ........................... 264/13 |
| 4,421,562 A | 12/1983 | Sands et al. ................. 106/75 |
| 4,426,330 A | 1/1984 | Sears ......................... 260/403 |
| 4,427,649 A | 1/1984 | Dingle et al. ................. 424/38 |
| 4,428,924 A | 1/1984 | Millington ...................... 424/4 |
| 4,442,843 A | 4/1984 | Rasor et al. ................ 128/660 |
| 4,450,629 A | 5/1984 | Sands et al. ................ 428/402 |
| 4,466,442 A | 8/1984 | Hilmann et al. ............ 128/653 |
| 4,530,360 A | 7/1985 | Duarte ................... 128/419 F |
| 4,533,254 A | 8/1985 | Cook et al. ................. 366/176 |
| 4,534,899 A | 8/1985 | Sears ......................... 260/403 |
| 4,544,545 A | 10/1985 | Ryan et al. .................. 424/1.1 |
| 4,549,892 A | 10/1985 | Baker et al. ................. 65/21.4 |
| 4,569,836 A | 2/1986 | Gordon .......................... 424/1 |
| 4,572,203 A | 2/1986 | Feinstein ................... 128/661 |
| 4,586,512 A | 5/1986 | Do-huu et al. .............. 128/660 |
| 4,603,044 A | 7/1986 | Geho et al. ..................... 424/9 |
| 4,615,879 A | 10/1986 | Runge et al. ................... 424/9 |
| 4,620,546 A | 11/1986 | Aida et al. .................. 128/660 |
| 4,646,756 A | 3/1987 | Watmough et al. ......... 128/804 |
| 4,657,756 A | 4/1987 | Rasor et al. ..................... 424/9 |
| 4,658,828 A | 4/1987 | Dory ........................... 128/660 |
| 4,663,161 A | 5/1987 | Mannino et al. ............. 424/89 |
| 4,675,310 A | 6/1987 | Chapman et al. .............. 514/6 |
| 4,681,119 A | 7/1987 | Rasor et al. ................ 128/660 |
| 4,684,479 A | 8/1987 | D'Arrigo .................... 252/307 |
| 4,689,986 A | 9/1987 | Carson et al. ................. 73/19 |
| 4,693,999 A | 9/1987 | Axelsson et al. ............ 514/174 |
| 4,718,433 A | 1/1988 | Feinstein ................... 128/660 |
| 4,728,575 A | 3/1988 | Gamble et al. .......... 428/402.2 |
| 4,728,578 A | 3/1988 | Higgins et al. ............. 428/462 |
| 4,731,239 A | 3/1988 | Gordon .......................... 424/9 |
| 4,737,323 A | 4/1988 | Martin et al. ................ 264/4.3 |
| 4,774,958 A | 10/1988 | Feinstein ............... 128/660.01 |
| 4,775,522 A | 10/1988 | Clark, Jr. ........................ 424/9 |
| 4,776,991 A | 10/1988 | Farmer et al. .............. 264/4.3 |
| 4,781,871 A | 11/1988 | West, III et al. ............. 264/4.3 |
| 4,789,501 A | 12/1988 | Day et al. ................... 252/645 |
| 4,790,891 A | 12/1988 | Halliday et al. ............... 149/2 |
| 4,822,534 A | 4/1989 | Lencki et al. ................ 264/4.3 |
| 4,830,858 A | 5/1989 | Payne et al. ................ 424/450 |
| 4,834,964 A | 5/1989 | Rosen ............................ 424/9 |
| 4,844,882 A | 7/1989 | Widder et al. ................. 424/9 |
| 4,863,717 A | 9/1989 | Keana ............................ 424/9 |
| 4,865,836 A | 9/1989 | Long, Jr. ........................ 424/5 |
| 4,877,561 A | 10/1989 | Iga et al. ..................... 264/4.3 |
| 4,893,624 A | 1/1990 | Lele ........................... 128/399 |
| 4,895,719 A | 1/1990 | Radhakrishnan ............. 424/45 |
| 4,898,734 A | 2/1990 | Mathiowitz et al. ........ 424/426 |
| 4,900,540 A | 2/1990 | Ryan et al. ..................... 424/9 |
| 4,918,065 A | 4/1990 | Stindl et al. ................. 514/179 |
| 4,919,895 A | 4/1990 | Heldebrant et al. ......... 422/129 |
| 4,921,706 A | 5/1990 | Roberts et al. ............. 424/450 |
| 4,927,623 A | 5/1990 | Long, Jr. ........................ 424/5 |
| 4,933,121 A | 6/1990 | Law et al. ................... 264/4.3 |
| 4,938,947 A | 7/1990 | Nicolau et al. .............. 424/1.1 |
| 4,957,656 A | 9/1990 | Cerny et al. ................ 252/311 |
| 4,972,002 A | 11/1990 | Volkert .......................... 521/120 |
| 4,981,692 A | 1/1991 | Popescu et al. ............. 424/422 |
| 4,984,573 A | 1/1991 | Leunbach ................... 128/653 |
| 4,985,550 A | 1/1991 | Charpiot et al. ........... 536/18.4 |
| 4,987,154 A | 1/1991 | Long, Jr. ..................... 514/772 |
| 4,993,415 A | 2/1991 | Long ..................... 128/653 A |
| 4,996,041 A | 2/1991 | Arai et al. ...................... 424/9 |
| 5,000,960 A | 3/1991 | Wallach ...................... 424/450 |
| 5,004,611 A | 4/1991 | Leigh .......................... 424/450 |
| 5,008,050 A | 4/1991 | Cullis et al. ................. 264/4.3 |
| 5,008,109 A | 4/1991 | Tin .............................. 424/422 |
| 5,013,556 A | 5/1991 | Woodle et al. .............. 424/450 |
| 5,019,370 A | 5/1991 | Jay et al. ........................ 424/4 |
| 5,045,304 A | 9/1991 | Schneider et al. ............. 424/9 |
| 5,049,388 A | 9/1991 | Knight et al. ............... 424/450 |
| 4,229,360 C1 | 11/1991 | Schneider et al. .......... 260/403 |
| 5,078,994 A | 1/1992 | Nair et al. ................... 424/501 |
| 5,088,499 A | 2/1992 | Unger ..................... 128/662.2 |
| 5,107,842 A | 4/1992 | Levene et al. ......... 128/662.02 |
| 5,114,703 A | 5/1992 | Wolf et al. ..................... 424/5 |
| 5,123,414 A | 6/1992 | Unger .......................... 128/654 |
| 5,135,000 A | 8/1992 | Akselrod et al. ....... 128/662.02 |
| 5,137,923 A | 8/1992 | Erbel et al. .................. 521/56 |
| 5,141,738 A | 8/1992 | Rasor et al. .................... 424/2 |
| 5,147,631 A | 9/1992 | Glajch et al. ................... 424/9 |
| 5,149,319 A | 9/1992 | Unger .......................... 604/22 |
| 5,171,755 A | 12/1992 | Kaufman ................... 514/759 |
| 5,186,922 A | 2/1993 | Shell et al. .................. 128/654 |
| 5,190,766 A | 3/1993 | Ishihara ...................... 424/489 |
| 5,190,982 A | 3/1993 | Erbel et al. .................. 521/56 |
| 5,192,549 A | 3/1993 | Barenolz et al. ............ 424/450 |
| 5,194,266 A | 3/1993 | Abra et al. .................. 424/450 |
| 5,195,520 A | 3/1993 | Schlief et al. .......... 128/660.02 |
| 5,196,183 A | 3/1993 | Yudelson et al. .............. 424/9 |
| 5,196,348 A | 3/1993 | Schweighardt et al. ...... 436/173 |
| 5,198,225 A | 3/1993 | Meybeck et al. ............ 424/450 |
| 5,205,287 A | 4/1993 | Erbel et al. ................. 128/632 |
| 5,205,290 A | 4/1993 | Unger ..................... 128/653.4 |
| 5,209,720 A | 5/1993 | Unger .......................... 604/22 |
| 5,213,804 A | 5/1993 | Martin et al. ................ 424/450 |
| 5,215,680 A | 6/1993 | D'Arrigo .................... 252/307 |
| 5,219,538 A | 6/1993 | Henderson et al. ...... 428/402.2 |
| 5,228,446 A | 7/1993 | Unger et al. ............ 128/662.02 |
| 5,230,882 A | 7/1993 | Unger ............................ 424/9 |
| 5,247,935 A | 9/1993 | Cline et al. .............. 128/653.2 |
| 5,271,928 A | 12/1993 | Schneider et al. ............. 424/9 |
| 5,281,408 A | 1/1994 | Unger ............................ 424/4 |
| 5,305,757 A | 4/1994 | Unger et al. ........... 128/662.02 |
| 5,310,540 A | 5/1994 | Giddey et al. .................. 424/9 |
| 5,315,997 A | 5/1994 | Widder et al. ............ 128/653.3 |
| 5,315,998 A | 5/1994 | Tachibana et al. ...... 128/660.01 |
| 5,316,771 A | 5/1994 | Barenholz et al. .......... 424/450 |
| 5,334,381 A | 8/1994 | Unger ............................ 424/9 |
| 5,339,814 A | 8/1994 | Lasker ..................... 128/653.4 |
| 5,344,930 A | 9/1994 | Reiss et al. .................... 544/84 |
| 5,350,571 A | 9/1994 | Kaufman et al. ............... 424/9 |

| | | | | | | | |
|---|---|---|---|---|---|---|---|
| 5,352,435 A | 10/1994 | Unger | 424/9 | 5,686,060 A | 11/1997 | Schneider et al. | 424/9.52 |
| 5,354,549 A | 10/1994 | Klaveness et al. | 424/3 | 5,686,102 A | 11/1997 | Gross et al. | 424/450 |
| 5,358,702 A | 10/1994 | Unger | 424/9 | 5,701,899 A | 12/1997 | Porter | 428/662.02 |
| 5,362,477 A | 11/1994 | Moore et al. | 424/9 | 5,707,352 A | 1/1998 | Sekins et al. | 604/56 |
| 5,362,478 A | 11/1994 | Desai et al. | 424/9 | 5,707,606 A | 1/1998 | Quay | 424/9.52 |
| 5,380,519 A | 1/1995 | Schneider et al. | 424/9 | 5,707,607 A | 1/1998 | Quay | 424/9.52 |
| 5,393,524 A | 2/1995 | Quay | 424/9 | 5,711,933 A | 1/1998 | Bichon et al. | 424/9.52 |
| 5,409,688 A | 4/1995 | Quay | 424/9 | 5,716,597 A | 2/1998 | Lohramann et al. | 424/9.5 |
| 5,410,516 A | 4/1995 | Uhlendorf et al. | 367/7 | 5,732,707 A | 3/1998 | Widder et al. | 128/661.08 |
| 5,413,774 A | 5/1995 | Schneider et al. | 424/9.51 | 5,733,527 A | 3/1998 | Schutt | 424/9.52 |
| 5,425,366 A | 6/1995 | Reinhardt et al. | 128/662.02 | 5,736,121 A | 4/1998 | Unger | 424/9.4 |
| 5,433,204 A | 7/1995 | Olson | 128/661.08 | 5,740,807 A | 4/1998 | Porter | 128/662.02 |
| 5,445,813 A | 8/1995 | Schneider et al. | 424/9.51 | 5,804,162 A | 9/1998 | Kabalnov et al. | 424/9.51 |
| 5,456,900 A | 10/1995 | Unger | 424/9.4 | 5,840,023 A | 11/1998 | Oraevsky et al. | 600/407 |
| 5,460,800 A | 10/1995 | Walters | 424/9.6 | 5,855,865 A | 1/1999 | Lambert e al. | 424/9.52 |
| 5,469,854 A | 11/1995 | Unger et al. | 128/662.02 | 5,874,062 A | 2/1999 | Unger | 424/9.4 |
| 5,470,582 A | 11/1995 | Supersaxo et al. | 424/489 | 5,897,851 A | 4/1999 | Quay et al. | 424/9.52 |
| 5,485,839 A | 1/1996 | Aida et al. | 128/653.1 | 5,976,501 A | 11/1999 | Jablonski | 424/9.52 |
| 5,487,390 A | 1/1996 | Cohen et al. | 128/662.02 | | | | |
| 5,496,535 A | 3/1996 | Kirkland | 424/9.37 | | | | |

FOREIGN PATENT DOCUMENTS

| | | |
|---|---|---|
| EP | 0 324 938 | 7/1989 |
| EP | 0 338 971 | 10/1989 |
| EP | 357163 A1 | 3/1990 |
| EP | 0 359 246 | 3/1990 |
| EP | 0 361 894 | 4/1990 |
| EP | 0 216 730 | 1/1991 |
| EP | 0 467 031 A2 | 5/1991 |
| EP | 441468 A2 | 8/1991 |
| EP | 0 357 164 B1 | 10/1991 |
| EP | 0 458 745 A1 | 11/1991 |
| EP | 0 314 764 B1 | 9/1992 |
| EP | 0 554 213 A1 | 8/1993 |
| EP | 0 586 875 | 3/1994 |
| EP | 0 614 656 A1 | 9/1994 |
| EP | 0 727 225 A2 | 8/1996 |
| FR | WO 91/00086 | 1/1991 |
| FR | 2 700 952 | 8/1994 |
| GB | 1044680 | 10/1966 |
| GB | 2193095 A | 2/1988 |
| JP | 62 286534 | 12/1987 |
| JP | SHO 63-60943 | 3/1988 |
| WO | WO 80/02365 | 11/1980 |
| WO | WO 82/01642 | 5/1982 |
| WO | 85/01161 | 3/1985 |
| WO | WO 85/02772 | 7/1985 |
| WO | WO 86/00238 | 1/1986 |
| WO | WO 86/01103 | 2/1986 |
| WO | WO 89/05040 | 6/1989 |
| WO | WO 90/01952 | 3/1990 |
| WO | WO 90/04384 | 5/1990 |
| WO | WO 90/04943 | 5/1990 |
| WO | WO 91/03267 | 3/1991 |
| WO | WO 91/09629 | 7/1991 |
| WO | WO 91/12823 | 9/1991 |
| WO | WO 91/15244 | 10/1991 |
| WO | WO 92/10166 | 6/1992 |
| WO | WO 92/11873 | 7/1992 |
| WO | WO 92/15284 | 9/1992 |
| WO | WO 92/17212 | 10/1992 |
| WO | WO 92/17213 | 10/1992 |
| WO | WO 92/17436 | 10/1992 |
| WO | WO 92/17514 | 10/1992 |
| WO | WO 92/21382 | 10/1992 |
| WO | WO 92/22247 | 12/1992 |
| WO | WO 92/22249 | 12/1992 |
| WO | WO 92/22298 | 12/1992 |
| WO | WO 93/00933 | 1/1993 |
| WO | WO 93/05819 | 1/1993 |
| WO | WO 93/06869 | 4/1993 |
| WO | WO 93/13809 | 7/1993 |
| WO | WO 93/17718 | 9/1993 |

| | | | |
|---|---|---|---|
| 5,498,421 A | 3/1996 | Grinstaff et al. | 424/450 |
| 5,501,863 A | 3/1996 | Rössling et al. | 424/489 |
| 5,502,094 A | 3/1996 | Moore et al. | 524/145 |
| 5,505,932 A | 4/1996 | Grinstaff et al. | 424/9.3 |
| 5,508,021 A | 4/1996 | Grinstaff et al. | 424/9.322 |
| 5,527,521 A | 6/1996 | Unger | 424/93 |
| 5,529,766 A | 6/1996 | Klaveness et al. | 424/9.52 |
| 5,531,980 A | 7/1996 | Schneider et al. | 424/9.52 |
| 5,536,489 A | 7/1996 | Lohrmann et al. | 424/9.52 |
| 5,536,490 A | 7/1996 | Klaveness et al. | 424/9.52 |
| 5,540,909 A | 7/1996 | Schutt | 424/9.52 |
| 5,542,935 A | 8/1996 | Unger et al. | 604/190 |
| 5,545,396 A | 8/1996 | Albert et al. | 424/93 |
| 5,547,656 A | 8/1996 | Unger | 424/9.4 |
| 5,552,133 A | 9/1996 | Lambert et al. | 424/9.52 |
| 5,552,155 A | 9/1996 | Bailey et al. | 424/450 |
| 5,556,372 A | 9/1996 | Talish et al. | 601/2 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |
| 5,558,853 A | 9/1996 | Quay | 424/9.5 |
| 5,558,854 A | 9/1996 | Quay | 424/9.52 |
| 5,558,855 A | 9/1996 | Quay | 424/9.5 |
| 5,558,856 A | 9/1996 | Klaveness et al. | 424/9.37 |
| 5,560,364 A | 10/1996 | Porter | 128/662.02 |
| 5,562,608 A | 10/1996 | Sekins et al. | 604/20 |
| 5,562,893 A | 10/1996 | Lohrmann | 424/9.52 |
| 5,565,215 A | 10/1996 | Gref et al. | 424/501 |
| 5,567,413 A | 10/1996 | Klaveness et al. | 424/9.51 |
| 5,567,414 A | 10/1996 | Schneider et al. | 424/9.52 |
| 5,567,765 A | 10/1996 | Moore et al. | 524/801 |
| 5,569,448 A | 10/1996 | Wong et al. | 424/9.45 |
| 5,569,449 A | 10/1996 | Klaveness et al. | 424/9.51 |
| 5,571,797 A | 11/1996 | Ohno et al. | 514/44 |
| 5,573,751 A | 11/1996 | Quay | 424/9.52 |
| 5,578,292 A | 11/1996 | Schneider et al. | 424/9.51 |
| 5,585,112 A | 12/1996 | Unger et al. | 424/450 |
| 5,593,680 A | 1/1997 | Bara et al. | 424/401 |
| 5,595,723 A | 1/1997 | Quay | 424/9.5 |
| 5,605,673 A | 2/1997 | Schutt et al. | 424/9.51 |
| 5,606,973 A | 3/1997 | Lambert et al. | 128/662.02 |
| 5,612,318 A | 3/1997 | Weichselbaum et al. | 514/44 |
| 5,614,169 A | 3/1997 | Klaveness et al. | 424/9.52 |
| 5,620,689 A | 4/1997 | Allen et al. | 424/178.1 |
| 5,626,833 A | 5/1997 | Schutt et al. | 424/9.52 |
| 5,639,443 A | 6/1997 | Schutt et al. | 424/9.52 |
| 5,643,553 A | 7/1997 | Schneider et al. | 424/9.52 |
| 5,648,095 A | 7/1997 | Illum et al. | 424/489 |
| 5,672,585 A | 9/1997 | Pierschbacher et al. | 514/11 |
| 5,676,928 A | 10/1997 | Klaveness et al. | 424/9.32 |
| 5,679,459 A | 10/1997 | Riess et al. | 428/402.2 |

| | | |
|---|---|---|
| WO | WO 93/20802 | 10/1993 |
| WO | WO 94/00110 | 1/1994 |
| WO | WO 94/06477 | 3/1994 |
| WO | WO 94/07539 | 4/1994 |
| WO | WO 94/09829 | 5/1994 |
| WO | WO 84/02909 | 8/1994 |
| WO | WO 94/16739 | 8/1994 |
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/32005 | 11/1995 |
| WO | WO 96/04018 | 2/1996 |
| WO | WO 96/09793 | 4/1996 |
| WO | WO 96/36286 | 11/1996 |
| WO | WO 96/40281 | 12/1996 |
| WO | WO 98/00172 | 1/1998 |

OTHER PUBLICATIONS

*Remington's Pharmaceutical Sciences,* John Hoover, managing ed., Mack Publishing Company, Easton, PA, pp. 295–298; 736; 1242–1244 (1975).

*Handbook of Pharmaceutical Excipients,* American Pharmaceutical Association, Washington, D.C. and The Pharmaceutical Society of Great Britain, London, England, pp. 181–183 (1986).

Barnhart et al., "Characteristics of Albunex™: Air–Filled Microspheres for Echocardiography Contrast Enhancement," *Investigative Radiology,* 25:S162–164.

Levene et al., "Characterization of Albunex™," *J. Acoust. Soc. Am.,* 87(Suppl.1):569–70.

Miller et al., "Physiochemical Approaches to the Mode of Action of General Anesthetics," *J. Amer. Soc. Anesthesiologists,* 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials,* 11:713–717 (1990).

Villaneuva et al., "Characterization of Spatial Patters of Flow Within the Reperfused Myocardium of Myocardial Contrast Echocardiography" *Circulation,* vol. 88, No. 6, pp. 2596–2606 (Dec. 1993).

Desir et al., "Assessment of regional myocardial perfusion with myocardial contrast echocardiography in a canine model of varying degrees of coronary stenosis", *Am. Heart J.,* Jan., 1994, 127(1), 56–63.

Sekins et al., "Lung Cancer Hyperthermia via Ultrasound and PFC Ligands", Published in *Proceedings of 5th International Symposium on Hyperthermic Oncology,* Kyoto, Japan, Aug. 29–Sep. 3, 1998, 3 pages.

Pietersen, "A New Warning System for Fires of Electrical Origin", CERN European Organization for Nuclear Research, Health and Safety Division, Mar., 1977, 1–5.

Nomura et al., "US Contrast Enhancement of Hepatic Tumor with Helium Gas Microbubbles: A Preliminary Report", *Jpn. J. Med. Ultrasonics,* 1991, 18(5), (Japanese with English language abstract).

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography,* 1988, 11(1), 36–46.

Regen et al., "Polymerized Phosphatidylcholine Vesicles. Synthesis and Characterization", *J. Am. Chem. Soc.,* 1982, 104(3), 191–195.

Wei et al., "Quantification of Myocardial Blood Flow with Ultrasound–Induced Destruction of Microbubbles Administered as a Constant Venous Infusion", *Circulation,* 1998, 97, 473–483.

Lejbkowicz et al., "The response of normal and malignant cells to ultrasound in vitro", Database BIOSIS, No. 1993:95122245 (abstract only).

Jackson et al., "Effect of ultrasound therapy on the repair of Achilles tendon injuries in rats", *Med. Sci. Sports Exercise,* 1991, 23(2), 171–176.

Maxwell, "Therapeutic Ultrasound: Its Effects on the Cellular and Molecular Mechanisms of Inflammation and Repair", *Physiotherapy,* 1992, 78(6), 421–426.

Tuncay et al., "Expression of Genes Associated with Tissue Remodeling Upon Ultrasound Perturbation in the Gingival Fibroblast", *J. Dental Res.,* 1996, 75, 143, (abstract only).

Wang et al., "Low Intensity Ultrasound Treatment Increases Strength in a Rat Femoral Fracture Model", *J. Orthopaedic Res.,* 1994, 12(1), 40–47.

Yang et al., "Exposure to Low–Intensity Ultrasound Increases Aggrecan Gene Expression in a Rat Femur Fracture Model", *J. Orthopaedic Res.,* 14(5), 802–809.

Young et al., "Effect of therapeutic ultrasound on the healing of full–thickness excised skin lesions", *Ultrasonics,* 1990, 28(3), 175–180.

Young et al., "The Effect of Therapeutic Ultrasound on Angiogenesis", *Ultrasound Med. Biol.,* 1990, 16(3), 261–269.

Chortkoff, B.S. et al., "Pharmacokinetics Do Not Explain the Absence of an Anesthetic Effect of Perfluoropropane or Perfluoropentane," *Anesth. Analg.,* 1994, 79, 234–237.

Sharma, S.K. et al., "Emulsification Methods For Perfluorochemicals," *Drug Develop. Indust. Pharm.,* 1988, 14(15–17), 2371–2376.

Tilcock, C. et al., "PEG–coated Lipid Vesicles with Encapsulated Technetium–99m as Blood Pool Agents for Nuclear Medicine," *Nucl. Med. Biol.,* 1994, 21(2),. 165–170.

Tilcock, C. et al., "$^{99m}$Tc–labeling of Lipid Vesicles Containing the Lipophilic Chelator PE–DTTA: Effect of Tin–to–chelate Ratio, Chelate Content and Surface Polymer on Labeling Efficiency and Biodistribution Behavior," *Nucl. Med. Biol.,* 1994, 21(1), 89–96.

Zarif, L.et al., "Synergistic Stabilization of Perfluorocarbon–Pluronic F–68 Emulsion by Perfluoroalkylated Polyhydroxylated Surfactants," *JAOCS,* 1989, 66(10), 1515–1523.

Miller, D.L., "Ultrasonic Detection of Resonant Cavitation Bubbles in a Flow Tube by Their Second–Harmonic Emissions", *Ultrasonics* Sep. 1981, 217–224.

Dittrich, "Cardiac Muscle Ischemia and Infarction", The Second Annual Int. Symposium on Contrasts Agents and Diagnostic Ultrasound, Atlantic City, NJ (May 7, 1996) (Abstract).

Pantely, "Intravenous Contrast Echocardiography–Tissue Imaging & Quantification of Coronary Blood Flow", The Second Annual Int. Symposium on Contrast Agents in Diagnostic Ultrasound, Atlantic City, NY (May 7, 1996) (Abstract).

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 776, pp. 169–174 (1984).

Hope et al., "Production of Large Unimellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. (1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echodardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition of Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, Experience, Sonicator™, Heat Systems—Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (asbtract).

M.R. Zalutsky et al., *Invest. Radiol.*, vol. 22(2), pp. 141–147 (1987) (abstract).

Crowe et al., *Archive of Biochemistry and Biophysics*, vol. 242, pp. 240–247 (1985).

Crowe et al., *Archives of Biochemistry and Biophysics*, vol. 220, pp. 477–484 (1983).
Dorland's Illustrated Medical Dictionary, p. 946, 27th ed. (W.B. Saunders Company, Philadelphia 1988).
*Liposome Technology*, Gregoriadis, G., ed., vol. I, pp. 1–18, 29–35, 51–65 and 79–107 (CRC Press Inc., Boca Raton, FL, (1984).
Madden et al., *Chemistry and Physics of Lipids*, vol. 53, pp. 37–46 (1990).
Sinkula et al., *J. Pharm. Sci.*, vol. 64, pp. 181–210 (1975).
Shiina et al., "Hyperthermiaby Low–frequency Synthesized Ultrasound", *IEEE Engineering*, pp. 879–880, vol. 2 (abstract).
McAvoy et al., *IEEE Engineering*, Ultrasonics Symposium Proceedings, vol. 2, pp. 677–1248 (abstract).
Chapman et al., "Biomembrane Phase Transitions", *J. Biol. Chem.*, 1974, 249:2512–2521.
Hug et al., "Liposomes for the Transformation of Eukaryotic Cells", *Biochimica et Biophysica Acta*, 1991, 1097:1–17.
Marsh, *CRC Handbook of Lipid Bilayers* (CRC Press, Boca Raton, FL 1990) pp. 139–141.
Szoka et al., "Procedure for Preparation of Liposomes With Large Internal Aqueous Space . . . ", *Proc. Natl. Acad. Sci.* 1978, 75:4194–4198.
Acoustic Imaging; AI5200; Convex Curved Linear Array Ultrasound Transducers Operator's Manual, Nov. 20, 1989, 4700–0003–1C, p. 4.
Bangham et al., "Diffusion of Univalent Ions across the Lamellae of Swollen Phospholipids", *J. Mol. Biol.*, 1965, 13:238–252.
Carson et al., *Ultrasound in Med. & Biol.* 3, 1978, 341–350.
Chiellini et al., *Polymers in Medicine II: Biomedical and Pharmaceutical Applications*, (Plenus Press, New York and London) pp. 387–396.
deGrier et al., "Relations Between Liposomes and Biomembranes", *Annals of The New York Academy of Sciences*, 1978, 308:85–99.
Felgner et al., "Lipofection: A highly efficient, lipid–mediated DNA–transfection procedure", *Proc. Natl. Acad. Sci.*, 1987, 84:7413–7417.
Gabizon et al., "Liposome formulations with prolonged circulation time in blood and enhanced uptake by tumors", *Proc. Natl. Acad. Sci.*, 1988, 85:6949–6953.
Garelli, et al., *Biochimica et Biophysica Acta*, vol. 1127:41–48 (1992).
Kawai et al., "New Procedure for DNA Transfection with Polycation and Dimethyl Sulfoxide", *Molecular and Cellular Biology*, 1984, 4:1172–1174.
Kuo et al., "Metallocene Antitumor Agents. Solution and Solid–State Molybdenocene Coordination . . . ", *J. Am. Chem. Soc.*, 1991, 113:9027–9045.
*Mammalian Cell Biotechnology: A Practical Approach*, M. Butler, 1991 (Oxford University Press, New York), p. 57–70.
Mathiowitz et al., "Photochemical Rupture of Microcapsules: A Model System", *Journal of Applied Polymer Science*, 1981, 26:809–822.
May et al., "Cationic Liposomes Enable Bovine Herpesvirus Type 2 DNA to Infect Cells", *Acta virol.*, 1991, 35:107.
Poznansky et al., "Biologica Approaches to the Controlled Delivery of Drugs: A Critical Review", *Pharmacol, Rev.*, 1984, 36:277–336.
Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.
Thompson, Larry, "At Age 2, Gene Therapy Enters a Growth Phase", *Science* 1992, 258:744–746.
Trubetskoy et al. "Cationic liposomes enhance targeted delivery and expression of exogenous DNA . . . ", *Biochimica et Biophysica Acta* 1992, 131:311–313.
Umemura et al., "Studies on Sonodynamic Cancer Therapy", *IEEE*, 1992, O–7803–0785, pp. 354–355.
Williams, "Human Gene Therapy: Searching for Better Vectors", *ASM News* [American Society for Microbology] 1992, 58:67–69.
Woodle et al., "Versatility in lipid compositions showing prolonged circulation . . . ", *Biochimica et Biophysica Acta* 1992, 1105:193–200.
Zhou et al., "Targeted delivery of DNA by liposomes and polymers", *J. of Controlled Release* 1992, 19:269–274.
Mathiowitz et al., "Polyanhydride Microspheres as Drug Carriers", *Journal of Applied Polymer Science*, vol. 35, pp. 755–774 (1988).
Sankaram et al., "Cholesterol–Induced Fluid–Phase Immiscibility in Membranes", *Proc. Natl. Acad. Sci.*, vol. 88, pp. 8686–8690 (1991).
Scientific Apparatus Catalog 92/93 (VWR Scientific, 1991), "Syringes", pp. 1511–1513; "Filtration, Syringe Filters", pp. 766–768; "Filtration, Membranes", pp. 750–753; "Filtration, Filter Holders", p. 744.
Gramiak et al., *Radiology*, "Detection of Intracardiac Blood Flow by Pulsed Echo–Ranging", pp. 415–418 (1971).
Feigenbaum et al., Circulation, "Identification of Ultrasound Echoes from the Left Ventricle by Use of Intracardiac Injections of Indocyanine Green", vol. XL1, pp. 615–621 (1970).
Santaella, et al., *FEBS 13463*, "Extended In Vivo Blood Circulation Time of Fluorinated Liposomes", vol. 336, No. 3, pp. 481–484 (1993).
Kost, et al, *Polymers in Medicine II*, Ultrasonic Modulated Drug Delivery Systems, pp. 387–396.
Brown and Langer, *Annual Review Medicine*, 1988, 39:22129, Annual Review, Inc., "Transdermal Delivery of Drugs", pp. 221–229.
Moseley, et al., *Microbubbles: A Novel MR Susceptibility Contrast Agent*, abstract, 1991, Napa, California Meeting of the Society for Magnetic Resonance in Medicine.
Ter–Pogossian, *Physical Principles and Instrumentation*, "Computed Body Tomography", Chapter 1, pp. 1–7.
Aronberg, *Techniques*, "Computed Body Tomography", Chapter 2, pp. 9–36.
Schutt et al., "Osmotically Stabilized Microbubble Sonographic Contrast Agents",*Acad. Radiol.*, vol. 3, Suppl. 2, pp. S188–S190 (Aug. 1996).
Frézard, et al., "Permeability and stability in buffer and in human serum of fluorinated phosphoplipd–based liposomes", *Biochimica et Biophysica Acta*, 1192, pp. 61–70 (1994).
Frézard, et al., "Fluorinated Phospholipid–Based Vesicles as Potential Drug Carriers: Encapsulation/Sustaining of Drugs and Stability in Human Serum",*Art, Cells, Blood Subs., and Immob. Biotech.*, 22(4), pp. 1403–1408 (1994).
Chang et al. Semipermeable Aqueous Microcapsules Canadian J. Of Phys. And Pharm. 1966 44:115–128.
Chang Semipereable Microcapsules Science 1964 146:524–525.

Deasy Microencapsulation and Related Drug Processes 1983 Ch 9 & 10 20:195–240.

Ter–Pogossian M. Physical Principles and Instrumentation Computed Body Tomography Lee eds. 1:1–7.

Yeung et al. Preparation of Microencapsulated Liposomes J. Microencapsulation 1988 5:331–337.

Mattrey et al. Gas Emulsions and Ultrasound Contrast Agents; Preliminary Results in Rabbits and Dogs Investigative Radiology 1994 29:S139–S141.

Meltzer et al. Transmission of Ultrasonic Contrast Through the Lungs Ultrasound in Med. & Biol. 1981 7:377–384.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. .575–578 (1986).

Lincoffe et al., "Intravitreal Expansion of Perfluorocarbon Bubbles", *Arch. Ophthalmol.*, 1980, 98, 1646.

Lincoff et al., "Intravitreal Longevity of Three Perfluorocarbon Gases", *Arch. Ophthalmol.*, 1980, 98, 1610–1611.

Lincoff et al., "The Perflurocarbon Gases in the Treatment of Retinal Detachment", *Ophthalmology*, 1983, 90(5), 546–551.

Gardner et al., "A Survey of Intraocular Gas Use in North America", *Arch. Ophthalmol.*, 1988, 106, 1188–1189.

Unger et al., "Liposomal MR Contrast Agents", *J. Liposome Research*, 1994, 4(2), 811–834.

Reexamination of U.S. application No. 5,527,521, Reexam Control No. 90/004,719.

Reexamination of U.S. application No. 5,547,656, Reexam Control No. 90/004,720.

Hynynen et al., "The Usefulness of a Contrast Agent and Gradient Recalled Acquisition in a Steady–State Imaging Sequence for Magnetic Resonance Imaging–Guided Noninvasive Ultrasound Surgery", *Investigative Radiology*, 1994, 29(10), 897–903.

Ding, X.C., "Scavenging effect of EDTA–fluorocarbon microspheres on 210 lead," *Chung Kuto Yao Li Hsueh Pao*, 1989, 10(5), 473–475 (abstract only).

Kinsler, L. E., et al., *Fundamentals of Acoustics*, $3^{rd}$ Ed., 1982, 228–331.

Meessen, H. (ed.), *Microcirculation*, Springer–Verlag, Berlin Heidelberg, New York, 1997, 44.

Ring, J., et al., "Humanalbuminunverträglichkeit: klinische und immunologische untersuchungen," *Clinical Weekly*, 1974, 52, 595–598.

Robinson, et al., F.J. Fry (ed.), "Ultrasound: its applications in medicine and biology," Elsevier Scientific Publishing Company, 1978, vol. 3, Chap. XI, 593–596.

Silbernagl, S., et al., "Pocket atlas of physiology," Georg Thieme Verlag, Stuttgart, New York, 1983, 156–157.

Wells, P.N.T., "Pulse–echo methods," *Biomedical Ultrasonics*, Academic Press, 1977, 209–220.

THERAPEUTIC DELIVERY SYSTEMS

RELATED APPLICATIONS

This application is a divisional of U.S. application Ser. No. 08/160,232 filed Nov. 30, 1993, now U.S. Pat. No. 5,542,935, which is a continuation-in-part of U.S. application Ser. No. 08/159,687 filed Nov. 30, 1993, now U.S. Pat. No. 5,585,112, and U.S. application Ser. No. 08/159,674 filed Nov. 30, 1993, now abandoned, which are continuation-in-part of U.S. application Ser. No. 08/076,250 filed Jun. 11, 1993, now U.S. Pat. No. 5,580,575, which is a continuation-in-part of U.S. application Ser. No. 07/716,899 filed Jun. 18, 1991, now abandoned, and U.S. application Ser. No. 07/717,084 filed Jun. 18, 1991, now U.S. Pat. No. 5,228,446, which are continuations-in-part of U.S. application Ser. No. 07/569,828 filed Aug. 20, 1990, now U.S. Pat. No. 5,088,499, which is a continuation-in-part of U.S. application Ser. No. 07/455,707 filed Dec. 22, 1989, now abandoned, the disclosures of each of which are incorporated herein by reference in their entirety.

BACKGROUND OP THE INVENTION

1. Field of the Invention

This invention relates to therapeutic delivery systems, and more specifically, to gaseous precursor-containing microspheres comprising a therapeutic compound. The invention further relates to methods for employing such microspheres as therapeutic delivery systems.

2. Background of the Invention

Targeted therapeutic delivery means are particularly important where the toxicity of a drug is an issue. Specific therapeutic delivery methods potentially serve to minimize toxic side effects, lower the required dosage amounts, and decrease costs for the patient. The present invention is directed to addressing these and/or other important needs in the area of therapeutic delivery.

A variety of imaging techniques have been used for detection and diagnosis of diseases in animals and humans. X-rays represent one of the first techniques used for diagnostic imaging. The images obtained through this technique reflect the electron density of the object being imaged. Contrast agents, such as barium or iodine, have been used over the years to attenuate or block X-rays such that the contrast between various structures is increased. X-rays, however, are known to be somewhat dangerous, since the radiation employed in X-rays is ionizing, and the various deleterious effects of ionizing radiation are cumulative.

Another important imaging technique is magnetic resonance imaging (MRI). This technique, however, has various drawbacks, such as expense and shear size of an MRI scanner rendering it stationary which prohibits portable examination. In addition, MR1 is not available at many medical centers.

Radionuclides, employed in nuclear medicine, provide a further imaging technique. In employing this technique, radionuclides such as technetium labeled compounds are injected into the patient, and images are obtained from gamma cameras. Nuclear medicine techniques, however, suffer from poor spatial resolution and expose the animal or patient to the deleterious effects of radiation. Furthermore, the handling and disposal of radionuclides is problematic.

Ultrasound is another diagnostic imaging technique which is unlike nuclear medicine and X-rays since it does not expose the patient to the harmful effects of ionizing radiation. Moreover, unlike magnetic resonance imaging, ultrasound is relatively inexpensive and may be conducted as a portable examination. In using the ultrasound technique, sound is transmitted into a patient or animal via a transducer. When the sound waves propagate through the body, they encounter interfaces from tissues and fluids. Depending on the acoustic properties of the tissues and fluids in the body, the ultrasound sound waves are partially or wholly reflected or absorbed. When sound waves are reflected by an interface they are detected by the receiver in the transducer and processed to form an image. The acoustic properties of the tissues and fluids within the body determine the contrast which appears in the resultant image.

Advances have been made in recent years in ultrasound technology. However, despite these various technological improvements, ultrasound is still an imperfect tool in a number of respects, particularly with regard to the imaging and detection of disease in the liver and spleen, kidneys, heart and vasculature, including measuring blood flow. The ability to detect and measure these regions depends on the difference in acoustic properties between tissues or fluids and the surrounding tissues or fluids. As a result, contrast agents have been sought which will increase the acoustic difference between tissues or fluids and the surrounding tissues or fluids in order to improve ultrasonic imaging and disease detection.

The principles underlying image formation in ultrasound have directed researchers to the pursuit of gaseous contrast agents. Changes in acoustic properties or acoustic impedance are most pronounced at interfaces of different substances with greatly differing density or acoustic impedance, particularly at the interface between solids, liquids and gases. When ultrasound sound waves encounter such interfaces, the changes in acoustic impedance result in a more intense reflection of sound waves and a more intense signal in the ultrasound image. An additional factor affecting the efficiency or reflection of sound is the elasticity of the reflecting interface. The greater the elasticity of this interface, the more efficient the reflection of sound. Substances such as gas bubbles present highly elastic interfaces. Thus, as a result of the foregoing principles, researchers have focused on the development of ultrasound contrast agents based on gas bubbles or gas containing bodies and on the development of efficient methods for their preparation.

Ryan et al., in U.S. Pat. No. 4,544,545, disclose phospholipid liposomes having a chemically modified cholesterol coating. The cholesterol coating may be a monolayer or bilayer. An aqueous medium, containing a tracer, therapeutic, or cytotoxic agent, is confined within the liposome. Liposomes, having a diameter of 0.001 microns to 10 microns, are prepared by agitation and ultrasonic vibration.

D'Arrigo, in U.S. Pat. Nos. 4,684,479 and 5,215,680, teaches a gas-in-liquid emulsion and method for the production thereof from surfactant mixtures. U.S. Pat. No. 4,684,479 discloses the production of liposomes by shaking a solution of the surfactant in a liquid medium in air. U.S. Pat. No. 5,215,680 is directed to a large scale method of producing lipid coated microbubbles including shaking a solution of the surfactant in liquid medium in air or other gaseous mixture and filter sterilizing the resultant solution.

WO 80/02365 discloses the production of microbubbles having an inert gas, such as nitrogen; or carbon dioxide, encapsulated in a gellable membrane. The liposomes may be stored at low temperatures and warmed prior and during use in humans. WO 82/01642 describes microbubble precursors and methods for their production. The microbubbles are formed in a liquid by dissolving a solid material. Gas-filled voids result, wherein the gas is 1.) produced from gas present in voids between the microparticles of solid precursor aggregates 2.) absorbed on the surfaces of particles of the precursor, 3.) an integral part of the internal structure of particles of the precursor, 4.) formed when the precursor reacts chemically with the liquid, and 5.) dissolved in the liquid and released when the precursor is dissolved therein.

In addition, Feinstein, in U.S. Pat. Nos. 4,718,433 and 4,774,958, teach the use of albumin coated microbubbles for the purposes of ultrasound.

Widder, in U.S. Pat. Nos. 4,572,203 and 4,844,882, disclose a method of ultrasonic imaging and a microbubble-type ultrasonic imaging agent.

Quay, in WO 93/05819, describes the use of agents to form microbubbles comprising especially selected gases based upon a criteria of known physical constants, including 1) size of the bubble, 2) density of the gas, 3) solubility of the gas in the surrounding medium, and 4) diffusivity of the gas into the medium.

Kaufman et al., in U.S. Pat. No. 5,171,755, disclose an emulsion comprising an highly fluorinated organic compound, an oil having no substantial surface activity or water solubility and a surfactant. Kaufman et al. also teach a method of using the emulsion in medical applications.

Another area of significant research effort is in the area of targeted drug delivery. The methods and materials in the prior art for introduction of genetic materials to, for example, living cells is limited and ineffective. To date several different mechanisms have been developed to deliver genetic material to living cells. These mechanisms include techniques such as calcium phosphate precipitation and electroporation, and carriers such as cationic polymers and aqueous-filled liposomes. These methods have all been relatively ineffective in vivo and only of limited use for cell culture transfection. None of these methods potentiate local release, delivery and integration of genetic material to the target cell.

Better means of delivery for therapeutics such as genetic materials are needed to treat a wide variety of human and animal diseases. Great strides have been made in characterizing genetic diseases and in understanding protein transcription but relatively little progress has been made in delivering genetic material to cells for treatment of human and animal disease.

A principal difficulty has been to deliver the genetic material from the extracellular space to the intracellular space or even to effectively localize genetic material at the surface of selected cell membranes. A variety of techniques have been tried in vivo but without great success. For example, viruses such as adenoviruses and retroviruses have been used as vectors to transfer genetic material to cells. Whole virus has been used but the amount of genetic material that can be placed inside of the viral capsule is limited and there is concern about possible dangerous interactions that might be caused by live virus. The essential components of the viral capsule may be isolated and used to carry genetic material to selected cells. In vivo, however, not only must the delivery vehicle recognize certain cells but it also must be delivered to these cells. Despite extensive work on viral vectors, it has been difficult to develop a successfully targeted viral mediated vector for delivery of genetic material in vivo.

Conventional, liquid-containing liposomes have been used to deliver genetic material to cells in cell culture but have generally been ineffective in vivo for cellular delivery of genetic material. For example, cationic liposome transfection techniques have not worked effectively in vivo. More effective means are needed to improve the cellular delivery of therapeutics such as contrast agents and genetic material.

Despite the advances that have been made, the prior art has still not solved many of the problems inherent in the development of ultrasound contrast agents. Gases may diffuse out of stabilizing emulsions or particle coatings and the efficacy of the product may be lost. In all of the gaseous based contrast media for ultrasound under development to date, the microspheres are relatively large, e.g. on the order of 2 to 7 microns, such that sufficient backscatter for ultrasonic contrast enhancement is provided. The large size of these particles makes it very difficult to exclude potential contaminants from the injection such as bacteria passing into the patient during the injection. Gas-containing microspheres currently under development are generally unstable in vivo and do not persist long enough to provide ideal contrast enhancement.

The present invention is directed to addressing the foregoing, as well as other important needs in the area of contrast agents for ultrasonic imaging and vehicles for the effective targeted delivery of therapeutics. The present invention is dedicated to providing improved and safer contrast agents for diagnostic ultrasound and delivery of genetic material.

SUMMARY OF THE INVENTION

The present invention provides therapeutic delivery systems for site-specific delivery of therapeutics using gas-filled microspheres. The microspheres contain a temperature activated gaseous precursor which becomes a gas upon activation at a selected temperature. Once the microspheres have been introduced into the patient's body, a therapeutic compound may be targeted to specific tissues through the use of sonic energy, microwave energy, magnetic energy, or hyperthermia, which is directed to the target area and causes the microspheres to rupture and release the therapeutic compound.

Specifically, the present invention provides targeted therapeutic delivery systems comprising a temperature activated gaseous precursor-filled microsphere comprising a therapeutic compound.

The invention also contemplates methods for the controlled delivery of therapeutic compounds to a region of a patient comprising: (i) administering to the patient temperature activated gaseous precursor-filled microspheres comprising a therapeutic compound; (ii) monitoring the microspheres using ultrasound to determine the phase transition of the gaseous precursor from a liquid to a gas and to determine the presence of the microspheres in the region; and (iii) rupturing the microspheres using ultrasound to release the therapeutic compound in the region.

In addition, the present invention provides methods and apparatus for preparing temperature activated gaseous precursor-filled liposomes suitable for use in delivery of contrast agents and as drug delivery agents. Preferred methods of the present invention provide the advantages, for example, of simplicity and potential cost savings during manufacturing of temperature activated gaseous precursor-filled microspheres comprising therapeutic compounds.

The temperature activated gaseous precursor-filled liposomes are particularly useful as carriers for contrast agents and drugs. Unlike liposomes of the prior art that have a liquid interior suitable only for encapsulating drugs that are water soluble, the temperature activated gaseous precursor-filled liposomes made according to the present invention are particularly useful for encapsulating lipophilic drugs. Furthermore, lipophilic derivatives of drugs may be incorporated into the lipid layer readily, such as alkylated derivatives of metallocene dihalides. Kuo et al., *J. Am. Chem. Soc.* 1991, 113, 9027–9045.

It is believed that one of the advantages of the present invention includes the capture of ultrasonic energy by the gaseous precursor in the microspheres which, upon changing the liquid gaseous precursor to a gas at a selected transition temperature, and rupture of the microsphere, create local increase in membrane fluidity, thereby enhancing cellular uptake of the therapeutic compound.

These and other features of the invention and the advantages thereof will be set forth in greater detail in the figures and the description below.

DETAILED DESCRIPTION OF THE INVENTION

Figure 5:
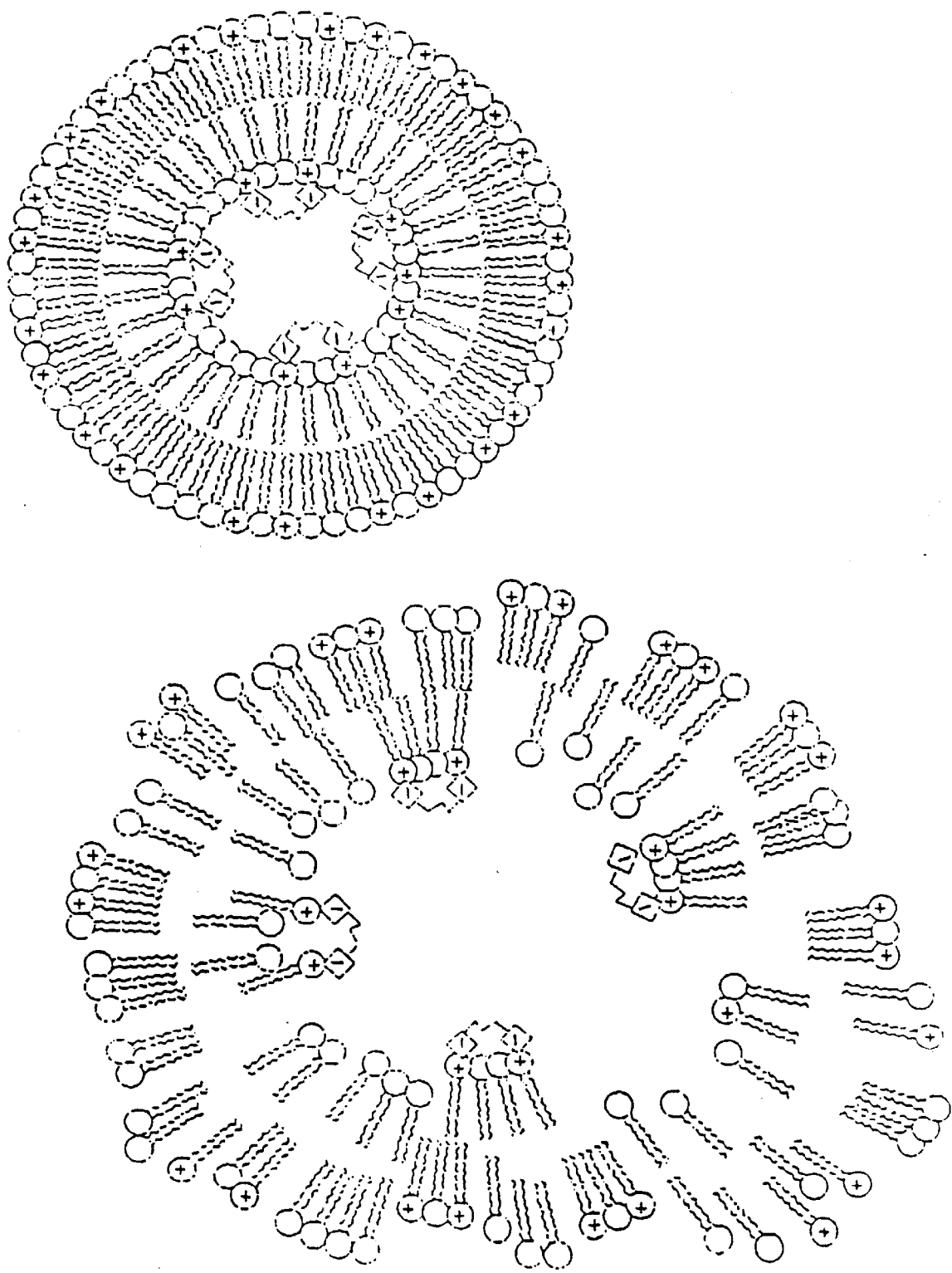
FIG. 5 is a diagrammatical depiction of two liposomes. The upper liposome is a gaseous precursor-filled liposome microsphere having a therapeutic negatively charged drug compound, indicated by the minus signs enclosed in the squares, attached to the interior of the liposome, and the lower liposome shows the subsequent release of the therapeutic upon the application of ultrasound.
Figure 6:
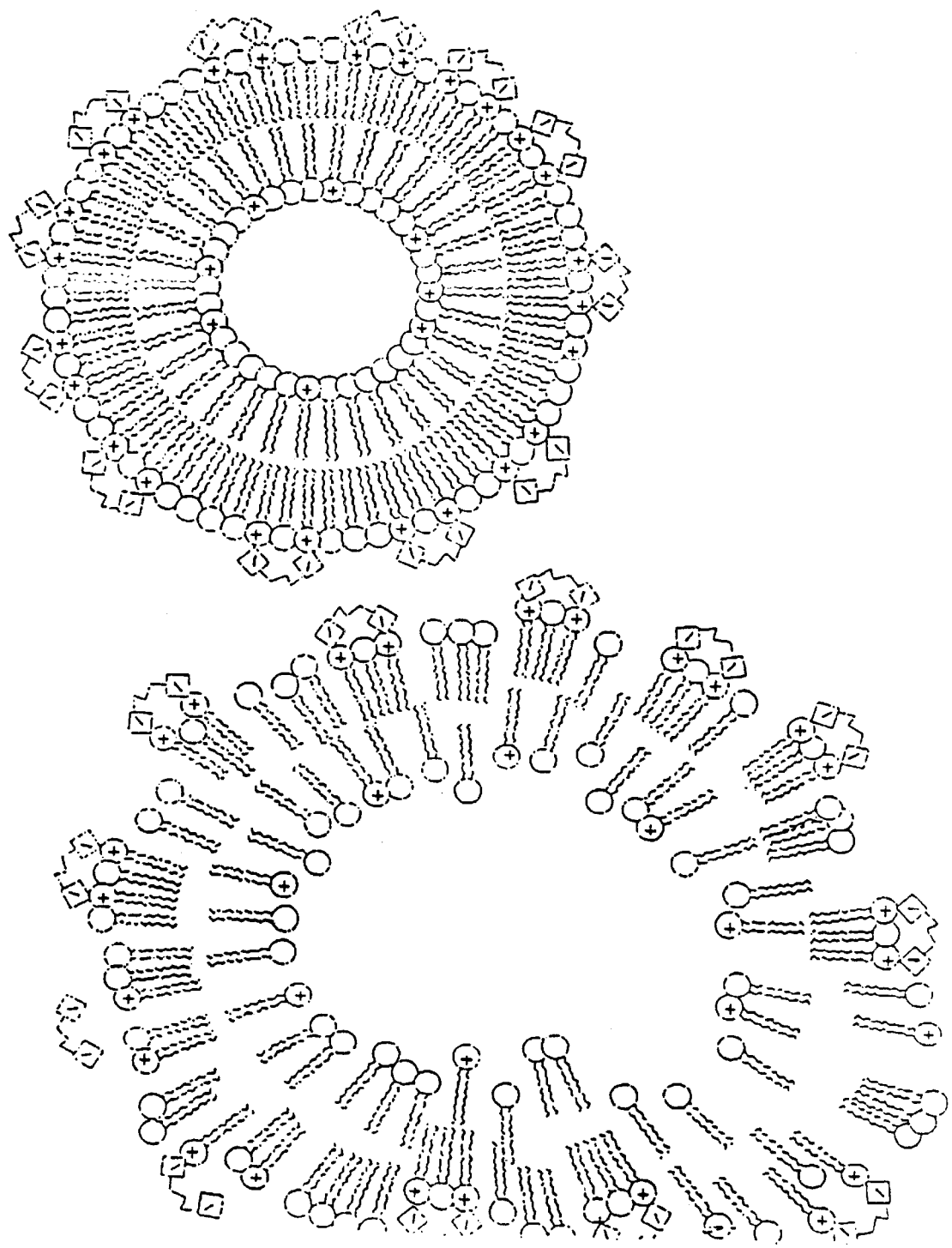
FIG. 6 is a diagrammatical depiction of two liposomes. The upper liposome is a gaseous precursor-filled liposome microsphere having a therapeutic negatively charged drug compound attached to the exterior of a liposome microsphere, and the lower liposome shows the subsequent release of the therapeutic upon the application of ultrasound.
Figure 7A:
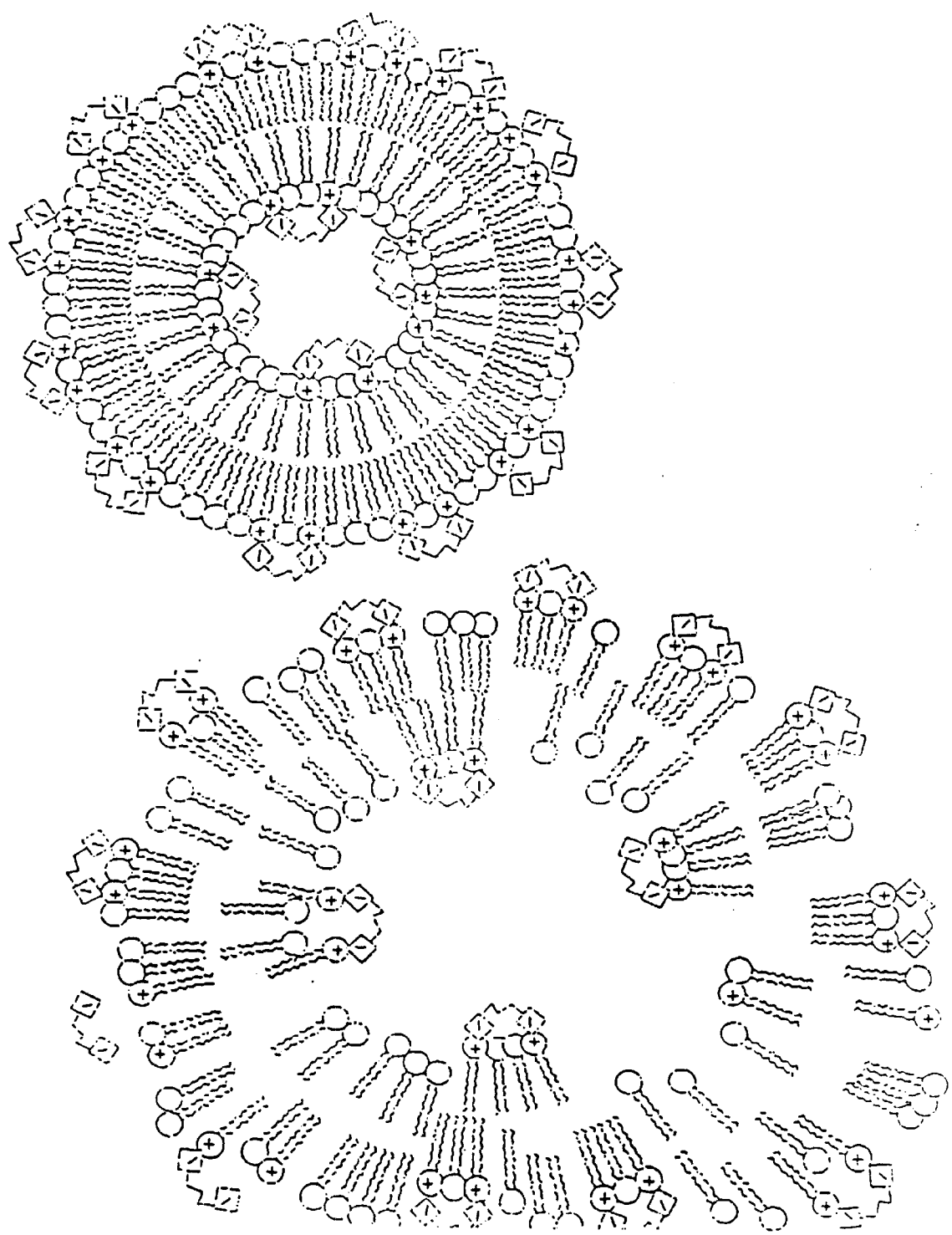
FIG. 7 is a diagrammatical illustration of FIGS. 7A and B are each diagrammatical illustrations of two liposomes. In each, the upper liposome is a gaseous precursor-filled liposome microsphere having a therapeutic compound, such as a negatively charged drug (A) or a positively charged drug (B) attached to the interior and the exterior of a liposome microsphere, and the lower liposome shows the subsequent release of the therapeutic upon the application of ultrasound.
Figure 7B:
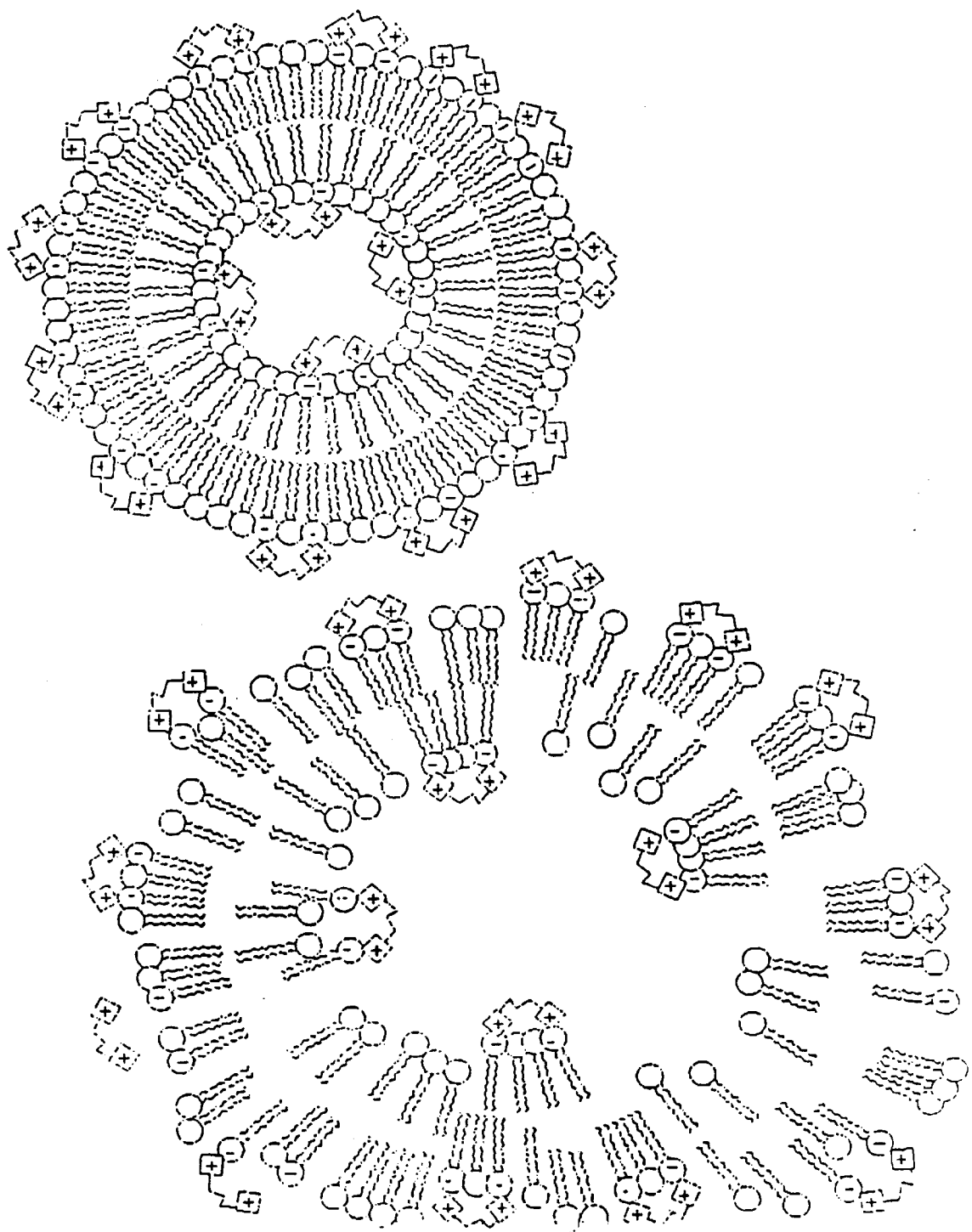
Figure 8:
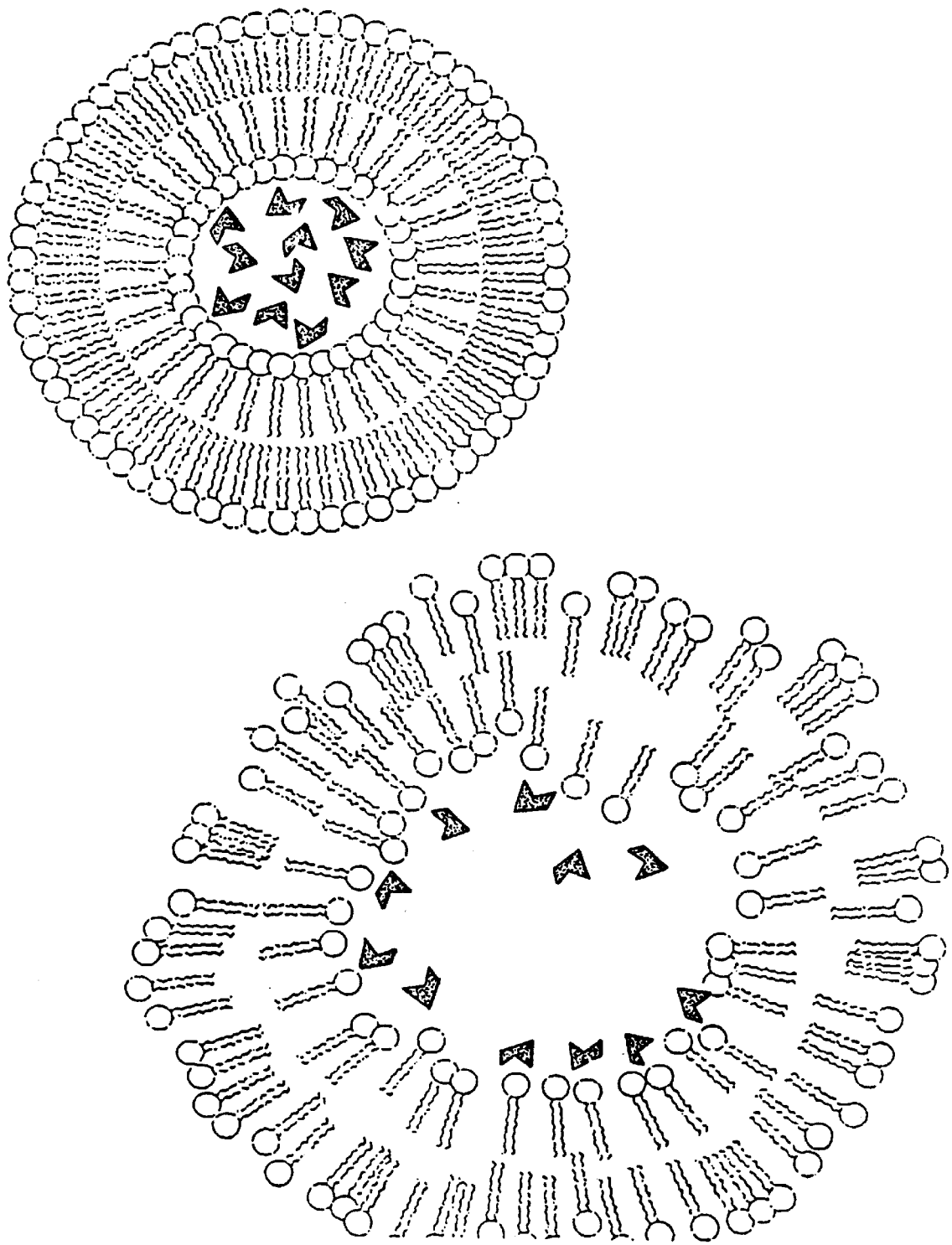
FIG. 8 is a diagrammatical illustration of two liposomes. The upper liposome is a gaseous precursor-filled liposome microsphere having a therapeutic compound, indicated by the shaded members, encapsulated within the internal gaseous precursor-filled void, and the lower liposome shows the subsequent release of the therapeutic upon the application of ultrasound.

The present invention provides a targeted therapeutic delivery system comprising a temperature activated gaseous precursor-filled microsphere comprising a therapeutic compound. A microsphere is defined as a structure having a relatively spherical shape with an internal void. The therapeutic compound may be embedded within the wall of the microsphere, encapsulated in the microsphere and/or attached to the microsphere, as desired. The phrase "attached to" or variations thereof, as used herein in connection with the location of the therapeutic compound, means that the therapeutic compound is linked in some manner to the inside and/or the outside wall of the microsphere, such as through a covalent or ionic bond, or other means of chemical or electrochemical linkage or interaction, as shown, for example, in FIGS. 5, 6 and 7. The phrase "encapsulated in" or variations thereof as used in connection with the location of the therapeutic compound denotes that the therapeutic compound is located in the internal microsphere void, as shown, for example, in FIG. 8. The phrase "embedded within" or variations thereof as used in connection with the location of the therapeutic compound, signifies the positioning of the therapeutic compound within the microsphere wall, as shown, for example in FIGS. 1, 2, 3 and 4. The phrase "comprising a therapeutic" denotes all of the varying types of therapeutic positioning in connection with the microsphere. Thus, the therapeutic can be positioned variably, such as, for example, entrapped within the internal void of the gaseous precursor-filled microsphere, situated between the gaseous precursor and the internal wall of the gaseous precursor-filled microsphere, incorporated onto the external surface of the gaseous precursor-filled microsphere and/or enmeshed within the microsphere structure itself. It will also be understood by one skilled in the art, once armed with the present disclosure, that the walls of the microsphere, when it comprises a lipid, may have more than one lipid bilayer.

The microspheres of the present invention may be used for targeted therapeutic delivery either in vivo or in vitro. Preferably, each individual microsphere is capable of releasing substantially all of the therapeutic compound upon the application of ultrasound. The phrase "substantially all" refers to at least about 80%, and preferably at least about 90%, and most preferably, about 100%. In certain embodiments, the release of all of the therapeutic compound from all of the microspheres is immediate; in other embodiments, the release is gradual. It will be understood by one skilled in the art, once armed with the present disclosure, that the preferred rate of release will vary depending upon the type of therapeutic application. In certain preferred embodiments, the therapeutic compound is encapsulated in the microspheres, for example, and thus substantially all of the therapeutic compound is immediately released from the microsphere upon rupture. Further, it will be understood by one skilled in the art, once armed with the present disclosure, that the frequency and duration of ultrasound applied can be varied to achieve a desired rate of release of the therapeutic compound.

Thus, as noted above, the therapeutic to be delivered may be encapsulated within the gas-containing microsphere, such as with a variety of therapeutics, incorporated onto the surface of the gas-containing microsphere, such as by coating a cationic lipid with negatively charged DNA or an anionic lipid with a positively charged drug, and/or embedded within the walls of the gas-containing microsphere, such as with lipophilic therapeutics. The microspheres may be prepared as microspheres comprising a therapeutic, or the microspheres may be prepared without the therapeutic and the therapeutic added to the gaseous precursor-filled microspheres prior to use. In the latter case, for example, a therapeutic could be added to the gaseous precursor-filled microspheres in aqueous media and shaken in order to coat the microspheres with the therapeutic.

Figure 19:
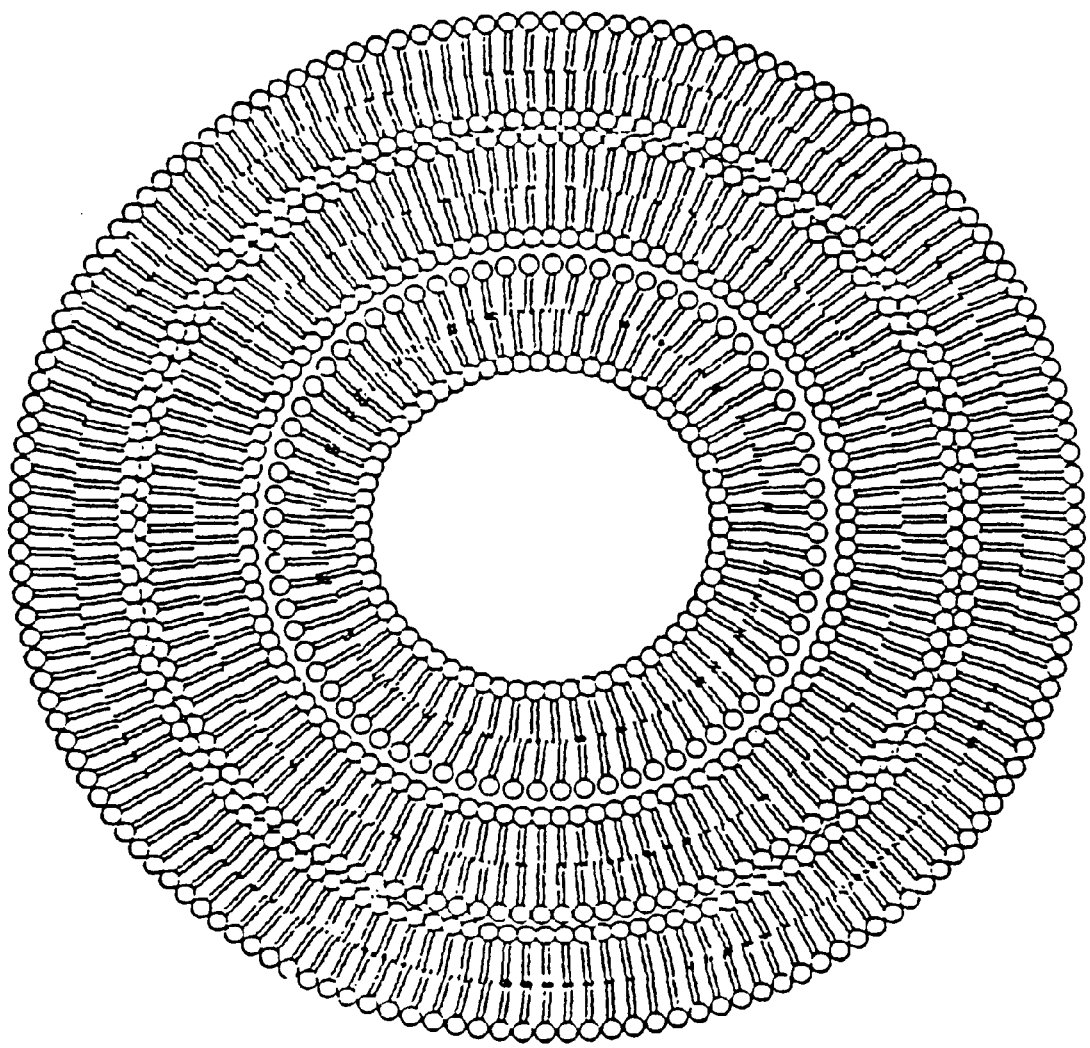
FIG. 19 is a diagrammatic illustration of a temperature activated gaseous precursor-filled liposome prior to temperature activation. The liposome has a multilamellar membrane.
Figure 20:
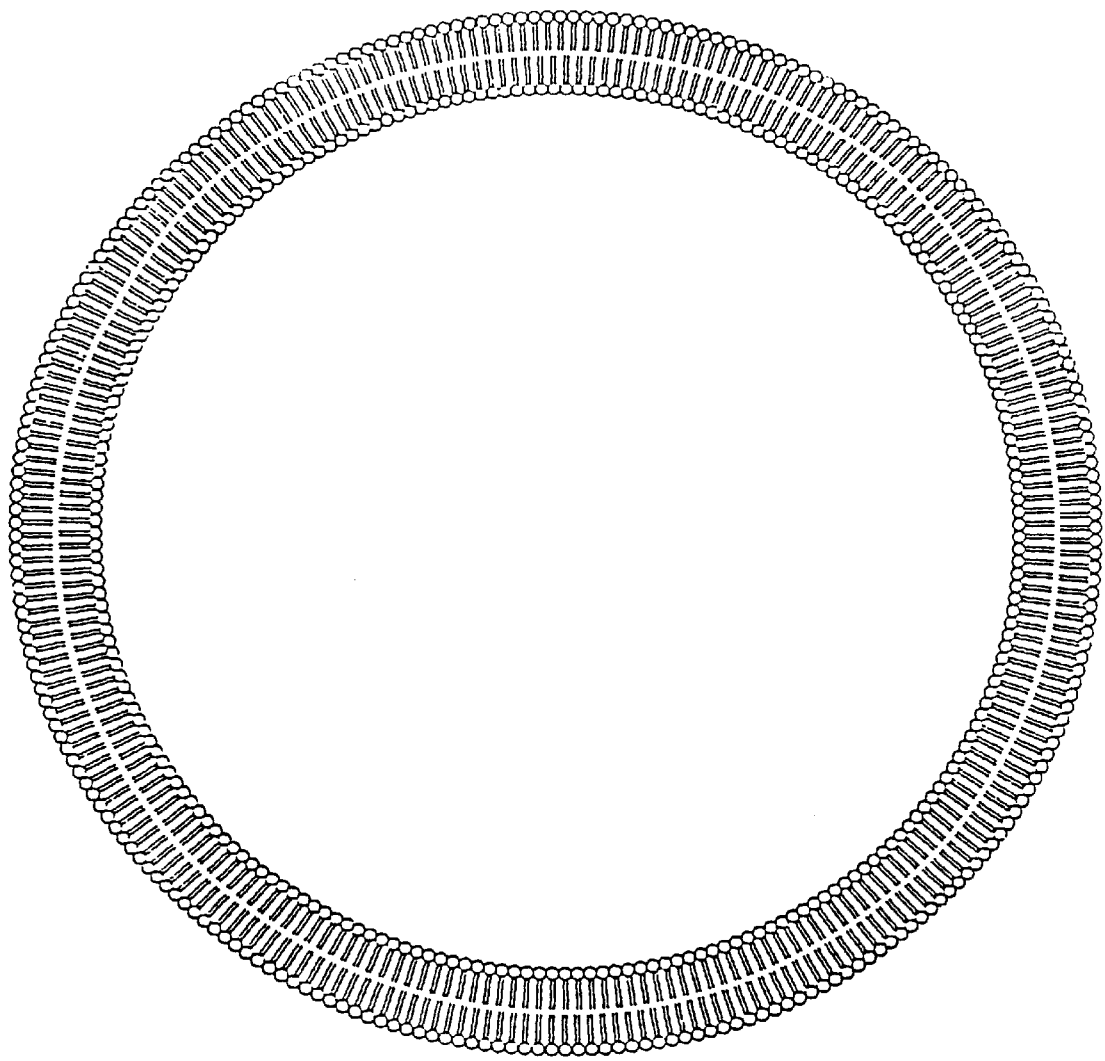
FIG. 20 is a diagrammatic illustration of a temperature activated liquid gaseous precursor-filled liposome after temperature activation of the liquid to gaseous state resulting in a unilamellar membrane and expansion of the liposome diameter.

As used herein, the phrase "temperature activated gaseous precursor" denotes a compound which, at a selected activation or transition temperature, changes phases from a liquid to a gas. Activation or transition temperature, and like terms, refer to the boiling point of the gaseous precursor, the temperature at which the liquid to gaseous phase transition of the gaseous precursor takes place. Useful gaseous precursors are those gases which have boiling points in the range of about −100° C. to about 70° C. The activation. temperature is particular to each gaseous precursor. This concept is illustrated in FIGS. 19 and 20. An activation temperature of about 37° C., or human body temperature, is preferred for gaseous precursors of the present invention. Thus, a liquid gaseous precursor is activated to become a gas at 37° C. However, the gaseous precursor may be in liquid or gaseous phase for use in the methods of the present invention. Suitable temperature-activated gaseous precursors are well known to those skilled in the art, and include for example, methylactate, a compound which is a liquid at histologic or physiologic temperatures, body temperature of humans. As those skilled in the art would recognize, such compounds can be activated prior to administration or, as in the case of methylactate, can be activated upon injection into the patient. Even when exposure to the appropriate temperature occurs prior to administration, an advantage is achieved in that the microsphere prepared with the gaseous precursor is a more stable entity, in the liquid and gas phases, than a microsphere which has been placed on the shelf with a gas encapsulated therein. Accordingly, a longer shelf life is afforded to microspheres which encapsulate a temperature activated gaseous precursor. The resulting gaseous precursor-containing microspheres are capable of being detected easily in vivo because of their lower density as compared to the surrounding bodily structures and organs. In addition, as those skilled in the art would recognize, such temperature sensitive gas-forming microspheres may be used as indicators of in vivo temperature.

In the preferred embodiment of the invention, the gaseous precursor changes from a liquid into a gaseous phase upon administration to the patient, from the ambient or room temperature. Depending upon the gaseous precursor the contrast medium may be stored under refrigeration and may also be kept chilled, for example, by an insulated syringe, prior to I.V. injection. Upon injection, the gaseous precursor then expands for maximal ultrasonic enhancement.

The gaseous precursor may be selected so as to form the gas in situ in the targeted tissue or fluid (e.g. upon application of ultrasound, microwave, magnetic energy, or light energy (laser or infrared, for example), in vivo upon entering the patient or animal, prior to use, during storage, or during manufacture. The methods of producing the temperature-activated gaseous precursor-filled microspheres are carried out at a temperature below the boiling point of the gaseous precursor. In this embodiment, the gaseous precursor is entrapped within a microsphere such that the phase transition does not occur during manufacture. Instead, the gaseous precursor-filled microspheres are manufactured in the liquid phase of the gaseous precursor. Activation of the phase transition may take place at any time as the temperature is allowed to exceed the boiling point of the precursor.

For gaseous precursors having low temperature boiling points, liquid precursors may be emulsified using a microfluidizer device chilled to a low temperature. The boiling points may also be depressed using solvents in liquid media to utilize a precursor in liquid form. Alternatively, an upper limit of about 70° C. may be attained with focused high energy ultrasound.

While in the preferred embodiment of the present invention, the gaseous precursors form a gas in vivo via temperature mediated phase transition, gaseous precursors may also be used to produce stable contrast media wherein the gas is derived from a precursor and achieves the gaseous state prior to entering the patient. This embodiment is prepared by introducing the gaseous precursor to the microsphere during the manufacturing process.

The gaseous precursors may be utilized to create stable gas-filled microspheres which are pre-formed prior to use. In this form of the invention, the gaseous precursor is added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas-filled lipid spheres which entrap the gas of the gaseous precursor, ambient gas (e.g. air), or coentrap gas and ambient gas. This phase transition can be used for optimal mixing and stabilization of the contrast medium. For example, the gaseous precursor, perfluorobutane, for example, can be entrapped in liposomes and as the temperature is raised beyond 3° C. (boiling point of perfluorobutane), liposomally entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents surprisingly stable gas-filled liposomes result.

Similarly, perfluoropentane which is liquid at room temperature may be entrapped in liposomes. A small quantity (0.76–1.52 µL) of the liquid perfluoropentane precursor may be added to a lipid solution (e.g. 82 mole % dipalmitoylphosphatidylcholine, 8 mole % dipalmitoylphosphatidylethanolamine-PEG 500 and 10 mole % dipalmitoylphosphatidic acid) in a solution of 80 volume % normal saline, 10 volume % glycerol with 10 volume % propylene glycol at room temperature and shaken. Then the temperature of the suspension is raised past the phase transition temperature (e.g. over 30° C.) to initiate the liquid to gaseous conversion of the perfluoropentane gaseous precursor. Foaming results and gas filled liposomes are produced. The mean size of gas filled liposomes produced are generally in excess of 20 microns as produced by vortexing or shaking on a Wig-L-Bug™. The liposomes can be filtered and a single passage through an 8.0 micron filter is adequate to remove more than 99% of the particles over 10 microns in size. As the liposomes are compliant and pliable, they reform into smaller lipid coated liposomes after filtration. When the liposomes are cooled to room temperature or lower, the entrapped perfluoropentane gaseous precursor goes back into the liquid state and the result is entrapped nanodroplets of perfluoropentane within the liposomes. Upon rewarming (e.g. injection in vivo) the appropriate sized gas liposomes then form.

An alternate method of entrapping the perfluoropentane gaseous precursor is illustrated. A small quantity (0.76–1.54 µL) of perfluoropentane is added to an aqueous solution of lipids as described above, with a different method of agitation utilized. The material is placed in a Microfluidizer (Microfluidics, Newton, Mass.) and subject to 15 passes at 16,000 psi at 20° C. By adjusting the pressure and number of passes, the size of the liposomes is accordingly adjusted. Small liposomes with mean diameter of about 100 nm each entrapping an average sized nanodroplet of about 5 nm diameter of perfluoropentane are thereby produced. Upon expansion after temperature mediated gas conversion (e.g. upon injection in vivo) each nanodroplet of this size will produce a liposome slightly less than 10 microns in diameter. In this case, the resulting liposomes will be partially coated with lipid and the size of the resultant liposomes is controlled. In a manufacturing process, the unentrapped perfluoropentane could be removed by several ways. Firstly, liquid perfluoropentane is dense and can sink to the bottom, the small lipid entrapped nanodroplets or microparticles will tend to remain in suspension. Secondly, the suspension can be warmed; larger unentrapped microdroplets will form larger liposomes than the nanodroplets of perfluoropentane and the larger liposomes will rise more quickly to the top of a vessel and can thereby be removed. A very practical method is to use filtration which can be performed as an in-line process during injection into the patient.

A micellular formulation may be substituted for a liposome (lipid bilayers entrapping the nanodroplet of perfluoropentane). A micellular formulation has the appropriate mixture of lipids, e.g. peanut oil with sodium cholate, cholesterol and glycerol (optionally with a portion of PEGylated lipids). A microfluidizer process can be used to produce a micellular formulation of the gaseous precursor to produce nanoparticles or microparticles of the emulsion wherein each particle entraps on average a nanodroplet of about 5 nm diameter or less of perfluoropentane.

Sonication can be used when performed at a temperature below the phase transition temperature of the gaseous precursor. In this case, the gaseeous precursor may be emulsified by sonication such that nanodroplets of liquid precursor are dispersed within the suspending medium (e.g. dispersed within a suspension of phospholipids and thereby entrapped as nanodroplets within the liposomes).

Accordingly, the gaseous precursors of the present invention may be selected to form a gas-filled liposome in vivo or designed to produce the gas-filled liposome in situ, during the manufacturing process, on storage, or at some time prior to use. Knowing the amount of liquid in a droplet of liquid gaseous precursor, the size of the liposome upon attaining the gaseous state may be determined.

As a further embodiment of this invention, by preforming the liquid state of the gaseous precursor into an aqueous emulsion and maintaining a known size, the maximum size of the microbubble may be estimated by using the idea gas law, once the transition to the gaseous state is effectuated. The ideal gas law assumes that the gas phase is formed instantaneously and no gas in the newly formed microbubble has been depleted due to diffusion into the liquid (generally aqueous in nature). Hence, from a known liquid volume in the emulsion, one actually would predict an upper limit to the size of the gaseous liposome.

Pursuant to the present invention, a emulsion of lipid gaseous precursor-containing liquid droplets of defined size may be formulated, such that upon reaching a specific temperature, the boiling point of the gaseous precursor, the droplets will expand into gas liposomes of defined size. The defined size represents an upper limit to the actual size because factors such as gas diffusing into solution, loss of gas to the atmosphere, and the effects of increased pressure are factors for which the ideal gas law cannot account.

The ideal gas law and the equation for calculating the increase in volume of the gas bubbles on transition from the liquid to gaseous states follows:

The ideal gas law predicts the following:

$$PV=nRT$$

where
P0=pressure in atmospheres
V=volume in liters
n=moles of gas
T=temperature in ° K
R=ideal gas constant=22.4 L atmospheres deg$^{-1}$ mole$^{-1}$ With knowledge of volume, density, and temperature of the liquid in the emulsion of liquids, the amount (e.g. number of moles) of liquid precursor as well as the volume of liquid precursor, a priori, may be calculated, which when converted to a gas, will expand into a liposome of known volume. The calculated volume will reflect an upper limit to the size of the gaseous liposome assuming instantaneous expansion into a gas liposome and negligible diffusion of the gas over the time of the expansion.

Thus, stabilization of the precursor in the liquid state in an emulsion whereby the precursor droplet is spherical, the volume of the precursor droplet may be determined by the equation:

$$\text{Volume (sphere)}=4/3\ \pi r^3$$

where
r=radius of the sphere

Thus, once the volume is predicted, and knowing the density of the liquid at the desired temperature, the amount of liquid (gaseous precursor) in the droplet may be determined. In more descriptive terms, the following can be applied:

$$V_{gas}=4/3\pi(r_{gas})^3$$

by the ideal gas law, $$PV=nRT$$

substituting reveals, $$V_{gas}=nRT/P_{gas}$$

or, (A) $n=4/3[\pi r_{gas}{}^3]P/RT$ amount $n=4/3[\pi r_{gas}{}^3 P/RT]*MW_n$

Converting back to a liquid volume (B) $V_{liq}=[4/3[\pi r_{gas}{}^3]P/RT]*\ MW_n/D]$ where D=the density of the precursor Solving for the diameter of the liquid droplet, (C) $diameter/2\ =[3/4\pi[4/3*\ [\pi r_{gas}{}^3]P/RT]MW_n/D]^{1/3}$ which reduces to $Diameter=2[[r_{gas}{}^3]P/RT[MW_n/D]]^{1/3}$ As a further embodiment of the present invention, with the knowledge of the volume and especially the radius, the appropriately sized filter sizes the gaseous precursor droplets to the appropriate diameter sphere.

A representative gaseous precursor may be used to form a microsphere of defined size, for example, 10 microns diameter. In this example, the microsphere is formed in the bloodstream of a human being, thus the typical temperature would be 37° C. or 310° K. At a pressure of 1 atmosphere and using the equation in (A), $7.54\times10^{-17}$ moles of gaseous precursor would be required to fill the volume of a 10 micron diameter microsphere.

Using the above calculated amount of gaseous precursor, and 1-fluorobutane, which possesses a molecular weight of 76.11, a boiling point of 32.5° C. and a density of 6.7789 grams/$mL^{-1}$ at 20° C., further calculations predict that $5.74\times10^{-15}$ grams of this precursor would be required for a 10 micron microsphere. Extrapolating further, and armed with the knowledge of the density, equation (B) further predicts that $8.47\times10^{-16}$ mLs of liquid precursor are necessary to form a microsphere with an upper limit of 10 microns.

Finally, using equation (C), an emulsion of lipid droplets with a radius of 0.0272 microns or a corresponding diameter of 0.0544 microns need be formed to make a gaseous precursor-filled microsphere with an upper limit of a 10 micron microsphere.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment of the present invention may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be explained by physical methods as well. When substances, solid or liquid, herein referred to as solutes, are dissolved in a solvent, such as water based buffers for example, the freezing point is lowered by an amount that is dependent upon the composition of the solution. Thus, as defined by Wall, one can express the freezing point depression of the solvent by the following:

$$Inx_a=In(1-x_b)=\Delta H_{fus}/R(1/T_o-1/T)$$

where:

$x_a$=mole fraction of the solvent $x_b$=mole fraction of the solute $\Delta H_{fus}$=heat of fusion of the solvent $T_o$=Normal freezing point of the solvent The normal freezing point of the solvent results. If $x_b$ is small relative to $x_a$, then the above equation may be rewritten:

$$x^b=\Delta H_{fus}/R[T-T_o/T_oT]\approx\Delta H_{fus}\Delta T/RT_o{}^2$$

The above equation assumes the change in temperature $\Delta T$ is small compared to $T_2$. The above equation can be simplified further assuming the concentration of the solute (in moles per thousand grams of solvent) can be expressed in terms of the molality, m. Thus, $$X_b = m/[m + 1000/m_a] = mMa/1000$$

where:
Ma=Molecular weight of the solvent, and
m=molality of the solute in moles per 1000 grams.
Thus, substituting for the fraction $x_b$:

$$\Delta T = [M_a R T_o^2 / 1000 \Delta H_{fus}] m$$

or $\Delta T = K_f m$, where $$K_f = M_a R T_o^2 / 1000 \Delta H_{fus}$$

$K_f$ is referred to as the molal freezing point and is equal to 1.86 degrees per unit of molal concentration for water at one atmosphere pressure. The above equation may be used to accurately determine the molal freezing point of gaseous-precursor filled microsphere solutions of the present invention.

Hence, the above equation can be applied to estimate freezing point depressions and to determine the appropriate concentrations of liquid or solid solute necessary to depress the solvent freezing temperature to an appropriate value.

Methods of preparing the temperature activated gaseous precursor-filled liposomes include:

vortexing an aqueous suspension of gaseous precursor-filled liposomes of the present invention; variations on this method include optionally heating an aqueous suspension of gaseous precursor and lipid, optionally venting the vessel containing the suspension, optionally shaking or permitting the gaseous precursor liposomes to form spontaneously and cooling down the gaseous precursor-filled liposome suspension, optionally autoclaving (at a temperature of about 100° C. to about 130° C.) may optionally be added as a first step, as filtering replaces the need for autoclaving; optionally extruding an aqueous suspension of gaseous precursor and lipid through a filter of about 0.22 μm, alternatively, filtering may be performed during in vivo administration of the resulting liposomes such that a filter of about 0.22 μm is employed;

a microemulsification method whereby an aqueous suspension of gaseous precursor-filled liposomes of the present invention are emulsified by shaking or vortexing and heated to form microspheres prior to administration to a patient; and forming a gaseous precursor in lipid suspension by heating, and/or shaking, whereby the less dense gaseous precursor-filled microspheres float to the top of the solution by expanding and displacing other microspheres in the vessel and venting the vessel to release air.

Freeze drying is useful to remove water and organic materials from the lipids prior to the shaking gas instillation method. Drying-gas instillation method may be used to remove water from liposomes. By pre-entrapping the gaseous precursor in the dried liposomes (i.e. prior to drying) after warming, the gaseous precursor may expand to fill the liposome. Gaseous precursors can also be used to fill dried liposomes after they have been subjected to vacuum. As the dried liposomes are kept at a temperature below their gel state to liquid crystalline temperature the drying chamber can be slowly filled with the gaseous precursor in its gaseous state, e.g. perfluorobutane can be used to fill dried liposomes composed of dipalmitoylphosphatidylcholine (DPPC) at temperatures between 3° C. (the boiling point of perfluorobutane) and below 40° C., the phase transition temperature of the lipid. In this case, it would be most preferred to fill the liposomes at a temperature about 4° C. to about 5° C.

The gaseous precursor-filled microspheres can be used in conjunction with such clinical techniques as ultrasound, microwave radiation, or electromagnetic energy to generate liquid to gas conversion of the precursor, thereby mediating site selected drug delivery in vivo. By selecting a gaseous precursor with a boiling point above 37° C., the gaseous precursor-filled microsphere may be formulated as a stable nanoparticle with a long blood half-life, or, alternatively, target it to the tissue of interest. The desired ultrasound, microwave, or electromagnetic energy may then be focused to the target tissue and cause the gaseous precursor to convert to the gaseous phase. In so doing, pharmaceuticals and bioactive materials incorporated into the coating or stabilizing emulsion in the gaseous nanoparticle will be released as the microsphere expands more than one time the original size in vivo. A good example of an appropriate gaseous precursor is 2-methyl-2-butene which has a boiling point of 38.6° C. Additionally, these gaseous precursors may be particularly efficient in solubilizing more hydrophobic pharmaceuticals, for example, anthracycline antibiotics, which are difficult to solubilize in aqueous-based formulation.

As one skilled in the art would recognize, this process of microemulsification, for example, gas-filled microsphere stabilization from temperature activated gaseous precursors, can be utilized to produce a wide variety of improved stabilized gaseous microsphere products.

By selecting the appropriate solvent system and gaseous precursor, as well as stabilizing agents, microspheres improved over conventional products can be prepared. The solvent system can be selected to provide a ligand medium for suspension of the gaseous precursor. As an example 20% propylene glycol miscible in buffered saline exhibits a freezing point depression well below the freezing point of water alone. By increasing the amount of propylene glycol or adding materials such as sodium chloride, the freezing point can be depressed even further. Depression of the freezing point of the solvent system is important in that this allows us to use gaseous precursors which would undergo liquid to gas phase transitions at temperatures below 0° C.

An additional advantage of using these gaseous precursors is that they are more stable in vivo than non-precursor gases such as air and nitrogen. Because gases derived from these precursors are generally less diffusible and less soluble in aqueous media than air or nitrogen, the resultant contrast agents are generally more stable than traditional gas or non-precursor based contrast agents.

Gaseous precursors which may be activated by temperature may be useful in the present invention. Table I lists examples of gaseous precursors which undergo phase transitions from liquid to gaseous states at close to normal body temperature (37° C.) and the size of the emulsified droplets that would be required to form a microsphere having a size of 10 microns. The list is composed of potential gaseous precursors that may be used to form temperature activated gaseous precursor-containing liposomes of a defined size. The list should not be construed as being limiting by any means, as to the possibilities of gaseous precursors for the present invention.

TABLE I

Physical Characteristics of Gaseous Precursors and
Diameter of Emulsified Droplet to Form a 10 μm Microsphere

| Compound | Molecular Weight | Boiling Point (° C.) | Density | Diameter (μm) of emulsified droplet to make 10 micron microsphere |
|---|---|---|---|---|
| perfluoro pentane | 288.04 | 57.73 | 1.7326 | 0.00549 |
| 1 fluorobutane | 76.11 | 32.5 | 6.7789 | .0544 |
| 2-methyl butane (isopentane) | 72.15 | 27.8 | 0.6201 | .01474 |
| 2-methyl 1-butene | 70.13 | 31.2 | 0.6504 | .01464 |
| 2-methyl-2-butene | 70.13 | 38.6 | 0.6623 | .01456 |
| 1-butene-3-yne-2-methyl | 66.10 | 34.0 | 0.6801 | .01472 |
| 3-methyl-1-butyne | 68.12 | 29.5 | 0.6660 | .01467 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |
| docecafluoro pentane | 288.05 | 29.5 | 1.664 | 2.9 |
| octafluoro-2-butene | 200.04 | 1.2 | 1.5297 | 2.8 |
| perfluoro cyclobutane | 200.04 | −5.8 | 1.48 | 2.8 |
| octafluoro cyclopentene | 212.05 | 27 | 1.58 | 2.7 |
| perfluoro cyclobutene | 162 | 5 | 1.602 | 2.5 |
| perfluoro methane | 88.00 | −129 | 3.034 | 3.3 |
| perfluoro ethane | 138.01 | −79 | 1.590 | 1.0 |
| perfluoro butane | 238.03 | 3.96 | 1.6484 | 2.8 |

*Source: Chemical Rubber Company Handbook of Chemistry and Physics Robert C. Weast and David R. Lide, eds. CRC Press, Inc. Boca Raton, Florida. (1989–1990).

Examples of gaseous precursors are by no means limited to Table 1. In fact, for a variety of different applications, virtually any liquid can be used to make gaseous precursors so long as it is capable of undergoing a phase transition to the gas phase upon passing through the appropriate activation temperature. Examples of gaseous precursors that may be used include, and are by no means limited to, the following: hexafluoro acetone; isopropyl acetylene; allene; tetrafluoroallene; boron trifluoride; 1,2-butadiene; 1,3-butadiene; 1,3-butadiene; 1,2,3-trichloro, 2-fluoro-1,3-butadiene; 2-methyl,1,3 butadiene; hexafluoro-1,3-butadiene; butadiyne; 1-fluoro-butane; 2-methyl-butane; decafluoro butane; 1-butene; 2-butene; 2-methy-1-butene; 3-methyl-1-butene; perfluoro-1-butene; perfluoro-1-butene; perfluoro-2-butene; 1,4-phenyl-3-butene-2-one; 2-methyl-1-butene-3-yne; butyl nitrate; 1-butyne; 2-butyne; 2-chloro-1,1,1,4,4,4-hexafluoro-butyne; 3-methyl-1-butyne; perfluoro-2-butyne; 2-bromo-butyraldehyde; carbonyl sulfide; crotononitrile; cyclobutane; methyl-cyclobutane; octafluoro-cyclobutane; perfluoro-cyclobutene; 3-chloro-cyclopentene; perfluoro ethane; perfluoro propane; perfluoro butane; perfluoro pentane; perfluoro hexane; cyclopropane; 1,2-dimethyl-cyclopropane; 1,1-dimethyl cyclopropane; 1,2-dimethyl cyclopropane; ethyl cyclopropane; methyl cyclopropane; diacetylene; 3-ethyl-3-methyl diaziridine; 1,1,1-trifluorodiazoethane; dimethyl amine; hexafluorodimethyl amine; dimethylethylamine; -bis-(Dimethyl phosphine)amine; 2,3-dimethyl-2-norbornane; perfluorodimethylamine; dimethyloxonium chloride; 1,3-dioxolane-2-one; perfluorocarbons such as and not limited to 4-methyl,1,1,1,2-tetrafluoro ethane; 1,1,1-trifluoroethane; 1,1,2,2-tetrafluoroethane; 1,1,2-trichloro-1,2,2-trifluoroethane; 1,1 dichloroethane; 1,1-dichloro-1,2,2,2-tetrafluoro ethane; 1,2-difluoro ethane; 1-chloro-1,1,2,2,2-pentafluoro ethane; 2-chloro, 1,1-difluoroethane; 1-chloro-1,1,2,2-tetrafluoro ethane; 2-chloro, 1,1-difluoroethane; chloroethane; chloropentafluoro ethane; dichlorotrifluoroethane; fluoro-ethane; hexafluoro-ethane; nitro-pentafluoro ethane; nitroso-pentafluoro ethane; perfluoro ethane; perfluoro ethylamine; ethyl vinyl ether; 1,1-dichloro ethylene; 1,1-dichloro-1,2-difluoro ethylene; 1,2-difluoro ethylene; Methane; Methane-sulfonyl chloride-trifluoro; Methane-sulfonyl fluoride-trifluoro; Methane-(pentafluorothio) trifluoro; Methane-bromo difluoro nitroso; Methane-bromo fluoro; Methane-bromo chloro-fluoro; Methanebromo-trifluoro; Methane-chloro difluoro nitro; Methane-chloro dinitro; Methanechloro fluoro; Methane-chloro trifluoro; Methane-chloro-difluoro; Methane dibromo difluoro; Methane-dichloro difluoro; Methane-dichloro-fluoro; Methanedifluoro; Methane-difluoro-iodo; Methane-disilano; Methane-fluoro; Methaneiodo; Methane-iodo-trifluoro; Methane-nitro-trifluoro; Methane-nitroso-trifluoro; Methane-tetrafluoro; Methane-trichlorofluoro; Methane-trifluoro; Methanesulfenylchloride-trifluoro; 2-Methyl butane; Methyl ether; Methyl isopropyl ether; Methyl lactate; Methyl nitrite; Methyl sulfide; Methyl vinyl ether; Neon; Neopentane; Nitrogen ($N_2$); Nitrous oxide; 1,2,3-Nonadecane tricarboxylic acid-2-hydroxytrimethylester; 1-Nonene-3-yne; Oxygen ($O_2$); 1, 4-Pentadiene; n-Pentane; Pentane-perfluoro; 2-Pentanone-4-amino-4-methyl; 1-Pentene; 2-Pentene [cis]; 2-Pentene (trans); 1-Pentene-3-bromo; 1-Pentene-perfluoro; Phthalic acid-tetrachloro; Piperidine-2,3,6-trimethyl; Propane, Propane-1,1,1,2,2,3-hexafluoro; Propane-1,2-epoxy; Propane-2,2 difluoro; Propane 2-amino, Propane-2-chloro; Propane-heptafluoro-1-nitro; Propane-heptafluoro-1-nitroso; Propane-perfluoro; Propene; Propyl-1,1,1,2,3,3-hexafluoro-2,3 dichloro; Propylene-1-chloro; Propylenechloro-(trans); Propylene-2-chloro; Propylene-3-fluoro; Propylene-perfluoro; Propyne; Propyne-3,3,3-trifluoro; Styrene-3-fluoro; Sulfur hexafluoride; Sulfur (di)-decafluoro(S2F10); Toluene-2,4-diamino; Trifluoroacetonitrile; Trifluoromethyl peroxide; Trifluoromethyl sulfide; Tungsten hexafluoride; Vinyl acetylene; Vinyl ether; Xenon; Nitrogen; air; and other ambient gases.

Perfluorocarbons are the preferred gases of the present invention, fluorine gas, perfluoromethane, perfluoroethane, perfluorobutane, perfluoropentane, perfluorohexane; even more preferably perfluoroethane, perfluoropentane, perfluoropropane, and perfluorobutane; most preferably perfluoropentane, perfluoropropane, and perfluorobutane as the more inert perfluorinated gases are less toxic.

The gases identified above are more stable in vivo than non-precursor gases such as air and nitrogen. Because gases derived from these precursors are generally less diffusible and less soluble in aqueous media than air or nitrogen, the resultant therapeutic delivery systems generally more stable than traditional gas or non-precursor based contrast agents.

By "gas-filled", as used herein, it is meant microspheres having an interior volume that is at least about 10% gas, preferably at least about 25% gas, more preferably at least about 50% gas, even more preferably at least about 75% gas, and most preferably at least about 90% gas. It will be understood by one skilled in the art, once armed with the present disclosure, that a gaseous precursor may also be used, followed by activation to form a gas.

Various biocompatible gases may be employed in the gaseous precursor-filled microspheres of the present invention. Such gases include air, hydrogen, nitrogen, carbon dioxide, oxygen, argon, fluorine, xenon, neon, helium, or any and all combinations thereof. Other suitable gases will be apparent to those skilled in the art once armed with the present disclosure.

The microspheres of the present invention are preferably comprised of an impermeable material. An impermeable material is defined as a material that does not permit the passage of a substantial amount of the contents of the microsphere in typical storage conditions or in use before ultrasound induced release occurs. Typical storage conditions are, for example, a non-degassed aqueous solution of 0.9% NaCl maintained at 4° C. for 48 hours. Substantial as used in connection with impermeability is defined as greater than about 50% of the contents, the contents being both the gaseous precursor and the therapeutic. Preferably, no more than about 25% of the gaseous precursor, gas, and the therapeutic are released, more preferably, no more than about 10% of the gaseous precursor, gas, and the therapeutic are released during storage, and most preferably no more than about 1% of the gaseous precursor, gas, and therapeutic are released. The temperature of storage is preferably below the phase transition temperature of the material forming the microspheres and below the activation temperature of the gaseous precursor. However, the gaseous precursor may be activated during manufacture or storage.

At least in part, the gas impermeability of gaseous precursor-filled liposomes has been found to be related to the gel state to liquid crystalline state phase transition temperature. By "gel state to liquid crystalline state phase transition temperature", it is meant the temperature at which a lipid bilayer will convert from a gel state to a liquid crystalline state. See, for example, Chapman et al., *J. Biol. Chem.* 1974, 249, 2512–2521. It is believed that, generally, the higher gel state to liquid crystalline state phase transition temperature, the more gas impermeable the liposomes are at a given temperature. See Table II below and Derek Marsh, *CRC Handbook of Lipid Bilayers* (CRC Press, Boca Raton, Fla. 1990), at p. 139 for main chain melting transitions of saturated diacyl-sn-glycero-3-phosphocholines. However, it should also be noted that a lesser degree of energy can generally be used to release a therapeutic compound from gaseous precursor-filled liposomes composed of lipids with a lower gel state to liquid crystalline state phase transition temperature. Where the gel state to liquid crystalline state phase transition temperature of the lipid employed is higher than room temperature, the temperature of the container may be regulated, for example, by providing a cooling mechanism to cool the container holding the lipid solution.

Since gaseous precursors (e.g. perfluorobutane) are less soluble and diffusible than other gases, such as air, they tend to be more stable when entrapped in liposomes even when the liposomes are composed of lipids in the liquid-crystalline state. Small liposomes composed of liquid-crystalline state lipid such as egg phosphatidyl choline may be used to entrap a nanodroplet of perfluorobutane. For example, lipid vesicles with diameters of about 30 nm to about 50 nm may be used to entrap nanodroplets of perfluorobutane with mean diameter of about 25 nm. After temperature activated conversion, the precursor filled liposomes will create microspheres of about 10 microns in diameter. The lipid in this case, serves the purpose of defining the size of the microsphere via the small liposome. The lipids also serve to stabilize the resultant microsphere size. In this case, techniques such as microemulsification are preferred for forming the small liposomes which entrap the precursor. A microfluidizer (Microfluidics, Newton, Mass.) is particularly useful for making an emulsion of small liposomes which entrap the gaseous precursor.

TABLE II

Saturated Diacyl-sn-Glycero-3-Phosphocholines: Main Chain Gel State to Liquid Crystalline State Phase Transition Temperatures

| # Carbons in Acyl Chains | Main Phase Transition Temperature (° C.) |
| --- | --- |
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984).

In certain preferred embodiments, the phase transition temperature of the material forming the microsphere is greater than the internal body temperature of the patient to which they are administered. For example, microspheres having a phase transition temperature greater than about 37° C. are preferred for administration to humans. In general, microspheres having a phase transition temperature greater than about 20° C. are preferred.

In preferred embodiments, the microspheres of the invention are stable, stability being defined as resistance to rupture from the time of formation until the application of ultrasound. The materials, such as lipids, used to construct the microspheres may be chosen for stability. For example, gaseous precursor-filled liposomes composed of DSPC (distearoylphosphatidylcholine) are more stable than gaseous precursor-filled liposomes composed of DPPC (dipalmitoylphosphatidyl-choline) and that these in turn are more stable than gaseous precursor-filled liposomes composed of egg phosphatidylcholine (EPC). Preferably, no more than about 50% of the microspheres rupture from the time of formation until the application of ultrasound, more preferably, no more than about 25% of the microspheres rupture, even more preferably, no more than about 10% of the microspheres, and most preferably, no more than about 1% of the microspheres.

In addition, it has been found that the gaseous precursor-filled liposomes of the present invention can be stabilized with lipids covalently linked to polymers of polyethylene glycol, commonly referred to as PEGylated lipids. It has also been found that the incorporation of at least a small amount of negatively charged lipid, or a lipid having a net negative charge, into any liposome membrane, although not required, is beneficial to providing liposomes that do not have a propensity to rupture by fusing together. By at least a small amount, it is meant about 1 to about 10 mole percent of the total lipid. Suitable negatively charged lipids will be readily apparent to those skilled in the art, and include, for example, phosphatidylserine and fatty acids. Most preferred for ability to rupture on application of resonant frequency ultrasound, echogenicity and stability are liposomes prepared from dipalmitoylphosphatidylcholine.

Further, the microspheres of the invention are preferably sufficiently stable in the vasculature such that they withstand recirculation. The gaseous precursor-filled microspheres may be coated such that uptake by the reticuloendothelial system is minimized. Useful coatings include, for example, gangliosides, glucuronate, galacturonate, guluronate, polyethyleneglycol, polypropylene glycol, polyvinylpyrrolidone, polyvinylalcohol, dextran, starch, phosphorylated and sulfonated mono, di, tri, oligo and polysaccharides and albumin. The microspheres may also be coated for purposes such as evading recognition by the immune system.

In preferred embodiments, at least about 50%, preferably, at least about 75%, more preferably at least about 90% and most preferably, about 100% of the therapeutic and gas contents of the microspheres remain with the microsphere, because of their impermeability until they reach the internal region of the patient to be targeted and ultrasound is applied.

Further, the materials used to form the microspheres should be biocompatible. Biocompatible materials are defined as non-toxic to a patient in the amounts in which they are administered, and preferably are not disease-producing, and most preferably are harmless.

The material used to form the microspheres is also preferably flexible. Flexibility, as defined in the context of gaseous precursor-filled microspheres, is the ability of a structure to alter its shape, for example, in order to pass through an opening having a size smaller than the microsphere. Due to flexible lipid membranes they have the ability to change diameter and stiffness with pressure. The reflected ultrasonic signals may therefore be used non-invasively for measuring pressures inside the body.

Liposomes are a preferred embodiment of this invention since they are highly useful for entrapping gas. Additionally, gaseous precursor-filled liposomes are preferred due to their biocompatibility and the ability to easily accommodate lipophilic therapeutic compounds that will easily cross cell membranes after the liposomes are ruptured. One skilled in the art, once armed with the present disclosure, would recognize that particular lipids may be chosen for the intended use.

The yield of gas-filled lipid spheres produced from gaseous precursors increases when prepared from hydrated multilamellar lipid suspensions as opposed to large unilamellar vesicles or dried lipid. Gas-filled microspheres prepared from lipid suspensions have a decreased amount of unhydrated lipid in the final product. Unhydrated lipid appears as amorphous clumps of non-uniform size and is undesirable. The multilamellar lipid suspensions may be autoclaved as a terminal sterilization step without any compromise in gaseous precursor-filled microsphere production. Autoclaving does not change the size of the lipid particles and does not decrease the ability of the lipid suspensions to entrap gaseous precursors or gas. Sterile vials or syringes may be filled with the lipid suspensions and then sterilized in situ by autoclave. Gas may be instilled into the lipid suspensions after autoclave in situ within the sterile containers via manual agitation, immediately prior to use, for example, with vortexing, pressurization or other mechanical agitation, such as a shaker table.

Provided that the circulation half-life of the microspheres is sufficiently long, the microspheres will generally pass through the target tissue as they pass through the body. By focusing the rupture inducing sound waves on the selected tissue to be treated, the therapeutic will be released locally in the target tissue. As a further aid to targeting, antibodies, carbohydrates, peptides, glycopeptides, glycolipids, lectins, glycoconjugates, and synthetic and natural polymers, such as and not limited to polyethylene glycol, polyvinylpyrrolidone, polyvinylalcohol, which may be incorporated onto the surface via alkylation, acylation, sterol groups or derivatized head groups of phospholipids such as dioleoylphosphatidylethanolamine (DOPE), dipalmitoylphosphatidylethanolamine (DPPE), or disteroylphosphatidylethanolamine (DSPE), may also be incorporated into the surface of the microspheres.

Where lipid material is used to create the microspheres, thus forming a liposome, a wide variety of lipids may be utilized in the construction of the microspheres. The materials which may be utilized in preparing liposomes include any of the materials or combinations thereof known to those skilled in the art as suitable for liposome preparation. The lipids used may be of either natural or synthetic origin. The particular lipids are chosen to optimize the desired properties, e.g., short plasma half-life versus long plasma half-life for maximal serum stability.

The lipid in the gaseous precursor-filled liposomes may be in the form of a single bilayer or a multilamellar bilayer, and are preferably multilamellar.

Lipids which may be used to create liposome microspheres include but are not limited to: lipids such as fatty acids, lysolipids, phosphatidylcholine with both saturated and unsaturated lipids including dioleoylphosphatidylcholine; dimyristoylphosphatidylcholine; dipentadecanoylphosphatidylcholine, dilauroylphosphatidylcholine, dioleoylphosphatidylcholine, dipalmitoylphosphatidylcholine; distearoylphosphatidylcholine; phosphatidylethanolamines such as dioleoylphosphatidylethanolamine; phosphatidylserine; phosphatidylglycerol; phosphatidylinositol, sphingolipids such as sphingomyelin; glycolipids such as ganglioside GM1 and GM2; glucolipids; sulfatides; glycosphingolipids; phosphatidic acid; palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol, cholesterol sulfate and cholesterol hemisuccinate; tocopherol hemisuccinate, lipids with ether and ester-linked fatty acids, polymerized lipids, diacetyl phosphate, stearylamine, cardiolipin, phospholipids with short chain fatty acids of 6–8 carbons in length, synthetic phospholipids with asymmetric acyl chains (e.g., with one acyl chain of 6 carbons and another acyl chain of 12 carbons), 6-(5-cholesten-3β-yloxy)-1-thio-β-D-galactopyranoside, digalactosyldiglyceride, 6-(5-cholesten-3β-yloxy)hexyl-6-amino-6-deoxy-1-thio-β-D-galactopyranoside, 6-(5-cholesten-3β-yloxy)hexyl-6-amino-6-deoxyl-1-thio-α-D-mannopyranoside, 12-(((7'-diethylaminocoumarin-3-yl) carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoylphosphatidylethanolamine; 1,2-dioleoyl-sn-glycerol;1,2-dipalmitoyl-sn-3-succinylglycerol; 1,3-dipalmitoyl-2-succinylglycerol;1-hexadecyl-2-palmitoylglycerophosphoethanolamine and palmitoylhomocysteine, and/or combinations thereof. The liposomes may be formed as monolayers or bilayers and may or may not have a coating.

Lipids bearing hydrophilic polymers such as polyethyleneglycol (PEG), including and not limited to PEG 2,000 MW, 5,000 MW, and PEG 8,000 MW, are particularly useful for improving the stability and size distribution of the gaseous precursor-containing liposomes. Various different mole ratios of PEGylated lipid, dipalmitoylphosphatidylethanolamine (DPPE) bearing PEG 5,000 MW, for example, are also useful; 8 mole percent DPPE is preferred. A preferred product which is highly useful for entrapping gaseous precursors contains 83 mole percent DPPC, 8 mole percent DPPE-PEG 5,000 MW and 5 mole percent dipalmitoylphosphatidic acid.

In addition, examples of compounds used to make mixed systems include, but by no means are limited to lauryltrimethylammonium bromide (dodecyl-), cetyltrimethylammonium bromide (hexadecyl-), myristyltrimethylammonium bromide (tetradecyl-), alkyldimethylbenzylammonium chloride (alkyl=C12,C14,C16), benzyldimethyldodecylammonium bromide/chloride, benzyldimethylhexadecylammonum bromide/chloride, benzyldimethyltetradecylammonium bromide/chloride, cetyldimethylethylammonium bromide/chloride, or cetylpyridinium bromide/chloride. Likewise perfluorocarbons such as pentafluoro octadecyl iodide, perfluorooctylbromide (PFOB), perfluorodecalin, perfluorododecalin, perfluorooctyliodide, perfluorotripropylamine, and perfluorotributylamine. The perfluorocarbons may be entrapped in liposomes or stabilized in emulsions as is well know in the art such as U.S. Pat. No. 4,865,836. The above examples of lipid suspensions may also be sterilized via autoclave without appreciable change in the size of the suspensions. A preferred product of the present invention incorporates lipid as a mixed solvent system in a ratio of 8:1:1 or 9:1:1 normal saline:glycerol:propylene glycol.

If desired, either anionic or cationic lipids may be used to bind anionic or cationic pharmaceuticals. Cationic lipids may be used to bind DNA and RNA analogues with in or on the surface of the gaseous precursor-filled microsphere. A variety of cationic lipids such as DOTMA, N-[1-(2,3-dioleoyloxy)propyl]-N,N,N-trimethylammoium chloride; DOTAP, 1,2-dioleoyloxy-3-(trimethylammonio)propane; and DOTB, 1,2-dioleoyl-3-(4'-trimethyl-ammonio) butanoyl-sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the microsphere. Preferably, this non-cationic lipid is dipalmitoylphosphatidylcholine, dipalmitoylphosphatidylethanolamine or dioleoylphosphatidylethanolamine. In lieu of cationic lipids as described above, lipids bearing cationic polymers such as polylysine or polyarginine may also be used to construct the microspheres and afford binding of a negatively charged therapeutic, such as genetic material, to the outside of the microspheres. As an example, anionic lipids may consist of but are by no means limited to sodium dodecyl sulfate, steraric acid, palmitic acid, phosphatidic acid, and cholesterol sulfate.

Other useful lipids or combinations thereof apparent to those skilled in the art which are in keeping with the spirit of the present invention are also encompassed by the present invention. For example, carbohydrate-bearing lipids may be employed for in vivo targeting, as described in U.S. Pat. No. 4,310,505, the disclosures of which are hereby incorporated herein by reference, in their entirety.

The most preferred lipids are phospholipids, preferably DPPC and DSPC, and most preferably DPPC.

Saturated and unsaturated fatty acids that may be used to generate gaseous precursor-filled microspheres preferably include, but are not limited to molecules that have between 12 carbon atoms and 22 carbon atoms in either linear or branched form. Hydrocarbon groups consisting of isoprenoid units and/or prenyl groups may be used as well. Examples of saturated fatty acids that may be used include, but are not limited to, lauric, myristic, palmitic, and stearic acids. Examples of unsaturated fatty acids that may be used include, but are not limited to, lauroleic, physeteric, myristoleic, palmitoleic, petroselinic, and oleic acids. Examples of branched fatty acids that may be used include, but are not limited to, isolauric, isomyristic, isopalmitic, isostearic acids, isoprenoids, and prenyl groups.

Generally, one or more emulsifying or stabilizing agents are included with the gaseous precursors to formulate the therapeutic containing delivery system. The purpose of these emulsifying/stabilizing agents is two-fold. Firstly, these agents help to maintain the size of the gaseous precursor-filled microsphere. As noted above, the size of these microspheres will generally affect the size of the resultant gas-filled microspheres. Secondly the emulsifying and stabling agents may be used to coat or stabilize the microsphere which results from the precursor. Stabilization of contrast agent-containing microspheres is desirable to maximize the in vivo contrast effect. Although stabilization of the microsphere is preferred this is not an absolute requirement. Because the gas-filled microspheres resulting from these gaseous precursors are more stable than air, they may still be designed to provide useful contrast enhancement, for example, they pass through the pulmonary circulation following peripheral venous injection, even when not specifically stabilized by one or more coating or emulsifying agents. One or more coating or stabilizing agents is preferred however, as are flexible stabilizing materials. Gas microspheres stabilized by albumin and other proteins are less effective as these stabilizing coating are more brittle and are easily broken during pressure changes, for example, by passage through the heart and arteries. Liposomes prepared using aliphatic compounds are preferred as microspheres stabilized with these compounds are much more flexible and stable to pressure changes.

Solutions of lipids or gaseous precursor-filled liposomes may be stabilized, for example, by the addition of a wide variety of viscosity modifiers, including, but not limited to carbohydrates and their phosphorylated and sulfonated derivatives; polyethers, preferably with molecular weight ranges between 400 and 8000; di- and trihydroxy alkanes and their polymers, preferably with molecular weight ranges between 800 and 8000. Glycerol propylene glycol, polyethylene glycol, polyvinyl pyrrolidone, and polyvinyl alcohol may also be useful as stabilizers in the present invention. Particles which are porous or semi-solid such as hydroxyapatite, metal oxides and coprecipitates of gels, e.g. hyaluronic acid with calcium may be used to formulate a center or nidus to stabilize the gaseous precursors. Of course, solid particles such as limestone, zeolites, and other particles would generally be considered unsuitable for injection into the intravascular space, however, they may be quite useful for forming a nidus for the entrapment of the gaseous precursors and function as effective gastrointestinal contrast agent, e.g. for MRI or computed tomography.

Emulsifying and/or solubilizing agents may also be used in conjunction with lipids or liposomes. Such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer, peanut oil, palmitic acid, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax. All lipids with perfluoro fatty acids as a component of the lipid in lieu of the saturated or unsaturated hydrocarbon fatty acids found in lipids of plant or animal origin may be used. Suspending and/or viscosity-increasing agents that may be used with lipid or liposome solutions include, but are not limited to, acacia, agar, alginic acid, aluminum monostearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

Any of a variety of therapeutics may be encapsulated in the microspheres. By therapeutic, as used herein, it is meant an agent having a beneficial effect on the patient. As used herein, the term therapeutic is synonymous with contrast agents and drugs.

It is believed that nanoparticles and emulsions of certain precursors are particularly effective at accumulating in ischemic and diseased tissue. Such precursors can be used for detecting ischemic and diseased tissue via ultrasound and also for delivering drugs to these tissues. By coentrapping drugs with the emulsions or nanoparticles comprising the gaseous precursors, said drugs can then be delivered to the diseased tissues. For example, emulsions of sulfur hexafluoride, hexafluoropropylene, bromochloropluoromethane, octafluoropropane, 1,1 dichloro, fluoro ethane, hexa flurooethane, hexafluoro-2-butyne, perfluoropentane, perfluorobutane, octafluoro-2-butene or hexafluorobuta-1,3-diene or octafluorocyclopentene (27° C.) can be used to deliver drugs such as cardiac glycosides, angiogenic factors and vasoactive compounds to ischemic regions of the myocardium. Similarly, emulsions of the above precursors may also be used to deliver antisense DNA or chemotherapeutics to tumors. It is postulated that subtle changes in temperature, pH, and oxygen tension are responsible for the accumulation of certain precursors preferentially by diseased and ischemic tissues. These precursors can be used as delivery vehicles or in ultrasound for drug delivery.

Suitable therapeutics include, but are not limited to paramagnetic gases, such as atmospheric air, which contains traces of oxygen 17, or paramagnetic ions such as $Mn^{+2}$, $Gd^{+2}$, $Fe^{+3}$, as well as superparamagnetic particles (ferrites, iron oxides $Fe_3O_4$) and may thus be used as susceptibility contrast agents for magnetic resonance imaging (MRI), radioopaque metal ions, such as iodine, barium, bromine, or tungsten, for use as x-ray contrast agents, gases from quadrupolar nuclei, may have potential for use as Magnetic Resonance contrast agents, antineoplastic agents, such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, arabinosyl, hydroxyurea, procarbazine, and dacarbazine; mitotic inhibitors such as etoposide and the vinca alkaloids, radiopharmaceuticals such as radioactive iodine and phosphorus products; hormones such as progestins, estrogens and antiestrogens; anti-helmintics, antimalarials, and anti-tuberculosis drugs; biologicals such as immune serums, antitoxins and antivenins; rabies prophylaxis products; bacterial vaccines; viral vaccines; aminoglycosides; respiratory products such as xanthine derivatives theophylline and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), subunits of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, cyclosporins, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and α-tocopherol; peptides, such as manganese super oxide dismutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT, DDI, Foscarnet, or Zidovudine), ribavirin and vidarabine monohydrate (adenine arabinoside, ara-A); anti-anginals such as diltiazem, nifedipine, verapamil, erythritol tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

In certain preferred embodiments, the therapeutic is a monoclonal antibody, such as a monoclonal antibody capable of binding to melanoma antigen.

Other preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers.

Examples of genetic therapeutics that may be applied using the microspheres of the present invention include DNA encoding at least a portion of an HLA gene, DNA encoding at least a portion of dystrophin, DNA encoding at least a portion of CFTR, DNA encoding at least a portion of IL-2, DNA encoding at least a portion of TNF, an antisense oligonucleotide capable of binding the DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, Science 258, 744–746, 1992.

If desired, more than one therapeutic may be applied using the microspheres. For example, a single microsphere may contain more than one therapeutic or microspheres containing different therapeutics may be co-administered. By way of example, a monoclonal antibody capable of binding to melanoma antigen and an oligonucleotide encoding at least a portion of IL-2 may be administered at the same time. The phrase "at least a portion of," as used herein, means that the entire gene need not be represented by the oligonucleotide, so long as the portion of the gene represented provides an effective block to gene expression.

Similarly, prodrugs may be encapsulated in the microspheres, and are included within the ambit of the term therapeutic, as used herein. Prodrugs are well known in the art and include inactive drug precursors which, when exposed to high temperature, metabolizing enzymes, cavitation and/or pressure, in the presence of oxygen or otherwise, or when released from the microspheres, will form active drugs. Such prodrugs can be activated in the method of the invention, upon the application of ultrasound to the prodrug-containing microspheres with the resultant cavitation, heating, pressure, and/or release from the microspheres. Suitable prodrugs will be apparent to those skilled in the art, and are described, for example, in Sinkula et al., *J. Pharm. Sci.* 1975 64, 181–210, the disclosure of which are hereby incorporated herein by reference in its entirety.

Prodrugs, for example, may comprise inactive forms of the active drugs wherein a chemical group is present on the prodrug which renders it inactive and/or confers solubility or some other property to the drug. In this form, the prodrugs are generally inactive, but once the chemical group has been cleaved from the prodrug, by heat, cavitation, pressure, and/or by enzymes in the surrounding environment or otherwise, the active drug is generated. Such prodrugs are well described in the art, and comprise a wide variety of drugs bound to chemical groups through bonds such as esters to short, medium or long chain aliphatic carbonates, hemiesters of organic phosphate, pyrophosphate, sulfate, amides, amino acids, azo bonds, carbamate, phosphamide, glucosiduronate, N-acetylglucosamine and β-glucoside.

Examples of drugs with the parent molecule and the reversible modification or linkage are as follows: convallatoxin with ketals, hydantoin with alkyl esters, chlorphenesin with glycine or alanine esters, acetaminophen with caffeine complex, acetylsalicylic acid with THAM salt, acetylsalicylic acid with acetamidophenyl ester, naloxone with sulfate ester, 15-methylprostaglandin $F_{2\alpha}$ with methyl ester, procaine with polyethylene glycol, erythromycin with alkyl esters, clindamycin with alkyl esters or phosphate esters, tetracycline with betaine salts, cephalosporins including 7-acylaminocephalosporins with ring-substituted acyloxybenzyl esters, nandrolone with phenylproprionate decanoate esters, estradiol with enol ether acetal, methylprednisolone with acetate esters, testosterone with n-acetylglucosaminide glucosiduronate (trimethylsilyl) ether, cortisol or prednisolone or dexamethasone with 21-phosphate esters.

Prodrugs may also be designed as reversible drug derivatives and utilized as modifiers to enhance drug transport to site-specific tissues. Examples of parent molecules with reversible modifications or linkages to influence transport to a site specific tissue and for enhanced therapeutic effect include isocyanate with haloalkyl nitrosurea, testosterone with propionate ester, methotrexate (3-5'-dichloromethotrexate) with dialkyl esters, cytosine arabinoside with 5'-acylate, nitrogen mustard (2,2'-dichloro-N-methyldiethylamine), nitrogen mustard with aminomethyl tetracycline, nitrogen mustard with cholesterol or estradiol or dehydroepiandrosterone esters and nitrogen mustard with azobenzene.

As one skilled in the art would recognize, a particular chemical group to modify a given therapeutic may be selected to influence the partitioning of the therapeutic into either the membrane or the internal space of the microspheres. The bond selected to link the chemical group to the therapeutic may be selected to have the desired rate of metabolism, e.g., hydrolysis in the case of ester bonds in the presence of serum esterases after release from the gaseous precursor-filled microspheres. Additionally, the particular chemical group may be selected to influence the biodistribution of the therapeutic employed in the gaseous precursor-filled drug carrying microsphere invention, e.g., N,N-bis(2-chloroethyl)-phosphorodiamidic acid with cyclic phosphoramide for ovarian adenocarcinoma.

Additionally, the prodrugs employed within the gaseous precursor-filled microspheres may be designed to contain reversible derivatives which are utilized as modifiers of duration of activity to provide, prolong or depot action effects. For example, nicotinic acid may be modified with dextran and carboxymethlydextran esters, streptomycin with alginic acid salt, dihydrostreptomycin with pamoate salt, cytarabine (ara-C) with 5'-adamantoate ester, ara-adenosine (ara-A) with 5-palmitate and 5'-benzoate esters, amphotericin B with methyl esters, testosterone with 17-β-alkyl esters, estradiol with formate ester, prostaglandin with 2-(4-imidazolyl)ethylamine salt, dopamine with amino acid amides, chloramphenicol with mono- and bis(trimethylsilyl) ethers, and cycloguanil with pamoate salt. In this form, a depot or reservoir of long-acting drug may be released in vivo from the gaseous precursor-filled prodrug bearing microspheres.

In addition, compounds which are generally thermally labile may be utilized to create toxic free radical compounds. Compounds with azolinkages, peroxides and disulfide linkages which decompose with high temperature are preferred. With this form of prodrug, azo, peroxide or disulfide bond containing compounds are activated by cavitation and/or increased heating caused by the interaction of high energy sound with the gaseous precursor-filled microspheres to create cascades of free radicals from these prodrugs entrapped therein. A wide variety of drugs or chemicals may constitute these prodrugs, such as azo compounds, the general structure of such compounds being R—N═N—R, wherein R is a hydrocarbon chain, where the double bond between the two nitrogen atoms may react to create free radical products in vivo.

Exemplary drugs or compounds which may be used to create free radical products include azo containing compounds such as azobenzene, 2,2'-azobisisobutyronitrile, azodicarbonamide, azolitmin, azomycin, azosemide, azosulfamide, azoxybenzene, aztreonam, sudan III, sulfachrysoidine, sulfamidochrysoidine and sulfasalazine, compounds containing disulfide bonds such as sulbentine, thiamine disulfide, thiolutin, thiram, compounds containing peroxides such as hydrogen peroxide and benzoylperoxide, 2,2'-azobisisobutyronitrile, 2,2'-azobis(2-amidopropane) dihydrochloride, and 2,2'-azobis(2,4-dimethylvaleronitrile).

A gaseous precursor-filled microsphere filled with oxygen gas should create extensive free radicals with cavitation. Also, metal ions from the transition series, especially manganese, iron and copper can increase the rate of formation of reactive oxygen intermediates from oxygen. By encapsulating metal ions within the microspheres, the formation of free radicals in vivo can be increased. These metal ions may be incorporated into the microspheres as free salts, as complexes, e.g., with EDTA, DTPA, DOTA or desferrioxamine, or as oxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gaseous precursor-filled microspheres to create free radicals on thermal stimulation.

By way of an example of the use of prodrugs, an acylated chemical group may be bound to a drug via an ester linkage which would readily cleave in vivo by enzymatic action in serum. The acylated prodrug is incorporated into the gaseous precursor-filled microsphere of the invention. The derivatives, in addition to hydrocarbon and substituted hydrocarbon alkyl groups, may also be composed of halo substituted and perhalo substituted groups as perfluoroalkyl groups. Perfluoroalkyl groups should possess the ability to stabilize the emulsion. When the gaseous precursor-filled microsphere is popped by the sonic pulse from the ultrasound, the prodrug encapsulated by the microsphere will then be exposed to the serum. The ester linkage is then cleaved by esterases in the serum, thereby generating the drug.

Similarly, ultrasound may be utilized not only to rupture the gaseous precursor-filled microsphere, but also to cause thermal effects which may increase the rate of the chemical cleavage and the release of the active drug from the prodrug.

The microspheres may also be designed so that there is a symmetric or an asymmetric distribution of the therapeutic both inside and outside of the microsphere.

The particular chemical structure of the therapeutics may be selected or modified to achieve desired solubility such that the therapeutic may either be encapsulated within the internal gaseous precursor-filled space of the microsphere, attached to the microsphere or enmeshed in the microsphere. The surface-bound therapeutic may bear one or more acyl chains such that, when the microsphere is popped or heated or ruptured via cavitation, the acylated therapeutic may then leave the surface and/or the therapeutic may be cleaved from the acyl chains chemical group. Similarly, other therapeutics may be formulated with a hydrophobic group which is aromatic or sterol in structure to incorporate into the microsphere surface.

In addition to lipids, other materials that may be used to form the microspheres include, for example, proteins such as albumin, synthetic peptides such as polyglutamic acid, and linear and branched oligomers and polymers of galactose, glucose and other hexosaccharides and polymers derived from phosphorylated and sulfonated pentose and hexose sugars and sugar alcohols. Carbohydrate polymers such as alginic acid, dextran, starch and HETA starch may also be used. Other natural polymers, such as hyaluronic acid, may be utilized. Synthetic polymers such as polyethyleneglycol, polyvinylpyrrolidone, polylactide, polyethyleneimines (linear and branched), polyionenes or polyiminocarboxylates may also be employed.

Where the therapeutic encapsulated by the microspheres is negatively charged, such as genetic material, cationic lipids or perfluoroalkylated groups bearing cationic groups may be utilized to bind the negatively charged therapeutic. For example, cationic analogs of amphiphilic perfluoroalkylated bipyridines, as described in Garelli and Vierling, *Biochim. Biophys Acta,* 1992, 1127, 41–48, the disclosures of which are hereby incorporated herein by reference in their entirety, may be used.

In general, negatively charged therapeutics such as genetic material may be bound to the hydrophilic headgroups of mixed micellar components, e.g., non-cationic lipid with cationic lipids, for example, DOTMA or stearylamine or substituted alkyl groups such as trimethylstearylamine. Useful mixed micellar compounds include but are not limited to: lauryltrimethylammonium bromide (dodecyl-), cetyltrimethylammonium bromide (hexadecyl-), myristyltrimethylammonium bromide (tetradecyl-), alkyldimethylbenzylammonium chloride (alkyl=$C_{12}$, $C_{14}$, $C_{16}$,), benzyldimethyldodecylammonium bromide/chloride, benzyldimethylhexadecylammonium bromide/chloride, benzyldimethyltetradecylammonium bromide/chloride, cetyldimethylethylammonium bromide/chloride,or cetylpyridinium bromide/chloride.

The size of therapeutic containing liposomes can be adjusted, if desired, by a variety of procedures including extrusion, filtration, sonication, homogenization, employing a laminar stream of a core of liquid introduced into an immiscible sheath of liquid, extrusion under pressure through pores of defined size, and similar methods, in order to modulate resultant liposomal biodistribution and clearance. The foregoing techniques, as well as others, are discussed, for example, in U.S. Pat. No. 4,728,578; U.K. Patent Application GB 2193095 A; U.S. Pat. No. 4,728,575; U.S. Pat. No. 4,737,323; International Application PCT/US85/01161; Mayer et al., *Biochimica et Biophysica Acta,* Vol. 858, pp. 161–168 (1986); Hope et al., *Biochimica et Biophysica Acta,* Vol. 812, pp. 55–65 (1985); U.S. Pat. No. 4,533,254; Mayhew et al., *Methods in Enzymology,* Vol. 149, pp. 64–77 (1987); Mayhew et al., *Biochimica et Biophysica Acta,* Vol 755, pp. 169–74 (1984); Cheng et al, *Investigative Radiology,* Vol. 22, pp. 47–55 (1987); PCT/US89/05040, U.S. Pat. No. 4,162,282; U.S. Pat. No. 4,310,505; U.S. Pat. No. 4,921,706; and *Liposome Technology,* Gregoriadis, G., ed., Vol. I, pp. 29–31, 51–67 and 79–108 (CRC Press Inc., Boca Raton, Fla. 1984). The disclosures of each of the foregoing patents, publications and patent applications are incorporated by reference herein, in their entirety.

Filter pore sizes are selected for sizing as well as to remove any potential contaminants. The filter pore size may be between 10 nm and 20 $\mu$m, more preferably between 30 nm and 10 $\mu$m, and even more preferably between 100 nm and 8 $\mu$m. Most preferably, the filter pores are about 0.22 $\mu$m in size. Two or more filters may be stacked in a series to maximize the effectiveness of filtration. Useful materials for formation of the filters include polymers such as polysulfonate, polycarbonate, and polyvinylidene chloride. In addition, glass, ceramics, and metal filters may also be utilized. Additionally, wire, polymer, or ceramic meshes may also be utilized. Filtration may either be utilized. Filtration may be performed as part of the manufacturing process or during administration through an in-line filter.

The gaseous precursor-filled microspheres may be sized as a terminal step via a filtration process. A cascade filter comprising two or more serial filters, 10 micron followed by 8 micron, for example, increases yield. The result is a high yield of stable, uniform-sized, gaseous precursor-filled microspheres with great efficacy for ultrasonic imaging and drug delivery.

Taking advantage of principles in the ideal gas law and the expansion in size of the microspheres from the liquid to gaseous phases stable microspheres which are small enough to be injected through in line filters and provide the necessary contrast enhancement in vivo. Indeed, knowing the expansion in microsphere diameter upon liquid to gaseous transition a filter system may be designed such that the particles or emulsion is sized via a process of injection/filtration. Upon transition from the liquid to gaseous phases, the appropriate sized gas-filled microspheres will the form. Knowing the necessary volume of gaseous precursor and the contribution of the stabilizing materials to effective droplet diameter and then utilizing the ideal gas law, the optimal filter diameter for sizing the precursor droplets may be calculated. This, in turn, will produce microspheres of the desired diameter.

The gaseous precursor-filled microspheres may be sized by a simple process of extrusion through filters. The filter pore sizes control the size distribution of the resulting gaseous precursor-filled microspheres. By using two or more cascaded or a stacked set of filters, e.g. 10 micron followed by 8 micron, gaseous precursor-filled microspheres having a very narrow size distribution centered around 7–9 μm may be produced when extrusion is performed at a temperature above the phase transition temperature of the gaseous precursor. After filtration, these lipid coated microspheres remain stable for over 24 hours, and even up to a year or longer. The filtration step may be incorporated as a filter assembly when the suspension is removed from a sterile vial prior to use or even more preferably the filter assembly may be incorporated into the syringe itself during use. This process may be applied using differently sized filters, such that differently sized microspheres result.

The size of the microspheres of the present invention will depend upon the intended use. Since microsphere size influences biodistribution, different size microspheres may be selected for various purposes. With the smaller microspheres, resonant frequency ultrasound will generally be higher than for the larger microspheres.

For example, for intravascular application, the preferred size range is a mean outside diameter between about 30 nanometers and about 10 microns, with the preferable mean outside diameter being about 5 microns.

More specifically, for intravascular application, the size of the microspheres is preferably about 10 μm or less in mean outside diameter, and preferably less than about 7 μm, and more preferably no smaller than about 5 nanometers in outside diameter. Preferably, the microspheres are no smaller than about 30 nanometers in mean outside diameter.

To provide therapeutic delivery to organs such as the liver and to allow differentiation of tumor from normal tissue, smaller microspheres, between about 30 nanometers and about 100 nanometers in mean outside diameter, are preferred.

For embolization of a tissue such as the kidney or the lung, the microspheres are preferably less than about 200 microns in mean outside diameter.

For intranasal, intrarectal or topical administration, the microspheres are preferably less than about 100 microns in mean outside diameter.

Large microspheres, e.g., between 1 and 10 microns in size, will generally be confined to the intravascular space until they are cleared by phagocytic elements lining the vessels, such as the macrophages and Kuppfer cells lining capillary sinusoids. For passage to the cells beyond the sinusoids, smaller microspheres, for example, less than about a micron in diameter, e.g., less than about 300 nanometers in size, may be utilized.

In preferred embodiments, the microspheres are administered individually, rather than, for example, embedded in a matrix.

Generally, the therapeutic delivery systems of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may also be buffered, if desired, to provide a pH range of about pH 5 to about pH 7.4. The resulting gaseous precursor-filled lipid spheres remain stable on storage at room temperature for a year or even longer. In addition, dextrose may be preferably included in the media. Further solutions that may be used for administration of gaseous precursor-filled liposomes include, but are not limited to, almond oil, corn oil, cottonseed oil, ethyl oleate, isopropyl myristate, isopropyl palmitate, mineral oil, myristyl alcohol, octyl-dodecanol, olive oil, peanut oil, persic oil, sesame oil, soybean oil, squalene, myristyl oleate, cetyl oleate, myristyl palmitate, as well as other saturated and unsaturated alkyl chain alcohols (C=2–22) esterified to alkyl chain fatty acids (C=2–22).

For storage prior to use, the microspheres of the present invention may be suspended in an aqueous solution, such as a saline solution (for example, a phosphate buffered saline solution), or simply water, and stored preferably at a temperature of between about 2° C. and about 10° C., preferably at about 4° C. Preferably, the water is sterile. Most preferably, the microspheres are stored in an isotonic saline solution, although, if desired, the saline solution may be a hypotonic saline solution (e.g., about 0.3 to about 0.5% NaCl). The solution also may be buffered, if desired, to provide a pH range of about pH 5 to about pH 7.4. Suitable buffers for use in the storage media include, but are not limited to, acetate, citrate, phosphate and bicarbonate.

Bacteriostatic agents may also be included with the microspheres to prevent bacterial degradation on storage. Suitable bacteriostatic agents include but are not limited to benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid. One or more antioxidants may further be included with the gaseous precursor-filled liposomes to prevent oxidation of the lipid. Suitable antioxidants include tocopherol, ascorbic acid and ascorbyl palmitate.

Methods of controlled delivery of therapeutic compounds to a region of a patient involve the steps of:

(i) administering to the patient gaseous precursor-filled microspheres comprising a therapeutic compound;

(ii) monitoring the microspheres using ultrasound to detect the liquid to gas phase transition of the gaseous precursor and to determine the presence of the microspheres in the region; and (iii) rupturing the microspheres using ultrasound to release the therapeutic compound in the region.

Using the gaseous precursor-filled microspheres of the present invention, ultrasonic energy interacts with the gas, bursting the microspheres and allowing a therapeutic such as, for example, genetic material to be released and transported into cells. When the sonic energy encounters the interface of the gas within the tissue or fluid medium, local conversion of sonic energy into thermal and kinetic energy is greatly enhanced. The therapeutic material is thereby released from the microspheres and surprisingly delivered into the cells. Although not intending to be bound by any particular theory of operation, it is believed that the thermal and kinetic energy created at the site of the cell enhances cellular uptake of the therapeutic.

The route of administration of the microspheres will vary depending on the intended use. As one skilled in the art would recognize, administration of therapeutic delivery systems of the present invention may be carried out in various fashions, such as intravascularly, intralymphatically, parenterally, subcutaneously, intramuscularly, intranasally, intrarectally, intraperitoneally, interstitially, into the airways via nebulizer, hyperbarically, orally, topically, or intratumorly, using a variety of dosage forms. One preferred route of administration is intravascularly. For intravascular use, the therapeutic delivery system is generally injected intravenously, but may be injected intraarterially as well. The microspheres of the invention may also be injected interstitially or into any body cavity.

The delivery of therapeutics from the microspheres of the present invention using ultrasound is best accomplished for tissues which have a good acoustic window for the transmission of ultrasonic energy. This is the case for most tissues in the body such as muscle, the heart, the liver and most other vital structures. In the brain, in order to direct the ultrasonic energy past the skull a surgical window may be necessary.

The useful dosage to be administered and the mode of administration will vary depending upon the age, weight, and type of animal to be treated, and the particular therapeutic application intended. Typically, dosage is initiated at lower levels and increased until the desired therapeutic effect is achieved.

Although ultrasound energy is preferred for activation of sight directed drug delivery, in certain cases other forms of energy can be utilized. For example, when a good acoustic window is not available, e.g. the lung, microwave radiofrequency energy may be utilized. This can be used for example to cause a gaseous precursor to undergo the phase transition in the region of the body being heated and in doing so release the drugs from the surface of the microsphere. For example, a microsphere entrapping 2-methyl-2-butene and a chemotherapeutic agent could be activated by local hyperthermia using microwave or ultrasound of about 38.5 C, only a couple of degrees over body temperature. In magnetic induction, an oscillating magnetic field is used to create heating. This can be accomplished with an external magnetic field (i.e. the magnet outside the patient) and ferromagnetic probes implanted within the patient, e.g. within a tumor. As a microspheres flow through the vessels within the tumor they will encounter heat in the region due to the magnetic field oscillation. The gaseous precursor may then form gas, rupture the microsphere and release the drug. A particularly novel aspect of the invention is that magnetic microspheres may be made. This can be accomplished by using a magnetic material within the microsphere, for example iron oxide particles entrapped within the microsphere along with the gaseous precursor and the therapeutic agent. As the microsphere encounters the region of magnetic field, the magnetic particles capture the energy from the oscillating magnetic field and convert this energy into heat. This in turn converts the liquid gaseous precursor into gas locally releasing the contents of the microsphere. Light energy is useful for directing drug delivery with the microspheres in certain instances. Light generally is less effective at penetrating into the depths of body tissues than, for example, sound or radiofrequency energy, but in certain applications, the level of penetration is adequate. For example, to deliver drugs to the skin the gaseous precursor filled microspheres could be applied topically and sunlamps then applied to the skin. The microspheres can also be injected I.V. and target the skin by shining light of the appropriate energy onto the skin. It is believed that infrared light energy is particularly effective at interacting with the perfluorocarbon based gaseous precursors to cause photoactivation. For endoscopic application (e.g. to treat the mucosal surface of the colon) light energy can also be quite useful.

The preferred method of performing site directed drug delivery with the gaseous precursor microspheres is to apply energy to the target tissues and in doing so, release the therapeutics from the microspheres. The most preferred energy source is ultrasound. In certain instances, however, the gaseous precursor microspheres can be extremely effective on their own in terms of locally deliverying drugs. It is believed that gaseous precursors which undergo a liquid to gaseous phase transition at close to body temperature are particularly effective at accumulating in ischemic and diseased tissues. This hypothesis derives from experiments performed with conventional liposomes filled with air. When experimental animals are ventillated with 100% oxygen, e.g. pigs or dogs, the liposomes lose the gas very quickly. Gaseous precursors which undergo phase transitions at close to the body temperature (e.g. 37 C.) tend to accumulate within diseased or ischemic tissue. Tumors are often ischemic, as are infected areas of myocardium, brain, and other tissues. The gaseous precursors then may be used to accomplish local drug delivery. Particularly preferred are precursors which undergo liquid to gaseous transitions at temperatures between 25° C. and about 40° C. for this purpose. By incorporating the therapeutic into the microsphere with the gaseous precursor which might entrap for example, perfluoropentane, 1-butene-3-yne-2-methyl, methyl-lactate or bromochlorofluoromethane, the therapeutic agent may be selectively delivered to ischemic tissues. Ultrasound or other energy may be optionally applied to the ischemic tissue to facillitate drug delivery.

For in vitro use, such as cell culture applications, the gaseous precursor-filled microspheres may be added to the cells in cultures and then incubated. Sonic energy can then be applied to the culture media containing the cells and microspheres.

The present invention may be employed in the controlled delivery of therapeutics to a region of a patient wherein the patient is administered the therapeutic containing microsphere of the present invention, the microspheres are monitored using ultrasound to determine the presence of the microspheres in the region, and the microspheres are then ruptured using ultrasound to release the therapeutics in the region.

The patient may be any type of animal, but is preferably a vertebrate, more preferably a mammal, and most preferably human. By region of a patient, it is meant the whole patient, or a particular area or portion of the patient. For example, by using the method of the invention, therapeutic delivery may be effected in a patient's heart, and a patient's vasculature (that is, venous or arterial systems). The invention is also particularly useful in delivering therapeutics to a patient's left heart, a region not easily reached heretofore with therapeutic delivery. Therapeutics may also be easily delivered to the liver, spleen and kidney regions of a patient, as well as other regions, using the present methods.

Additionally, the invention is especially useful in delivering therapeutics to a patient's lungs. Gaseous precursor-filled microspheres of the present invention are lighter than, for example, conventional liquid-filled liposomes which generally deposit in the central proximal airway rather than reaching the periphery of the lungs. It is therefore believed that the gaseous precursor-filled microspheres of the present invention may improve delivery of a therapeutic compound to the periphery of the lungs, including the terminal airways and the alveoli. For application to the lungs, the gaseous precursor-filled microspheres may be applied through nebulization, for example.

In applications such as the targeting of the lungs, which are lined with lipids, the therapeutic may be released upon aggregation of a gaseous precursor-filled lipid microsphere with the lipids lining the targeted tissue. Additionally, the gaseous precursor-filled lipid microspheres may burst after administration without the use of ultrasound. Thus, ultrasound need not be applied to release the therapeutic in the above type of administration.

Further, the gaseous precursor-filled microspheres of the invention are especially useful for therapeutics that may be degraded in aqueous media or upon exposure to oxygen and/or atmospheric air. For example, the microspheres may be filled with an inert gas such as nitrogen or argon, for use with labile therapeutic compounds. Additionally, the gaseous precursor-filled microspheres may be filled with an inert gas and used to encapsulate a labile therapeutic for use in a region of a patient that would normally cause the therapeutic to be exposed to atmospheric air, such as cutaneous and ophthalmic applications.

The gaseous precursor-filled microspheres are also especially useful for transcutaneous delivery, such as a patch delivery system. The use of rupturing ultrasound may increase transdermal delivery of therapeutic compounds. Further, a mechanism may be used to monitor and modulate therapeutic delivery. For example, diagnostic ultrasound may be used to visually monitor the bursting of the gaseous precursor-filled microspheres and modulate therapeutic delivery and/or a hydrophone may be used to detect the sound of the bursting of the gaseous precursor-filled microspheres and modulate therapeutic delivery.

The echogenicity of the microspheres and the ability to rupture the microspheres at the peak resonant frequency using ultrasound permits the controlled delivery of therapeutics to a region of a patient by allowing the monitoring of the microspheres following administration to a patient to determine the presence of microspheres in a desired region, and the rupturing of the microspheres using ultrasound to release the therapeutics in the region.

Gas-filled microspheres prepared from gaseous precursors have great efficacy for diagnostic ultrasound. They entrap a large amount of gas, such that they are highly reflective and are excellent ultrasound contrast agents. High energy ultrasound, preferably continuous wave, above 100 milliwatts, may be used to release drugs, bioactive and genetic materials from the Aerosomes, to augment ultrasonic hyperthermia and for cavitation mediated tissue destruction and drug activation.

Preferably, the microspheres of the invention possess a reflectivity of greater than 2 dB, preferably between about 4 dB and about 20 dB. Within these ranges, the highest reflectivity for the microspheres of the invention is exhibited by the larger microspheres, by higher concentrations of microspheres, and/or when higher ultrasound frequencies are employed.

Preferably, the microspheres of the invention have a peak resonant frequency of between about 0.5 mHz and about 10 mHz. Of course, the peak resonant frequency of the gaseous precursor-filled microspheres of the invention will vary depending on the diameter and, to some extent, the elasticity or flexibility of the microspheres, with the larger and more elastic or flexible microspheres having a lower resonant frequency than the smaller and less elastic or flexible microspheres.

The rupturing of the therapeutic containing microspheres of the invention is surprisingly easily carried out by applying ultrasound of a certain frequency to the region of the patient where therapy is desired, after the microspheres have been administered to or have otherwise reached that region. Specifically, it has been unexpectedly found that when ultrasound is applied at a frequency corresponding to the peak resonant frequency of the therapeutic containing gaseous precursor-filled microspheres, the microspheres will rupture and release their contents.

The peak resonant frequency can be determined either in vivo or in vitro, but preferably in vivo, by exposing the microspheres to ultrasound, receiving the reflected resonant frequency signals and analyzing the spectrum of signals received to determine the peak, using conventional means. The peak, as so determined, corresponds to the peak resonant frequency (or second harmonic, as it is sometimes termed).

The gaseous precursor-filled microspheres will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and therapeutic release is improved, appreciable tissue heating does not generally occur (frequently no increase in temperature above about 2° C.), and less overall energy is required. Thus, application of ultrasound at the peak resonant frequency, while not required, is most preferred.

Any of the various types of diagnostic ultrasound imaging devices may be employed in the practice of the invention, the particular type or model of the device not being critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, preferably at peak resonant frequency, and then intensity, time, and/or resonant frequency increased until the microsphere ruptures.

Although application of the various principles will be readily apparent to one skilled in the art, once armed with the present disclosure, by way of general guidance, for gaseous precursor-filled microspheres of about 1.5 to about 10 microns in mean outside diameter, the resonant frequency will generally be in the range of about 1 to about 10 megahertz. By adjusting the focal zone to the center of the target tissue (e.g., the tumor) the gaseous precursor-filled microspheres can be visualized under real time ultrasound as they accumulate within the target tissue. Using the 7.5 megahertz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of therapeutic from the gaseous precursor-filled microspheres, but much greater release can be accomplished by using higher power.

By switching the transducer to the doppler mode, higher power outputs are available, up to 2.5 watts per cm$^2$ from the same transducer. With the machine operating in doppler mode, the power can be delivered to a selected focal zone within the target tissue and the gaseous precursor-filled microspheres can be made to release their therapeutics. Selecting the transducer to match the resonant frequency of the gaseous precursor-filled microspheres will make this process of therapeutic release even more efficient.

For larger diameter gaseous precursor-filled microspheres, e.g., greater than 3 microns in mean outside diameter, a lower frequency transducer may be more effective in accomplishing therapeutic release. For example, a lower frequency transducer of 3.5 megahertz (20 mm curved array model) may be selected to correspond to the resonant frequency of the gaseous precursor-filled microspheres. Using this transducer, 101.6 milliwatts per cm$^2$ may be delivered to the focal spot, and switching to doppler mode will increase the power output (SPTA) to 1.02 watts per cm$^2$.

To use the phenomenon of cavitation to release and/or activate the drugs/prodrugs within the gaseous precursor-filled microspheres, lower frequency energies may be used, as cavitation occurs more effectively at lower frequencies. Using a 0.757 megahertz transducer driven with higher voltages (as high as 300 volts) cavitation of solutions of gaseous precursor-filled microspheres will occur at thresholds of about 5.2 atmospheres.

Table III shows the ranges of energies transmitted to tissues from diagnostic ultrasound on commonly used instruments such as the Piconics Inc. (Tyngsboro, Mass.) Portascan general purpose scanner with receiver pulser 1966 Model 661; the Picker (Cleveland, Ohio) Echoview 8L Scanner including 80C System or the Medisonics (Mountain View, Calif.) Model D-9 Versatone Bidirectional Doppler. In general, these ranges of energies employed in pulse repetition are useful for monitoring the gas-filled microspheres but are insufficient to rupture the gas-filled microspheres of the present invention.

TABLE III

Power and Intensities Produced by Diagnostic Equipment*

| Pulse repetition rate (Hz) | Total ultrasonic power output P (mW) | Average Intensity at transducer face $I_{TD}$ (W/m$^2$) |
| --- | --- | --- |
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Ultrasound in Med. & Biol. 1978 3, 341–350, the disclosures of which are hereby incorporated by reference in their entirety.

Higher energy ultrasound such as commonly employed in therapeutic ultrasound equipment is preferred for activation of the gaseous precursor-filled microspheres. In general, therapeutic ultrasound machines employ as much as 50% to 100% duty cycles dependent upon the area of tissue to be heated by ultrasound. Areas with larger amounts of muscle mass (i.e., backs, thighs) and highly vascularized tissues such as heart may require the larger duty cycle, e.g., 100%.

In diagnostic ultrasound, which may be used to monitor the location of the gaseous precursor-filled microspheres, one or several pulses of sound are used and the machine pauses between pulses to receive the reflected sonic signals. The limited number of pulses used in diagnostic ultrasound limits the effective energy which is delivered to the tissue which is being imaged.

In therapeutic ultrasound, continuous wave ultrasound is used to deliver higher energy levels. In using the microspheres of the present invention, the sound energy may be pulsed, but continuous wave ultrasound is preferred. If pulsing is employed, the sound will preferably be pulsed in echo train lengths of at least about 8 and preferably at least about 20 pulses at a time.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the microspheres and rupturing to provide local delivery of therapeutics.

The frequency of the sound used may vary from about 0.025 to about 100 megahertz. Frequency ranges between about 0.75 and about 3 megahertz are preferred and frequencies between about 1 and about 2 megahertz are most preferred. Commonly used therapeutic frequencies of about 0.75 to about 1.5 megahertz may be used. Commonly used diagnostic frequencies of about 3 to about 7.5 megahertz may also be used. For very small microspheres, e.g., below 0.5 micron diameter, higher frequencies of sound may be preferred as these smaller microspheres will absorb sonic energy more effectively at higher frequencies of sound. When very high frequencies are used, e.g., over 10 megahertz, the sonic energy will generally have limited depth penetration into fluids and tissues. External application may be preferred for the skin and other superficial tissues, but for deep structures, the application of sonic energy via interstitial probes or intravascular ultrasound catheters may be preferred.

In a most preferred embodiment, the present invention provides novel liposomal contrast agent and drug delivery systems.

Various methods for preparing the gaseous precursor-filled therapeutic containing microspheres of the present invention will be readily apparent to those skilled in the art, once armed with the present disclosure. Preferred methods for preparing the microspheres are discussed below in connection with the preferred liposomal therapeutic delivery systems.

Specifically, in a preferred embodiment, a method for preparing a targeted therapeutic delivery system comprising temperature activated gaseous precursor-filled liposomes of the subject invention comprises the steps of shaking an aqueous solution, comprising a lipid, in the presence of a temperature activated gaseous precursor at a temperature below the gel to liquid crystalline phase transition temperature of the lipid and below the activation temperature of the gaseous precursor to form temperature activated gaseous precursor-filled liposomes, and adding a therapeutic compound. In another preferred embodiment, a method for preparing a targeted therapeutic delivery system comprising temperature activated gaseous precursor-filled liposomes of the subject invention comprises the step of shaking an aqueous solution comprising a lipid and a therapeutic compound in the presence of a temperature activated gaseous precursor at a temperature below the gel to liquid crystalline phase transition temperature of the lipid and below the activation temperature of the gaseous precursor. In other embodiments, methods for preparing a targeted therapeutic delivery system comprising temperature activated gaseous precursor-filled liposomes comprise the steps of shaking an aqueous solution, comprising a lipid and a therapeutic compound, in the presence of a temperature activated gaseous precursor, and separating the resulting gaseous precursor-filled liposomes for therapeutic use. Liposomes prepared by the foregoing methods are referred to herein as temperature activated gaseous precursor-filled liposomes prepared by a gel state shaking gaseous precursor installation method and comprising a therapeutic compound, or as therapeutic containing gel state shaken temperature activated gaseous precursor instilled liposomes.

The methods of preparing the microspheres of the present invention may be performed at or near the activation temperature of the gaseous precursor, such that gas-filled liposomes are formed. In this embodiment, a method for preparing a targeted therapeutic delivery system comprising gas-filled liposomes of the subject invention comprises the steps of shaking an aqueous solution, comprising a lipid, in the presence of gas at a temperature below the gel to liquid crystalline phase transition temperature of the lipid and below the activation temperature of the gaseous precursor to form gas-filled liposomes, and adding a therapeutic compound. In another preferred embodiment, a method for preparing a targeted therapeutic delivery system comprising gas-filled liposomes of the subject invention comprises the step of shaking an aqueous solution comprising a lipid and a therapeutic compound in the presence of a gas at a temperature below the gel to liquid crystalline phase transition temperature of the lipid. In other embodiments, methods for preparing a targeted therapeutic delivery system comprising gas-filled liposomes comprise the steps of shaking an aqueous solution, comprising a lipid and a therapeutic compound, in the presence of a gaseous, and separating the resulting gas-filled liposomes for therapeutic use. Liposomes prepared by the foregoing methods are referred to herein as gas-filled liposomes prepared by a gel state shaking gas installation method and comprising a therapeutic compound, or as therapeutic containing gel state shaken gas instilled liposomes.

Thus, a preferred method of the present invention provides for shaking an aqueous solution comprising a lipid and a therapeutic compound in the presence of a temperature activated gaseous precursor. Shaking, as used herein, is defined as a motion that agitates an aqueous solution such that gas is introduced from the local ambient environment into the aqueous solution. Accordingly, shaking is performed at a temperature which forms gas-filled liposomes or gaseous precursor-filled liposomes. Any type of motion that agitates the aqueolution and results in the introduction of gas may be used for the shaking. The shaking must be of sufficient force to allow the formation of foam after a period of time. Preferably, the shaking is of sufficient force such that foam is formed within a short period of time, such as 30 minutes, and preferably within 20 minutes, and more preferably, within 10 minutes. The shaking may be by swirling (such as by vortexing), side-to-side, or up and down motion. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table such as a VWR Scientific (Cerritos, Calif.) shaker table and a mechanical paint mixer, as well as other known machines. Another means for producing shaking includes the action of gas emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at at least 1000 revolutions per minute, an example of vigorous shaking, is more preferred. Vortexing at 1800 revolutions per minute is most preferred.

The formation of gaseous precursor-filled liposomes upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous lipid solution; more preferably, the final volume of the foam is at least about three times the initial volume of the aqueous solution; even more preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gaseous precursor-filled liposomes becomes sufficiently thick so that it no longer clings to the side walls as it is swirled. At this time, the foam may cause the solution containing the gaseous precursor-filled liposomes to raise to a level of 30 to 35 ml.

The concentration of lipid required to form a preferred foam level will vary depending upon the type of lipid used, and may be readily determined by one skilled in the art, once armed with the present disclosure. For example, in preferred embodiments, the concentration of 1,2-dipalimitoyl-phosphatidylcholine (DPPC) used to form gaseous precursor-filled liposomes according to the methods of the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume completely devoid of any liquid suspension volume and contains entirely foam.

It will be understood by one skilled in the art, once armed with the present disclosure, that the lipids or liposomes may be manipulated prior and subsequent to being subjected to the methods of the present invention. For example, the lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gaseous precursor-filled liposomes.

According to the methods of the present invention, the presence of gas may be provided by the local ambient atmosphere. The local ambient atmosphere may be the atmosphere within a sealed container, or in an unsealed container, may be the external environment. Alternatively, in the preferred embodiment of the present invention, a gas or gaseous precursor may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

The foregoing preferred method of the invention is preferably carried out at a temperature below the gel to liquid crystalline phase transition temperature of the lipid employed. By "gel to liquid crystalline phase transition temperature", it is meant the temperature at which a lipid bilayer will convert from a gel state to a liquid crystalline state. See, for example, Chapman et al., *J. Biol. Chem.* 1974, 249, 2512–2521. The gel state to liquid crystalline state phase transition temperatures of various lipids will be readily apparent to those skilled in the art and are described, for example, in Gregoriadis, ed., *Liposome Technology,* Vol. I, 1–18 (CRC Press, 1984) and Derek Marsh, *CRC Handbook of Lipid Bilayers* (CRC Press, Boca Raton, Fla. 1990), at p. 139. See also Table II, above. Where the gel state to liquid crystalline state phase transition temperature of the lipid employed is higher than room temperature, the temperature of the container may be regulated, for example, by providing a cooling mechanism to cool the container holding the lipid solution.

The method of the invention is preferably also carried out at a temperature below the transition temperature of the liquid phase of the gaseous precursor. See Table I, above. The activation or transition temperature of other gaseous precursors identified above will be readily apparent to those skilled in the art and are described, for example, in *Chemical Rubber Company Handbook of Chemistry and Physics* Robert C. Weast and David R. Lide, eds. CRC Press, Inc. Boca Raton, Fla. (1989–1990). Alternatively, methods of preparing the microspheres of the present invention may also be performed at or near the activation temperature of the gaseous precursor, such that gas-filled liposomes are formed.

Conventional, aqueous-filled liposomes are routinely formed at a temperature above the gel to liquid crystalline phase transition temperature of the lipid, since they are more flexible and thus useful in biological systems in the liquid crystalline state. See, for example, Szoka and Papahadjopoulos, *Proc. Natl. Acad. Sci.* 1978, 75, 4194–4198. In contrast, the liposomes made according to preferred embodiments of the methods of the present invention are ultimately gas-filled, which imparts greater flexibility since gas is more compressible and compliant than an aqueous solution. Thus, the temperature activated gaseous precursor-filled liposomes may be utilized in biological systems when formed at a temperature below the phase transition temperature of the lipid, even though the gel phase is more rigid.

Figure 9:
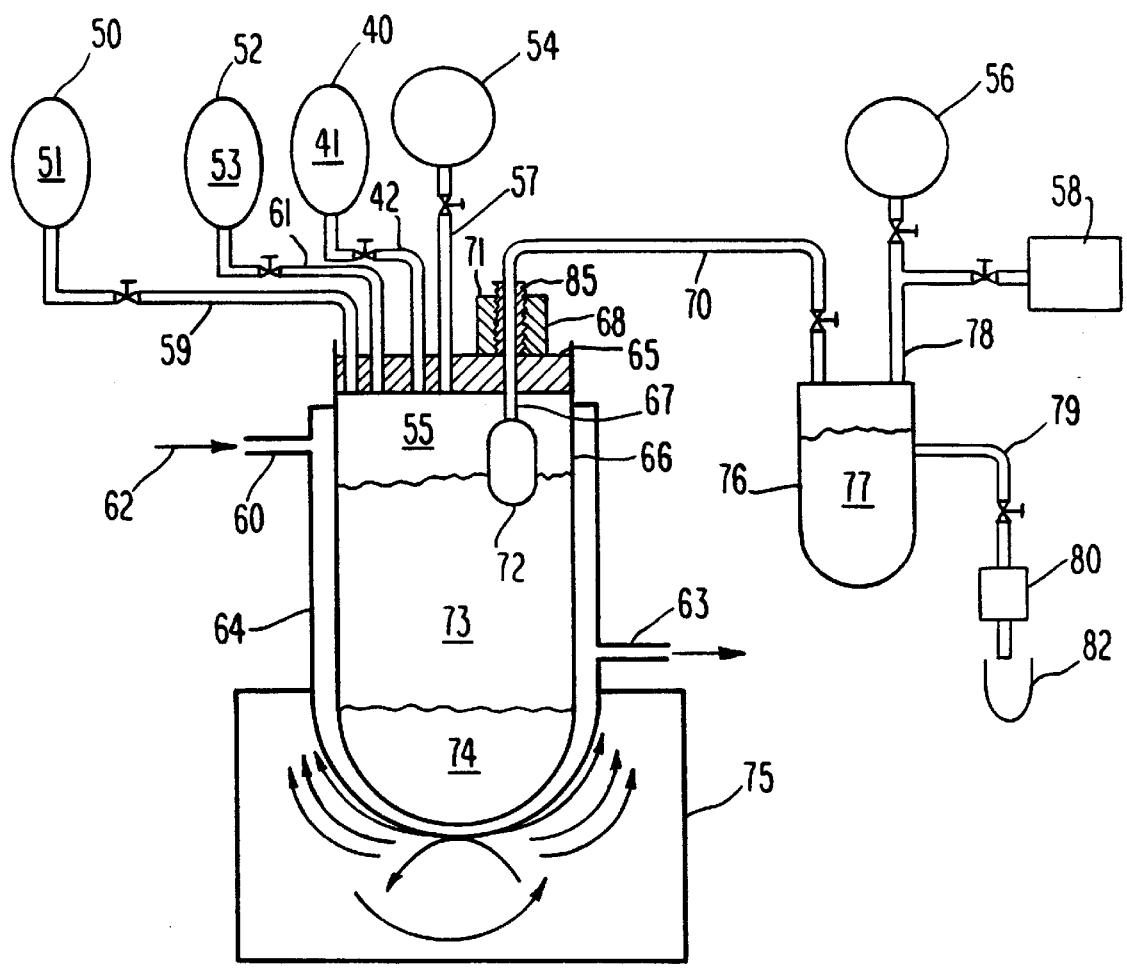
FIG. 9 is a view, partially schematic, of a preferred apparatus according to the present invention for preparing the therapeutic containing gaseous precursor-filled liposome microspheres of the present invention.

A preferred apparatus for producing the therapeutic containing gaseous precursor-filled liposomes using a gel state shaking gas instillation process is shown in FIG. 9. A mixture of lipid and aqueous media is vigorously agitated in the process of gas installation to produce gaseous precursor-filled liposomes, either by batch or by continuous feed. Referring to FIG. 9, dried lipids 51 from a lipid supply vessel 50 are added via conduit 59 to a mixing vessel 66 in either a continuous flow or as intermittent boluses. If a batch process is utilized, the mixing vessel 66 may comprise a relatively small container such as a syringe, test tube, bottle or round bottom flask, or a large container. If a continuous feed process is utilized, the mixing vessel is preferably a large container, such as a vat. The apparatus may be regulated such that a temperature at the phase transition temperature of the gaseous precursor results in gas-filled liposomes, whereas a temperature below the transition temperature results in gaseous-precursor filled liposomes. In the apparatus set forth below, the methods of making the microspheres are carried out at a temperature below the transition temperature. However, the methods may also be performed at the phase transition temperature to result in gas-filled liposomes.

The therapeutic compound may be added, for example, before the gas installation process. Referring to FIG. 9, the therapeutic compound 41 from a therapeutic compound supply vessel 40 is added via conduit 42 to a mixing vessel 66. Alternatively, the therapeutic compound may be added after the gas installation process, such as when the liposomes are coated on the outside with the therapeutic compound.

In addition to the lipids 51, and therapeutic compound 41, an aqueous media 53, such as a saline solution, from an aqueous media supply vessel 52, is also added to the vessel 66 via conduit 61. The lipids 51 and the aqueous media 53 combine to form an aqueous lipid solution 74. Alternatively, the dried lipids 51 could be hydrated prior to being introduced into the mixing vessel 66 so that lipids are introduced in an aqueous solution. In the preferred embodiment of the method for making liposomes, the initial charge of solution 74 is such that the solution occupies only a portion of the capacity of the mixing vessel 66. Moreover, in a continuous process, the rates at which the aqueous lipid solution 74 is added and gaseous precursor-filled liposomes produced are removed is controlled to ensure that the volume of lipid solution 74 does not exceed a predetermined percentage of the mixing vessel 66 capacity.

The shaking may be accomplished by introducing a high velocity jet of a pressurized gaseous precursor directly into the aqueous lipid solution 74. Alternatively, the shaking may be accomplished by mechanically shaking the aqueous solution, either manually or by machine. Such mechanical shaking may be effected by shaking the mixing vessel 66 or by shaking the aqueous solution 74 directly without shaking the mixing vessel itself. As shown in FIG. 9, in the preferred embodiment, a mechanical shaker 75, is connected to the mixing vessel 66. The shaking should be of sufficient intensity so that, after a period of time, a foam 73 comprised of gaseous precursor-filled liposomes is formed on the top of the aqueous solution 74, as shown in FIG. 9. The detection of the formation of the foam 73 may be used as a means for controlling the duration of the shaking; that is, rather than shaking for a predetermined period of time, the shaking may be continued until a predetermined volume of foam has been produced.

The apparatus may also contain a means for controlling temperature such that apparatus may be maintained at one temperature for the method of making the liposomes. For example, in the preferred embodiment, the methods of making liposomes are performed at a temperature below the boiling point of the gaseous precursor. In the preferred embodiment, a liquid gaseous precursor fills the internal space of the liposomes. Alternatively, the apparatus may be maintained at about the temperature of the liquid to gas transition temperature of the gaseous precursor such that a gas is contained in the liposomes. Further, the temperature of the apparatus may be adjusted throughout the method of making the liposomes such that the gaseous precursor begins as a liquid, however, a gas is incorporated into the resulting liposomes. In this embodiment, the temperature of the apparatus is adjusted during the method of making the liposomes such that the method begins at a temperature below the phase transition temperature and is adjusted to a temperature at about the phase transition temperature of the gaseous precursor.

In a preferred embodiment of the apparatus for making gaseous precursor-filled liposomes in which the lipid employed has a gel to liquid crystalline phase transition temperature below room temperature, a means for cooling the aqueous lipid solution 74 is provided. In the embodiment shown in FIG. 9, cooling is accomplished by means of a jacket 64 disposed around the mixing vessel 66 so as to form an annular passage surrounding the vessel. As shown in FIG. 9, a cooling fluid 63 is forced to flow through this annular passage by means of jacket inlet and outlet ports 62 and 63, respectively. By regulating the temperature and flow rate of the cooling fluid 62, the temperature of the aqueous lipid solution 74 can be maintained at the desired temperature.

As shown in FIG. 9, a gaseous precursor 55, is introduced into the mixing vessel 66 along with the aqueous solution 74. Air may be introduced by utilizing an unsealed mixing vessel so that the aqueous solution is continuously exposed to environmental air. In a batch process, a fixed charge of local ambient air may be introduced by sealing the mixing vessel 66. If a gaseous precursor heavier than air is used, the container need not be sealed. However, introduction of gaseous precursors that are not heavier than air will require that the mixing vessel be sealed, for example by use of a lid 65, as shown in FIG. 9. The gaseous precursor 55 may be pressurized in the mixing vessel 66, for example, by connecting the mixing vessel to a pressurized gas supply tank 54 via a conduit 57, as shown in FIG. 9.

After the shaking is completed, the gaseous precursor-filled liposome containing foam 73 may be extracted from the mixing vessel 66. Extraction may be accomplished by inserting the needle 102 of a syringe 100, shown in FIG. 10, into the foam 73 and drawing a predetermined amount of foam into the barrel 104 by withdrawing the plunger 106. As discussed further below, the location at which the end of the needle 102 is placed in the foam 73 may be used to control the size of the gaseous precursor-filled liposomes extracted.

Alternatively, extraction may be accomplished by inserting an extraction tube 67 into the mixing vessel 66, as shown in FIG. 9. If the mixing vessel 66 is pressurized, as previously discussed, the pressure of the gas 55 may be used to force the gaseous precursor-filled liposomes 77 from the mixing vessel 66 to an extraction vessel 76 via conduit 70. In the event that the mixing vessel 66 is not pressurized, the extraction vessel 76 may be connected to a vacuum source 58, such as a vacuum pump, via conduit 78, that creates sufficient negative pressure to suck the foam 73 into the extraction vessel 76, as shown in FIG. 9. From the extraction vessel 76, the gaseous precursor-filled liposomes 77 are introduced into vials 82 in which they may be shipped to the ultimate user. A source of pressurized gas 56 may be connected to the extraction vessel 76 as aid to ejecting the gaseous precursor-filled liposomes. Since negative pressure may result in increasing the size of the gaseous precursor-filled liposomes, positive pressure is preferred for removing the gaseous precursor-filled liposomes.

Figures 10, 11, 12:
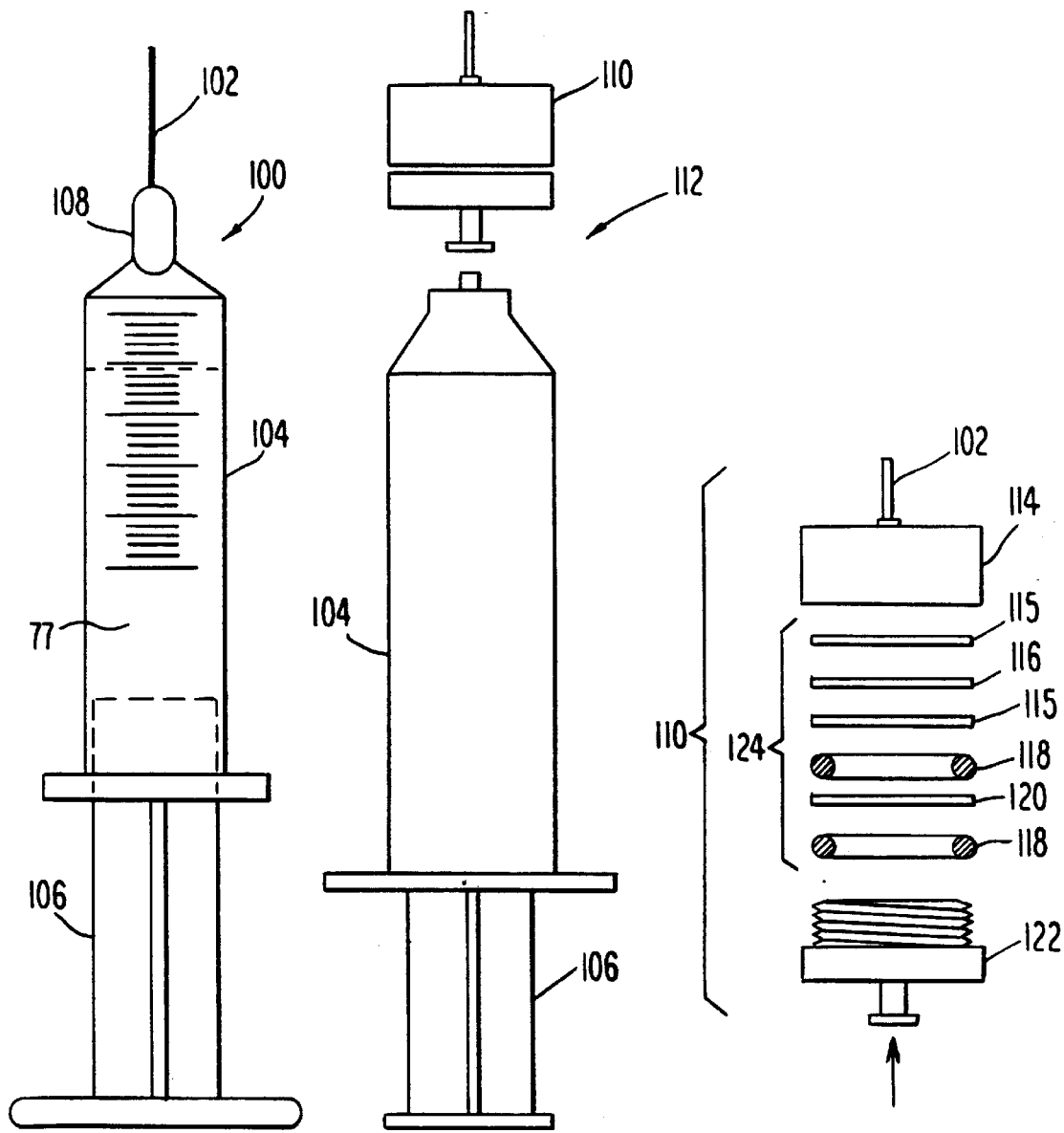
FIG. 10 shows a preferred apparatus for filtering and/or dispensing therapeutic containing gaseous precursor-filled liposome microspheres of the present invention.
FIG. 11 depicts a preferred apparatus for filtering and/or dispensing therapeutic containing gaseous precursor-filled liposome microspheres of the present invention.
FIG. 12 is an exploded view of a portion of the apparatus of FIG. 11.
Figure 15A:
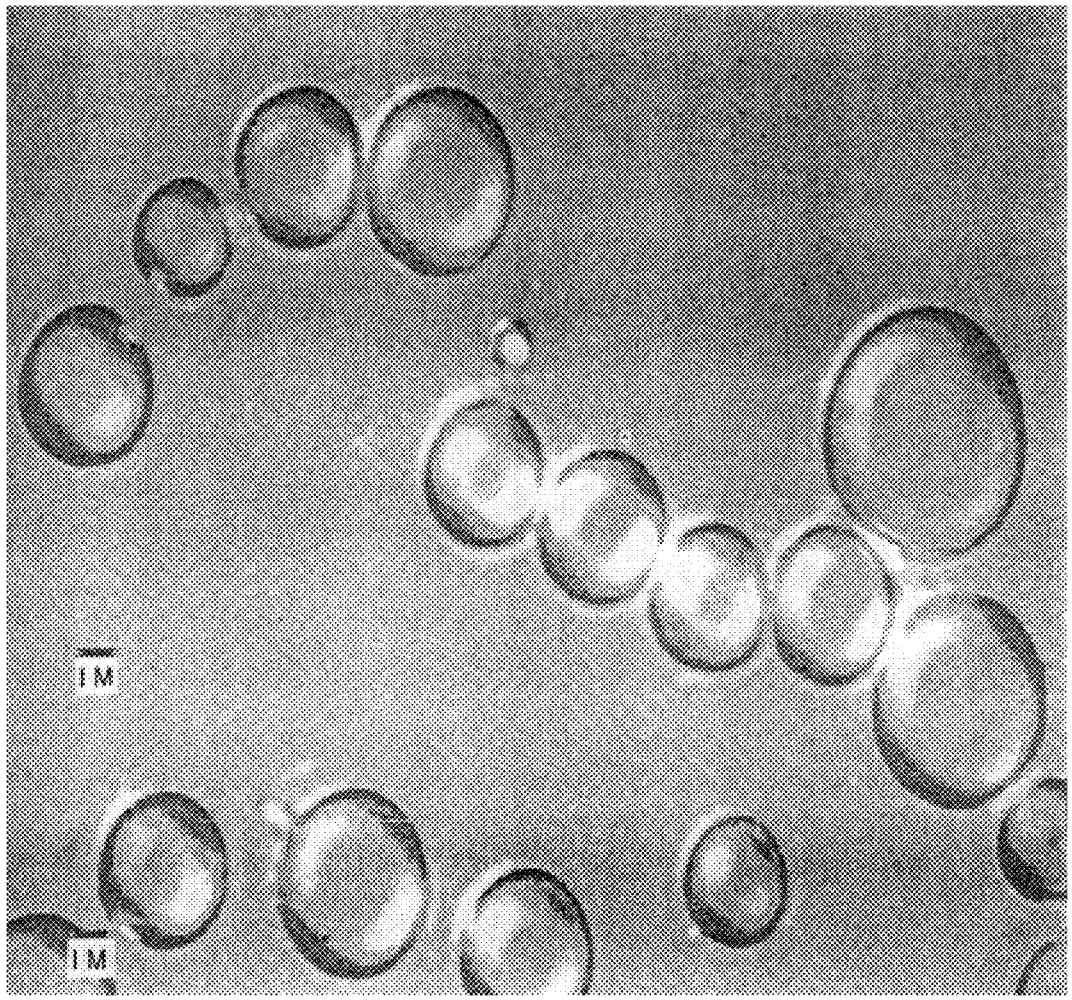
FIG. 15 is a micrograph which shows the sizes of gaseous precursor-filled liposomes of the invention before (A) and after (B) filtration through a 10 micron filter.
Figure 15B:
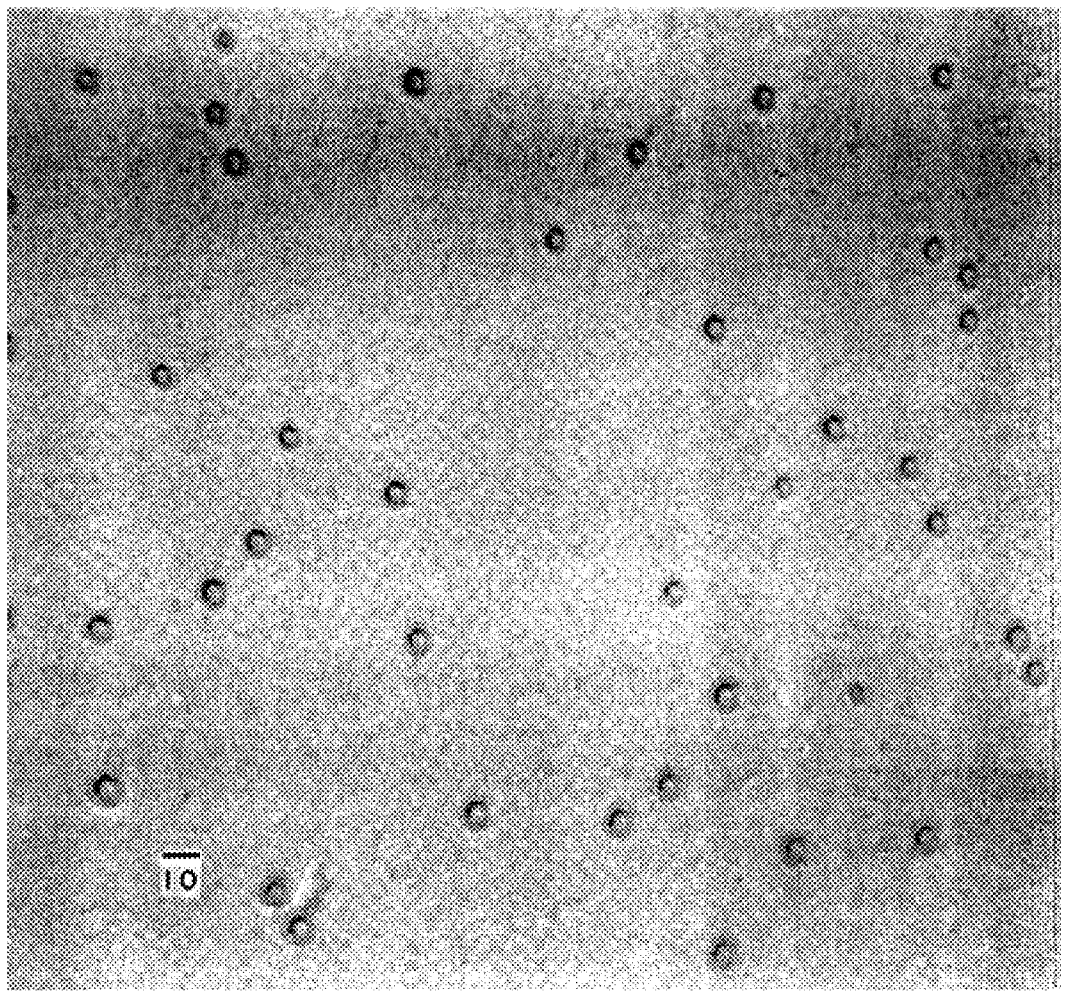
Figure 16A:
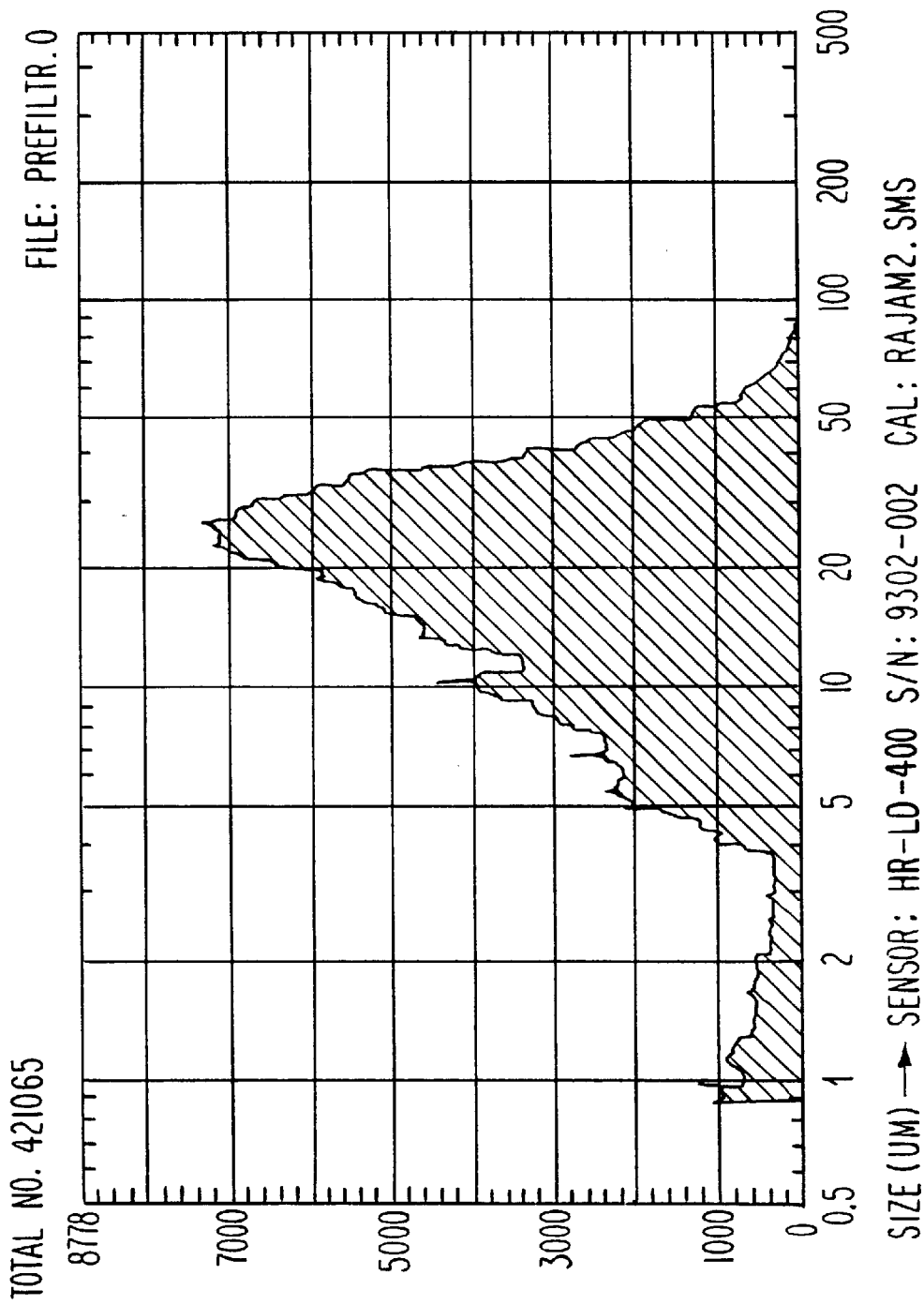
FIG. 16 graphically depicts the size distribution of gaseous precursor-filled liposomes of the invention before (A) and after (B) filtration through a set of cascade filters of 10 mm and 5 mm.
Figure 16B:
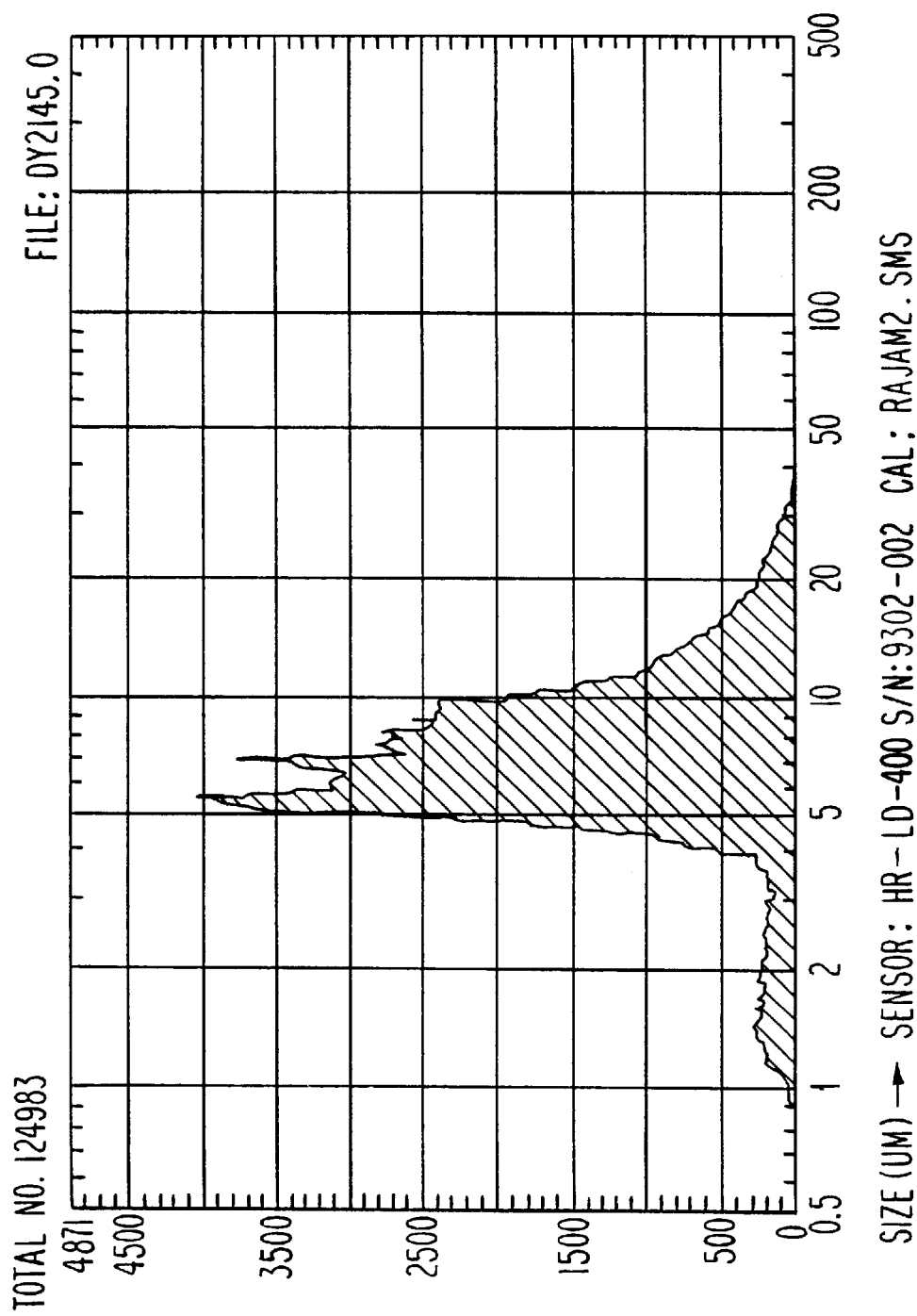

Filtration is preferably carried out in order to obtain gaseous precursor-filled liposomes of a substantially uniform size. In certain preferred embodiments, the filtration assembly contains more than one filter, and preferably, the filters are not immediately adjacent to each other, as illustrated in FIG. 12. Before filtration, the gaseous precursor-filled liposomes range in size from about 1 micron to greater than 60 microns (FIGS. 15A and 16A). After filtration through a single filter, the gaseous precursor-filled liposomes are generally less than 10 microns but particles as large as 25 microns in size remain. After filtration through two filters (10 micron followed by 8 micron filter), almost all of the liposomes are less than 10 microns, and most are 5 to 7 microns (FIGS. 15B and 16B).

As shown in FIG. 9, filtering may be accomplished by incorporating a filter element 72 directly onto the end of the extraction tube 67 so that only gaseous precursor-filled liposomes below a pre-determined size are extracted from the mixing vessel 66. Alternatively, or in addition to the extraction tube filter 72, gaseous precursor-filled liposome sizing may be accomplished by means of a filter 80 incorporated into the conduit 79 that directs the gaseous precursor-filled liposomes 77 from the extraction vessel 76 to the vials 82, as shown in FIG. 9. The filter 80 may contain a cascade filter assembly 124, such as that shown in FIG. 12. The cascade filter assembly 124 shown in FIG. 12 comprises two successive filters 116 and 120, with filter 120 being disposed upstream of filter 116. In a preferred embodiment, the upstream filter 120 is a "NUCLEPORE" 10 µm filter and the downstream filter 116 is a "NUCLEPORE" 8 µm filter. Two 0.15 mm metallic mesh discs 115 are preferably installed on either side of the filter 116. In a preferred embodiment, the filters 116 and 120 are spaced apart a minimum of 150 µm by means of a Teflon™ O-ring, 118.

In addition to filtering, sizing may also be accomplished by taking advantage of the dependence of gaseous precursor-filled liposome buoyancy on size. The gaseous precursor-filled liposomes have appreciably lower density than water and hence will float to the top of the mixing vessel 66. Since the largest liposomes have the lowest density, they will float most quickly to the top. The smallest liposomes will generally be last to rise to the top and the non gaseous precursor-filled lipid portion will sink to the bottom. This phenomenon may be advantageously used to size the gaseous precursor-filled liposomes by removing them from the mixing vessel 66 via a differential flotation process. Thus, the setting of the vertical location of the extraction tube 66 within the mixing vessel 66 may control the size of the gaseous precursor-filled liposomes extracted; the higher the tube, the larger the gaseous precursor-filled liposomes extracted. Moreover, by periodically or continuously adjusting the vertical location of the extraction tube 67 within the mixing vessel 66, the size of the gaseous precursor-filled liposomes extracted may be controlled on an on-going basis. Such extraction may be facilitated by incorporating a device 68, which may be a threaded collar 71 mating with a threaded sleeve 72 attached to the extraction tube 67, that allows the vertical location of the extraction tube 67 within the extraction vessel 66 to be accurately adjusted.

The gel state shaking gaseous precursor installation process itself may also be used to improve sizing of the gaseous precursor-filled lipid based microspheres. In general, the greater the intensity of the shaking energy, the smaller the size of the resulting gaseous precursor-filled liposomes.

The current invention also includes novel methods for preparing therapeutic-containing temperature activated gaseous precursor-filled liposomes to be dispensed to the ultimate user. Once gaseous precursor-filled liposomes are formed, they can not be sterilized by heating at a temperature that would cause rupture. Therefore, it is desirable to form the gaseous precursor-filled liposomes from sterile ingredients and to perform as little subsequent manipulation as possible to avoid the danger of contamination. According to the current invention, this may be accomplished, for example, by sterilizing the mixing vessel containing the lipid and aqueous solution before shaking and dispensing the gaseous precursor-filled liposomes 77 from the mixing vessel 66, via the extraction vessel 76, directly into the barrel 104 of a sterile syringe 100, shown in FIG. 10, without further processing or handling; that is, without subsequent sterilization. The syringe 100, charged with gaseous precursor-filled liposomes 77 and suitably packaged, may then be dispensed to the ultimate user. Thereafter, no further manipulation of the product is required in order to administer the gaseous precursor-filled liposomes to the patient, other than removing the syringe from its packaging and removing a protector (not shown) from the syringe needle 102 and inserting the needle into the body of the patient, or into a catheter. Moreover, the pressure generated when the syringe plunger 106 is pressed into the barrel 104 will cause the largest gaseous precursor-filled liposomes to collapse, thereby achieving a degree of sizing without filtration. Upon entering the patient's body, at the precursor phase transition temperature, the gaseous precursor-filled liposomes become gas-filled liposomes. Alternatively, this method may be performed at the phase transition temperature of the precursor such that gas-filled liposomes are administered to the patient.

Where it is desired to filter the gaseous precursor-filled liposomes at the point of use, for example because they are removed from the extraction vessel 76 without filtration or because further filtration is desired, the syringe 100 may be fitted with its own filter 108, as shown in FIG. 10. This results in the gaseous precursor-filled liposomes being sized by causing them to be extruded through the filter 108 by the action of the plunger 106 when the gaseous precursor-filled liposomes are injected. Thus, the gaseous precursor-filled liposomes may be sized and injected into a patient in one step.

Figure 1:
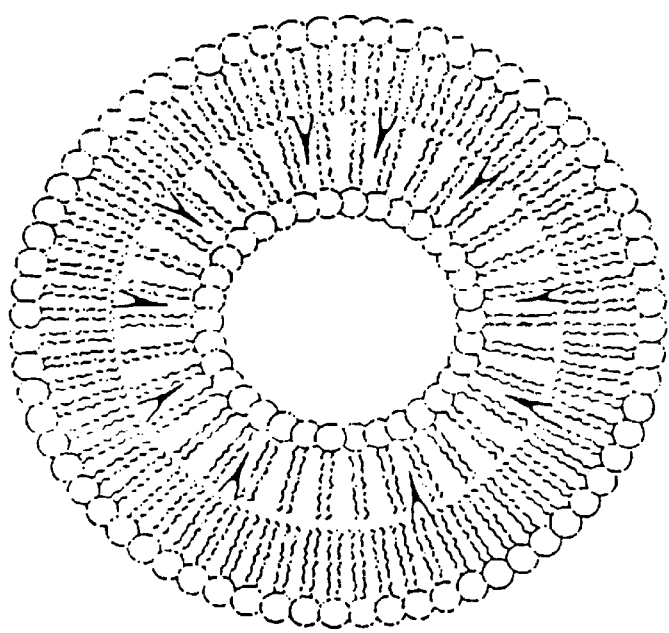
FIG. 1 is a diagrammatical representation of two liposomes. The upper liposome is a gaseous precursor-filled liposome having a therapeutic membrane embedded hydrophobic drug compound indicated by the blackened arrow heads, embedded within the wall of a liposome microsphere, and the lower liposome shows the subsequent release of the therapeutic upon the application of ultrasound.
Figure 1:
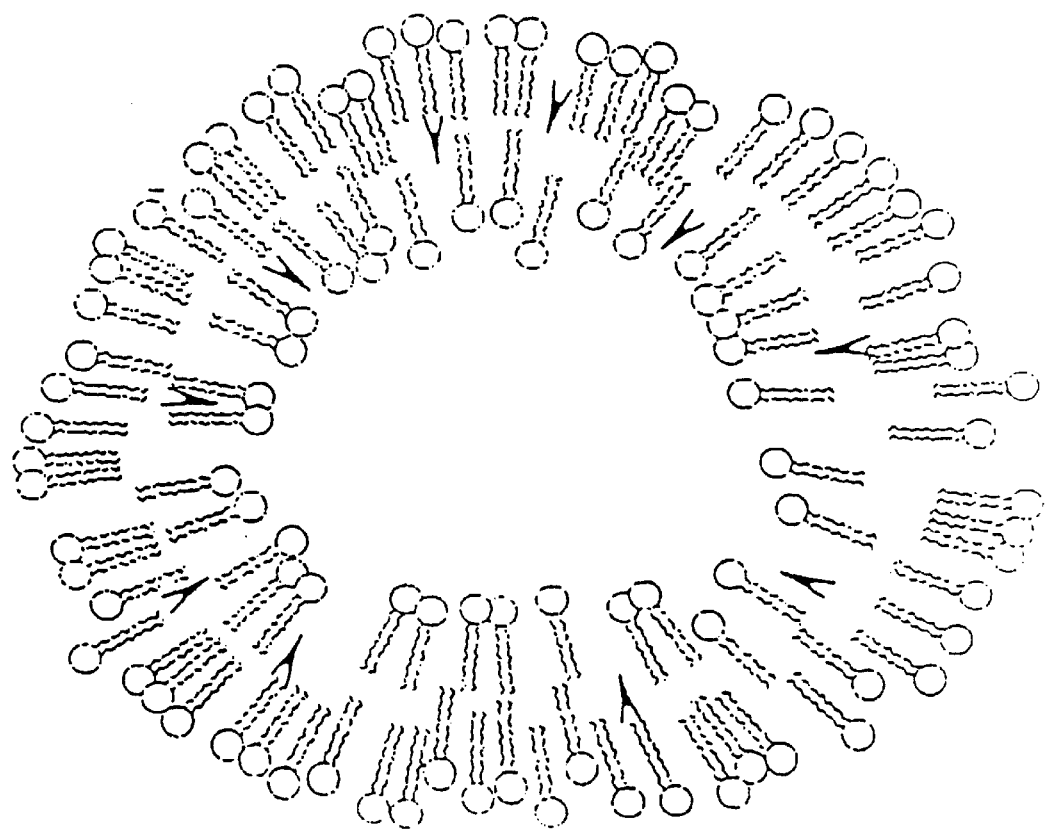
Figure 2:
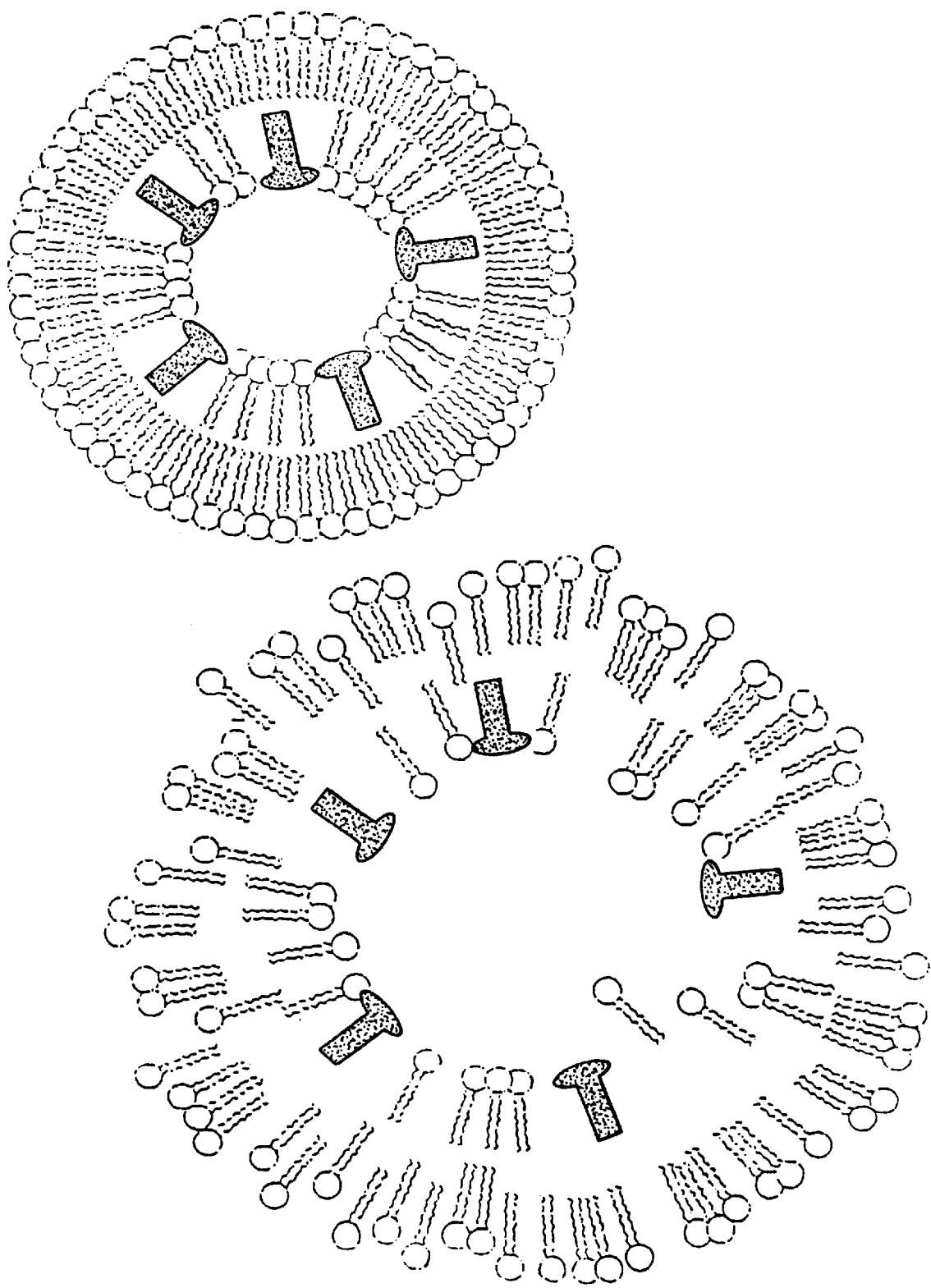
FIG. 2 is a diagrammatical depiction of two liposomes. The upper liposome is a gaseous precursor-filled liposome having a therapeutic membrane bound aliphatic drug compound, indicated by the shaded members, embedded within the inner layer of the wall of a liposome microsphere, and exposed to the gaseous precursor-filled interior, and the lower liposome shows the subsequent release of the therapeutic upon the application of ultrasound.
Figure 3:
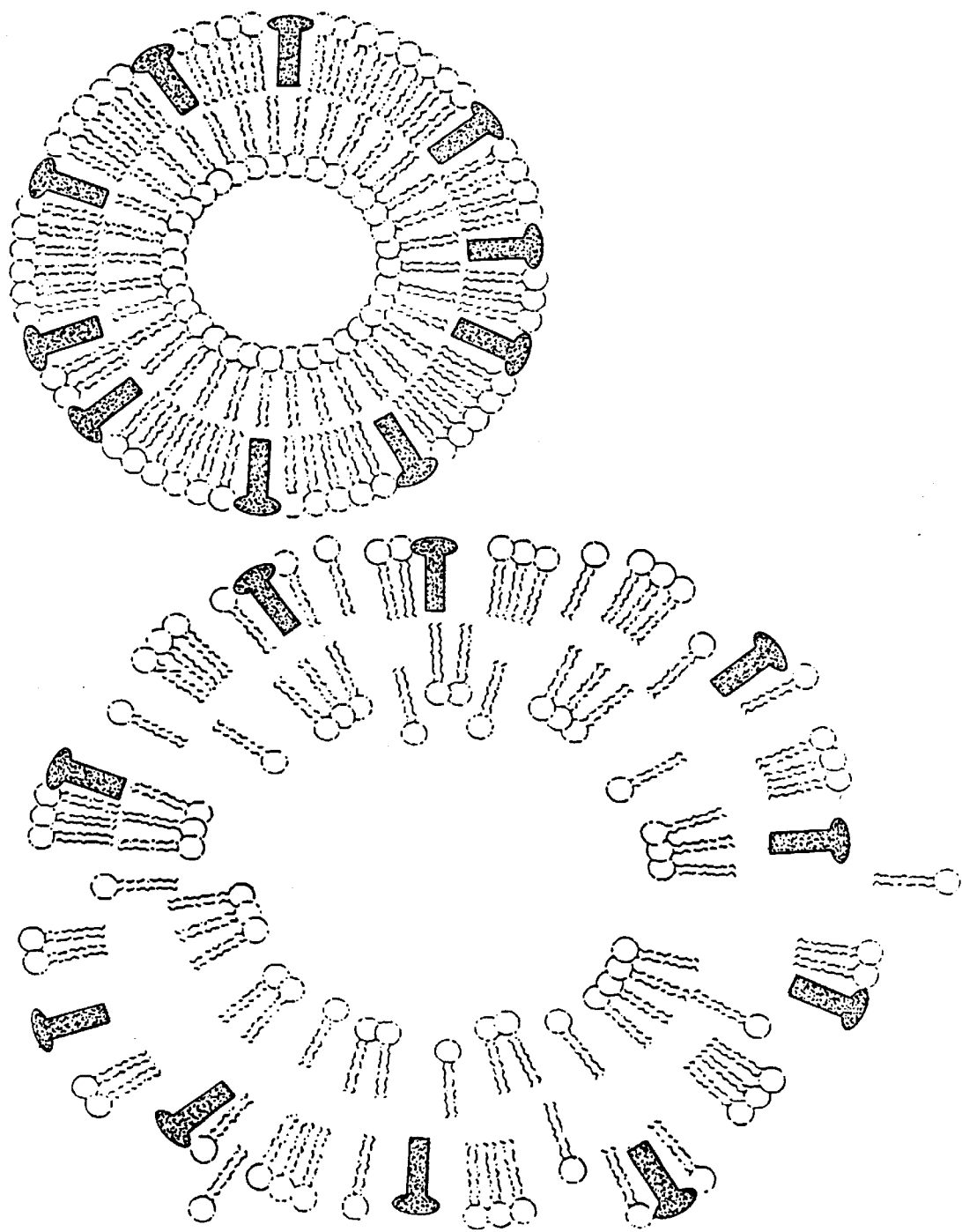
FIG. 3 is a diagrammatical illustration of two liposomes. The upper liposome is a gaseous precursor-filled liposome having a therapeutic membrane bound aliphatic drug compound, indicated by the shaded members, embedded within the outer layer of the wall of a liposome microsphere, and exposed to the gaseous precursor-filled interior, and the lower liposome shows the subsequent release of the therapeutic upon the application of ultrasound.
Figure 4:
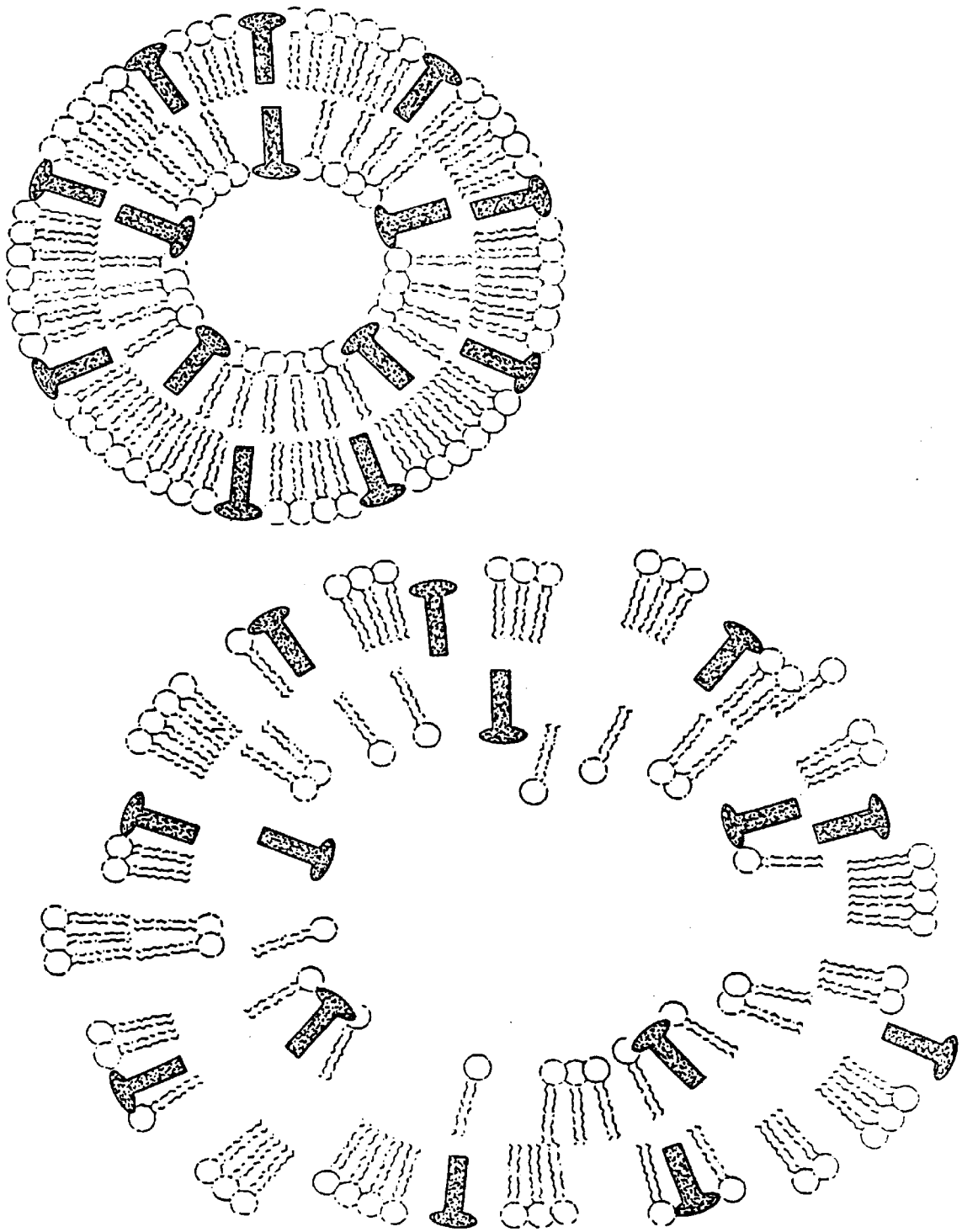
FIG. 4 is a diagrammatical representation of two liposomes. The upper liposome is a gaseous precursor-filled liposome microsphere having a therapeutic membrane bound aliphatic drug compound, indicated by the shaded members, embedded within the inner and outer layers of the wall of a liposome microsphere, and exposed to both the internal gaseous precursor-filled void, and the exterior environment, and the lower liposome shows the subsequent release of the therapeutic upon the application of ultrasound.

In order to accommodate the use of a single or dual filter in the hub housing of the syringe, a non-standard syringe with hub housing is necessary. As shown in FIG. 3, the hub that houses the filter(s) are of a dimension of approximately 1 cm to approximately 2 cm in diameter by about 1.0 cm to about 3.0 cm in length with an inside diameter of about 0.8 cm for which to house the filters. The abnormally large dimensions for the filter housing in the hub are to accommodate passage of the microspheres through a hub with sufficient surface area so as to decrease the pressure that need be applied to the plunger of the syringe. In this manner, the microspheres will not be subjected to an inordinately large pressure head upon injection, which may cause rupture of the microspheres.

As shown in FIG. 11, a cascade filter housing 110 may be fitted directly onto a syringe 112, thereby allowing cascade filtration at the point of use. As shown in FIG. 12, the filter housing 110 is comprised of a cascade filter assembly 124, previously discussed, incorporated between a lower collar 122, having male threads, and a female collar 114, having female threads. The lower collar 122 is fitted with a Luer lock that allows it to be readily secured to the syringe 112 and the upper collar 114 is fitted with a needle 102.

In preferred embodiments, the lipid solution is extruded through a filter and the lipid solution is heat sterilized prior to shaking. Once gaseous precursor-filled liposomes are formed, they may be filtered for sizing as described above. These steps prior to the formation of gaseous precursor-filled liposomes provide the advantages, for example, of reducing the amount of unhydrated lipid and thus providing a significantly higher yield of gaseous precursor-filled liposomes, as well as and providing sterile gaseous precursor-filled liposomes ready for administration to a patient. For example, a mixing vessel such as a vial or syringe may be filled with a filtered lipid suspension, and the solution may then be sterilized within the mixing vessel, for example, by autoclaving. Gaseous precursor may be instilled into the lipid suspension to form gaseous precursor-filled liposomes by shaking the sterile vessel. Preferably, the sterile vessel is equipped with a filter positioned such that the gaseous precursor-filled liposomes pass through the filter before contacting a patient.

Figure 17A:
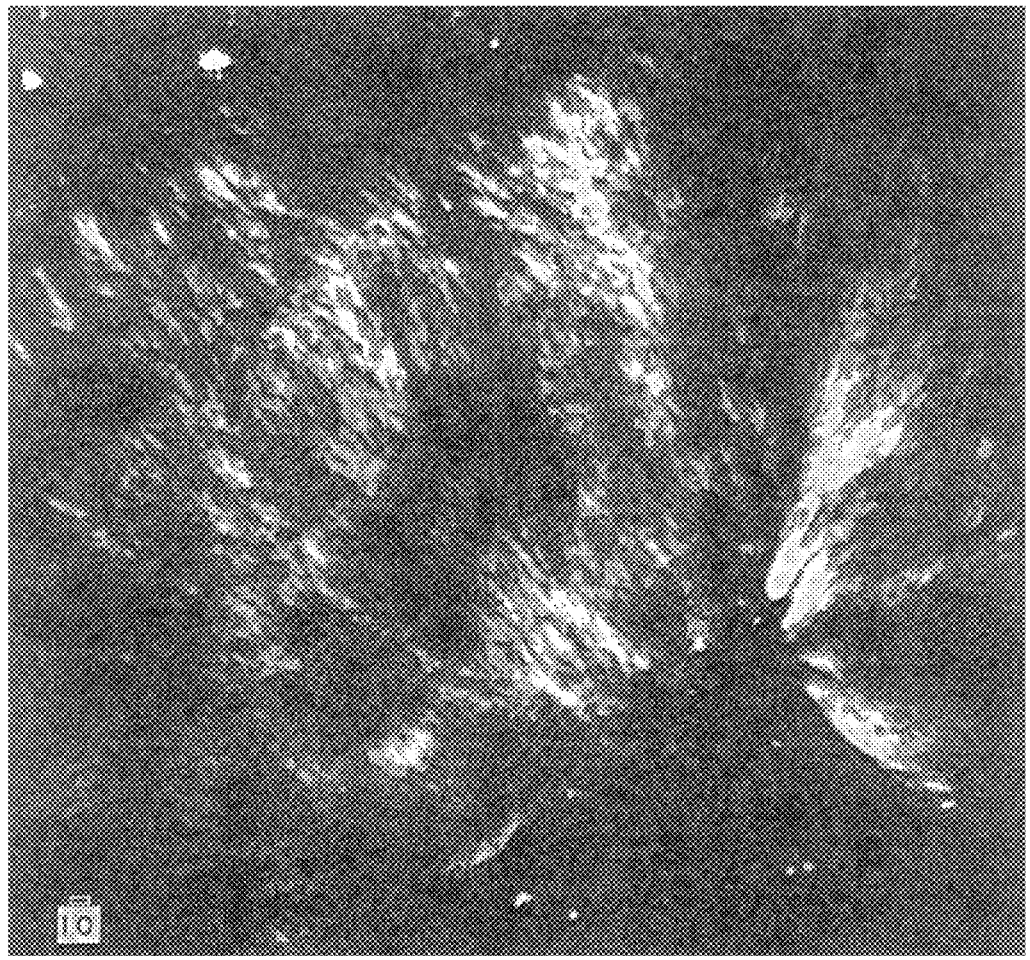
FIG. 17 is a micrograph of a lipid suspension before (A) and after (B) extrusion through a filter. The scale bar is 10 mm.
Figure 17B:
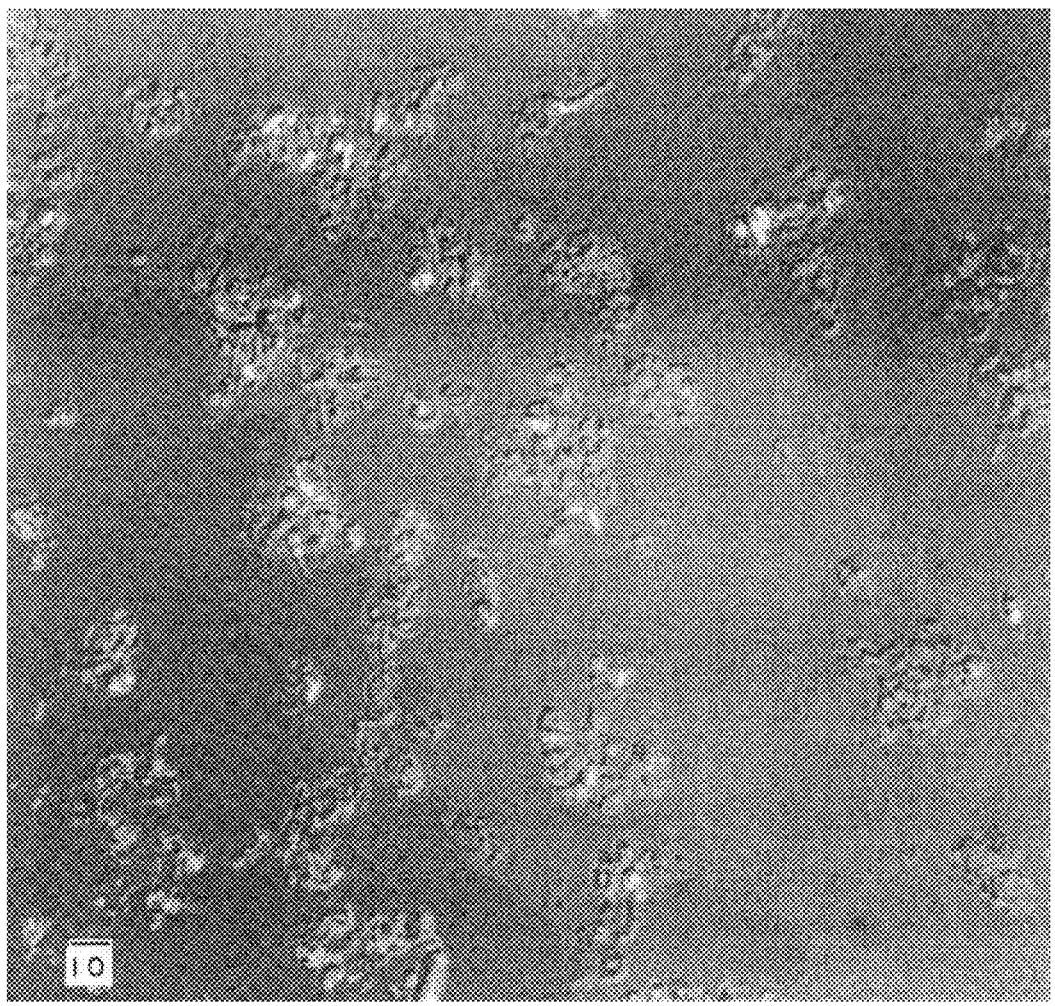

The first step of this preferred method, extruding the lipid solution through a filter, decreases the amount of unhydrated lipid by breaking up the dried lipid and exposing a greater surface area for hydration. Preferably, the filter has a pore size of about 0.1 to about 5 μm, more preferably, about 0.1 to about 4 μm, even more preferably, about 0.1 to about 2 μm, and most preferably, about 1 μm. As shown in FIG. 17, when a lipid suspension is filtered (FIG. 17B), the amount of unhydrated lipid is reduced when compared to a lipid suspension that was not pre-filtered (FIG. 17A). Unhydrated lipid appears as amorphous clumps of non-uniform size and is undesirable.

The second step, sterilization, provides a composition that may be readily administered to a patient. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., even more preferably, about 120° C. to about 130° C., and most preferably, about 130° C. Preferably, heating occurs for at least about 1 minute, more preferably, about 1 to about 30 minutes, even more preferably, about 10 to about 20 minutes, and most preferably, about 15 minutes.

Where sterilization occurs by a process other than heat sterilization at a temperature which would cause rupture of the gaseous precursor-filled liposomes, sterilization may occur subsequent to the formation of the gaseous precursor-filled liposomes, and is preferred. For example, gamma radiation may be used before and/or after gaseous precursor-filled liposomes are formed.

Sterilization of the gaseous precursor may be achieved via passage through a 0.22 μm filter or a smaller filter, prior to emulsification in the aqueous media. This can be easily achieved via sterile filtration of the contents directly into a vial which contains a predetermined amount of likewise sterilized and sterile-filled aqueous carrier.

Figure 18A:
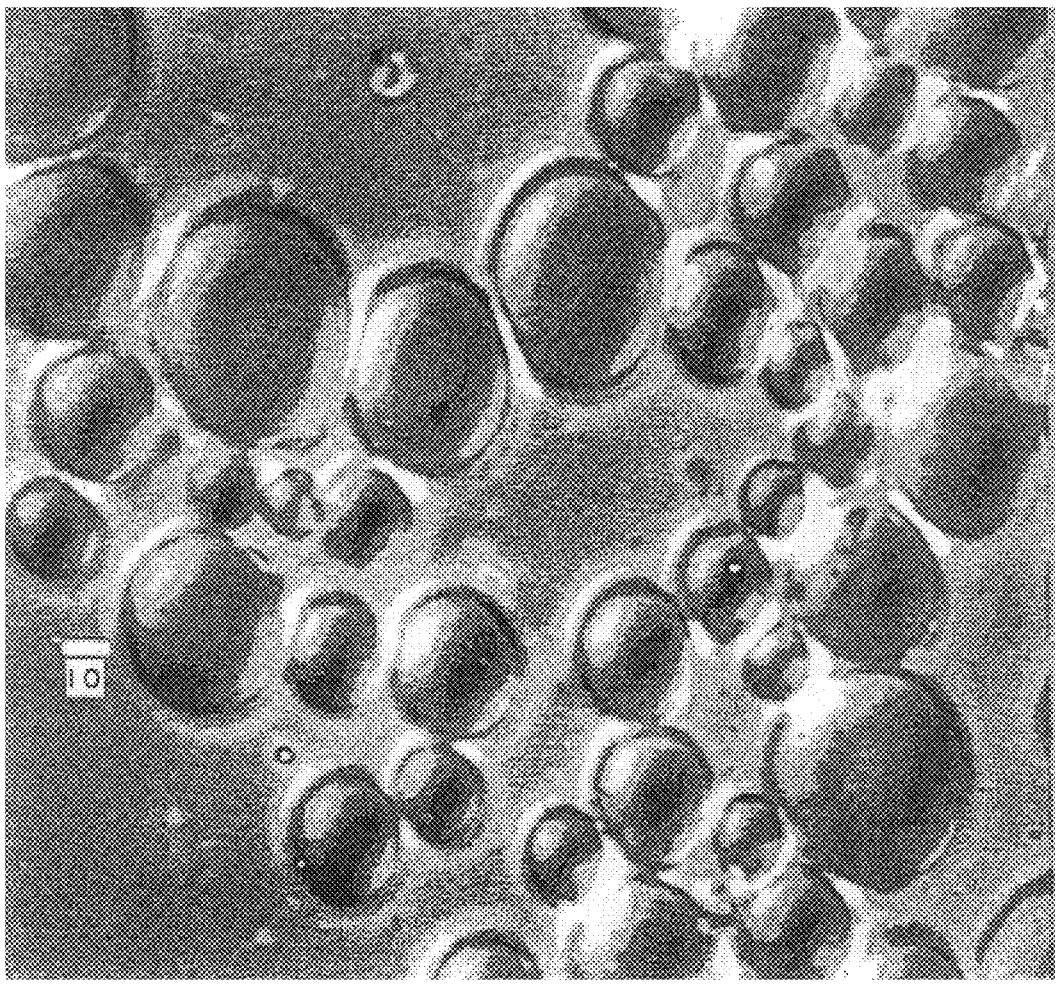
FIG. 18 is a micrograph of gaseous precursor-filled liposomes formed subsequent to filtering and autoclaving a lipid suspension, the micrographs having been taken before (A) and after (B) sizing by filtration of the gaseous precursor-filled liposomes.
Figure 18B:
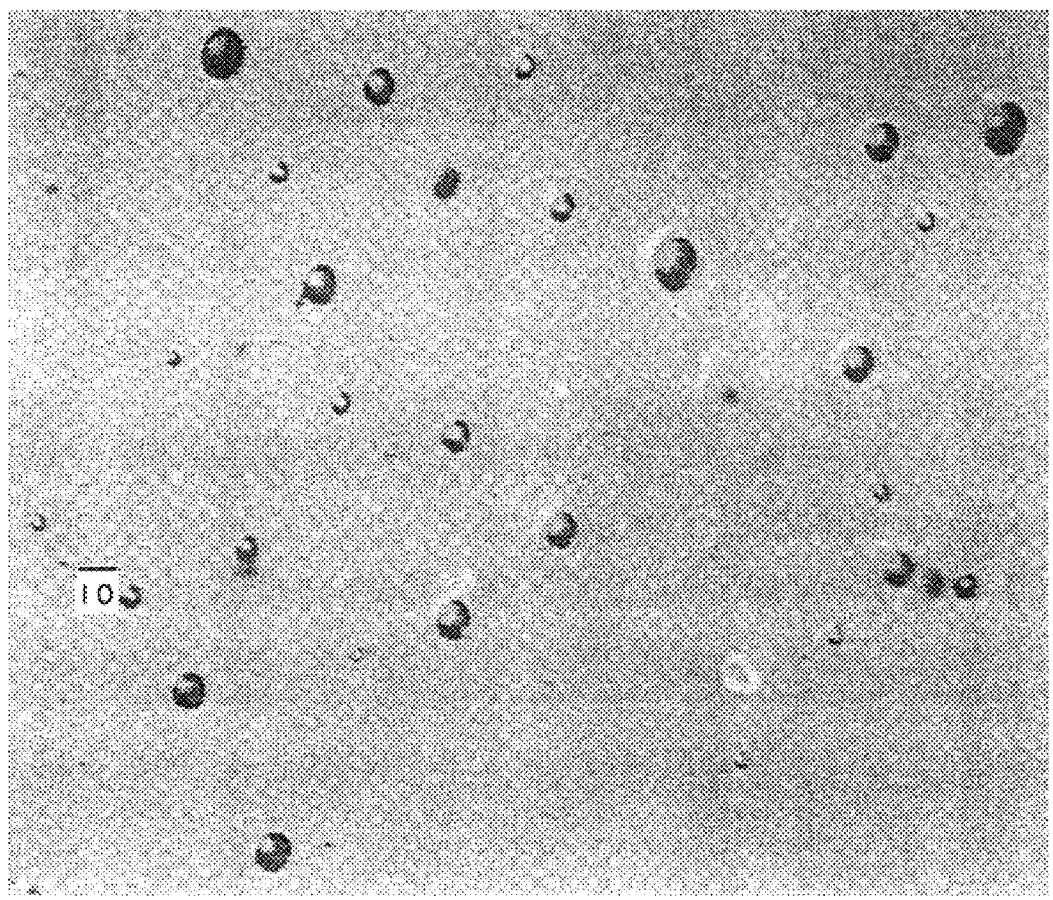

FIG. 18 illustrates the ability of gaseous precursor-filled liposomes to successfully form after autoclaving, which was carried out at 130° C. for 15 minutes, followed by vortexing for 10 minutes. Further, after the extrusion and sterilization procedure, the shaking step yields gaseous precursor-filled liposomes with little to no residual anhydrous lipid phase. FIG. 18A shows gaseous precursor-filled liposomes generated after autoclaving but prior to filtration, thus resulting in a number of gaseous precursor-filled liposomes having a size greater than 10 μm. FIG. 18B shows gaseous precursor-filled liposomes after a filtration through a 10 μm "NUCLEPORE" filter, resulting in a uniform size around 10 μm.

Certain embodiments of the present invention are directed to therapeutic delivery systems comprising gas-filled liposomes prepared by vacuum drying gas instillation methods and having encapsulated therein a therapeutic (that is, contrast agent or drug containing), such liposomes sometimes being refereed to herein as therapeutic containing vacuum dried gas instilled liposomes. The present invention is further directed to therapeutic delivery systems comprising therapeutic-containing gas-filled liposomes substantially devoid of liquid in the interior thereof. This method is performed at the phase transition temperature of the gaseous precursor, wherein the gas is thus provided by a gaseous precursor. The liquid precursor becomes a gas which is instilled into the liposomes at the transition temperature.

This method for preparing the liposomes of the subject invention comprises: (i) placing liposomes encapsulating a therapeutic under negative pressure; (ii) incubating the liposomes under the negative pressure for a time sufficient to remove substantially all water from the liposomes; and (iii) instilling selected gas into the liposomes until ambient pressures are achieved. Methods employing the foregoing steps are referred to herein as the vacuum drying gas instillation methods for preparing drug containing liposomes.

Apparatus is also provided for preparing the liposomes of the invention using the vacuum drying gas instillation methods, said apparatus comprising: (i) a vessel containing liposomes having encapsulated therein a therapeutic; (ii) means for applying negative pressure to the vessel to draw water from the liposomes contained therein; (iii) a conduit connecting the negative pressurizing means to the vessel, the conduit directing the flow of said water; and (iv) means for introducing a gas into the liposomes in the vessel.

The vacuum drying gas instillation method employed to prepare both the subject gas-filled liposomes prepared by the vacuum drying gas instillation method, and the gas-filled liposomes substantially devoid of water in the interior thereof, contemplates the following process. First, in accordance with the process, the therapeutic containing liposomes are placed under negative pressure (that is, reduced pressure or vacuum conditions). Next, the liposomes are incubated under that negative pressure for a time sufficient to remove substantially all water from the liposomes, thereby resulting in substantially dried liposomes. By removal of substantially all water, and by substantially dried liposomes, as those phrases are used herein, it is meant that the liposomes are at least about 90% devoid of water, preferably at least about 95% devoid of water, most preferably about 100% devoid of water. Although the water is removed, the therapeutic, with its higher molecular weight, remains behind, encapsulated in the liposome. Finally, the liposomes are instilled with selected gas by applying the gas to the liposomes until ambient pressures are achieved, thus resulting in the subject therapeutic containing vacuum dried gas instilled liposomes of the present invention, and the therapeutic containing gas-filled liposomes of the invention substantially devoid of water in the interior thereof. By substantially devoid of water in the interior thereof, as used herein, it is meant liposomes having an interior that is at least about 90% devoid of water, preferably at least about 95% devoid of water, most preferably about 100% devoid of water.

Unexpectedly, the therapeutic containing liposomes prepared in accordance with the methods of the present invention possess a number of surprising yet highly beneficial characteristics. The liposomes of the invention exhibit intense echogenicity on ultrasound, will rupture on application of peak resonant frequency ultrasound (as well as other resonant frequencies of sufficient intensity and duration), are highly stable to pressure, and/or generally possess a long storage life, either when stored dry or suspended in a liquid medium. The gaseous precursor-filled liposomes also have the advantages, for example, of stable particle size, low toxicity and compliant membranes. It is believed that the flexible membranes of the gaseous precursor-filled liposomes may be useful in aiding the accumulation or targeting of these liposomes to tissues such as tumors. Also unexpected is the ability of the liposomes during the vacuum drying gas instillation process to fill with gas and resume their original circular shape, rather than irreversibly collapse into a cup-like shape.

Figure 13:
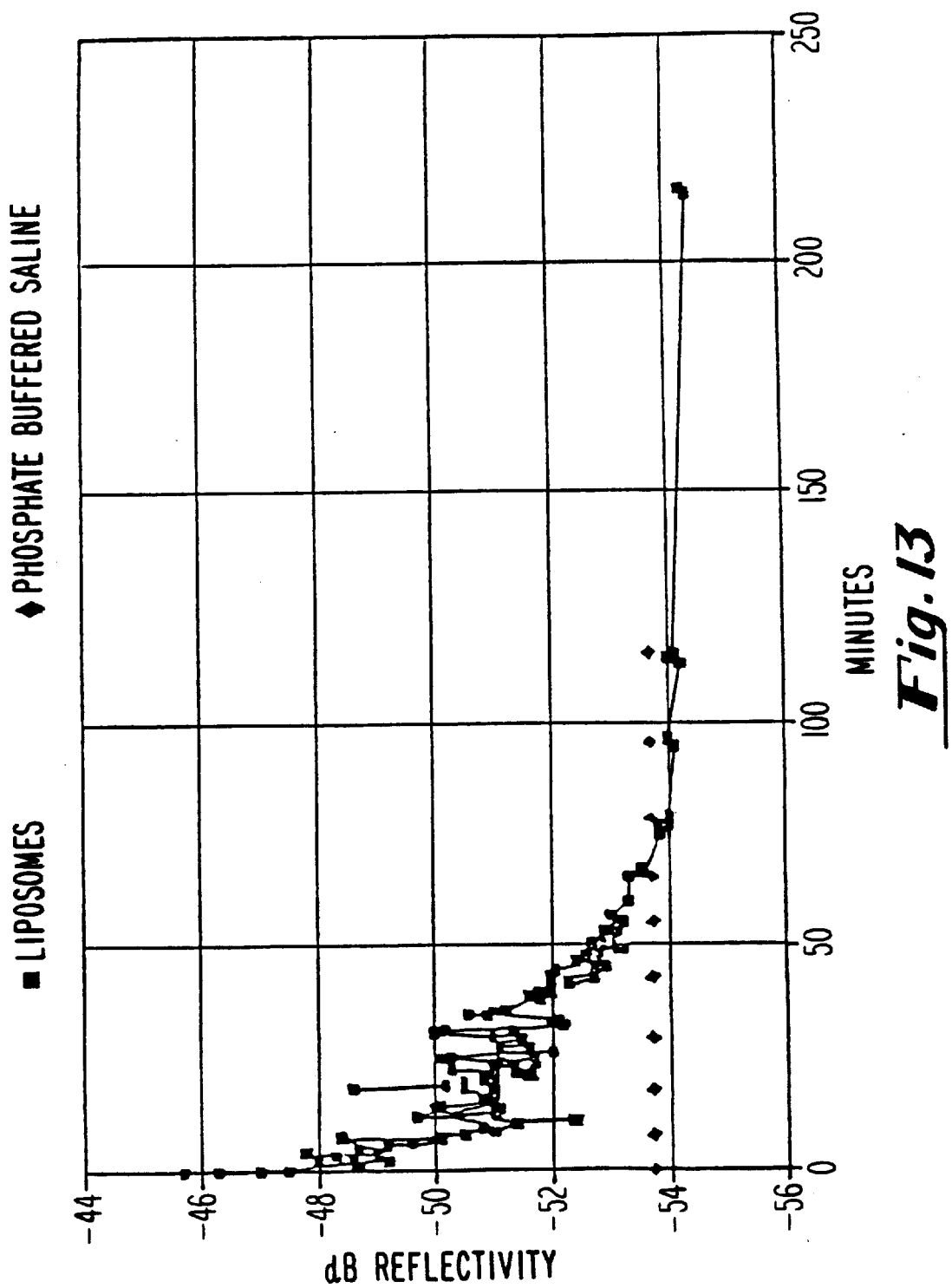
FIG. 13 is a graphical representation of the dB reflectivity of gas-filled liposomes substantially devoid of water in the interior thereof prepared by the vacuum drying gas instillation method, without any drugs encapsulated therein. The data was obtained by scanning with a 7.5 megahertz transducer using an Acoustic Imaging™ Model 5200 scanner (Acoustic Imaging, Phoenix, Ariz.), and was generated by using the system test software to measure reflectivity. The system was standardized prior to each experiment with a phantom of known acoustic impedance.

The echogenicity of the liposomes and the ability to rupture the liposomes at the peak resonant frequency using ultrasound permits the controlled delivery of therapeutics to a region of a patient by allowing the monitoring of the liposomes following administration to a patient to determine the transition from liquid precursor to gas, the presence of liposomes in a desired region, and the rupturing of the liposomes using ultrasound to release the therapeutics in the region. Preferably, the liposomes of the invention possess a reflectivity of greater than 2 dB, preferably between about 4 dB and about 20 dB. Within these ranges, the highest reflectivity for the liposomes of the invention is exhibited by the larger liposomes, by higher concentrations of liposomes, and/or when higher ultrasound frequencies are employed. See FIG. 13, which is a graphical representation of the dB reflectivity of gas-filled liposomes substantially devoid of water in the interior thereof prepared by the vacuum drying gas instillation method, without any drugs encapsulated therein. Preferably, the liposomes of the invention have a peak resonant frequency of between about 0.5 mHz and about 10 mHz. Of course, the peak resonant frequency of the gaseous precursor-filled and gas-filled liposomes of the invention will vary depending on the diameter and, to some extent, the elasticity of the liposomes, with the larger and more elastic liposomes having a lower resonant frequency than the smaller and more elastic liposomes.

The stability of the liposomes of the invention is also of great practical importance. The subject liposomes tend to have greater stability during storage than conventional liquid, aqueous, and/or gas-filled liposomes produced via known procedures such as pressurization or other techniques. At 72 hours after formation, for example, conventionally prepared gas containing liposomes often are essentially devoid of gas, the gas having diffused out of the liposomes and/or the liposomes having ruptured and/or fused, resulting in a concomitant loss in reflectivity. In comparison, therapeutic containing gaseous precursor-filled liposomes of the present invention generally have a shelf life stability of greater than about three weeks, preferably a shelf life stability of greater than about four weeks, more preferably a shelf life stability of greater than about five weeks, even more preferably a shelf life stability of greater than about three months, and often a shelf life stability that is even much longer, such as over six months, twelve months, or even two years.

Also unexpected is the ability of the liposomes during the vacuum drying gas instillation process to fill with gas and resume their original circular shape, rather than collapse into a cup-shaped structure, as the prior art would cause one to expect. See, e.g., Crowe et al., *Archives of Biochemistry and Biophysics,* Vol. 242, pp. 240–247 (1985); Crowe et al., *Archives of Biochemistry and Biophysics,* Vol. 220, pp. 477–484 (1983); Fukuda et al., *J. Am. Chem. Soc.,* Vol. 108, pp. 2321–2327 (1986); Regen et al., *J. Am. Chem. Soc.,* Vol. 102, pp. 6638–6640 (1980).

The therapeutic containing liposomes subjected to the vacuum drying gas instillation method of the invention may be prepared using any one of a variety of conventional liposome preparatory techniques which will be apparent to those skilled in the art. Although any of a number of varying techniques can be employed, preferably the therapeutic containing liposomes are prepared via microemulsification techniques. The liposomes produced by the various conventional procedures can then be employed in the vacuum drying gas instillation method of the present invention, to produce the therapeutic containing liposomes of the present invention.

The materials which may be utilized in preparing liposomes to be employed in the vacuum drying gas instillation method of the present invention include any of the materials or combinations thereof known to those skilled in the art as suitable for liposome construction.

Liposomes may be prepared prior to gas instillation using any one of a variety of conventional liposome preparatory techniques which will be apparent to those skilled in the art. These techniques include freeze-thaw, as well as techniques such as sonication, chelate dialysis, homogenization, solvent infusion, microemulsification, spontaneous formation, solvent vaporization, French pressure cell technique, controlled detergent dialysis, and others, each involving preparing the liposomes in various fashions in a solution containing the desired therapeutic so that the therapeutic is encapsulated in, enmeshed in, or attached the resultant liposome. Alternatively, therapeutics may be loaded into the liposomes using pH gradient techniques which, as those skilled in the art will recognize, is particularly applicable to therapeutics which either proteinate or deproteinate at a particular pH. See, e.g., Madden et al., *Chemistry and Physics of Lipids,* 1990 53, 37–46, the disclosures of which are hereby incorporated herein by reference in their entirety.

To prepare the therapeutic containing liposomes for vacuum drying gas installation, and by way of general guidance, dipalmitoylphosphatidylcholine liposomes, for example, may be prepared by suspending dipalmitoylphosphatidylcholine lipids in phosphate buffered saline or water containing the therapeutic to be encapsulated, and heating the lipids to about 50° C., a temperature which is slightly above the 41° C. temperature required for transition of the dipalmitoylphosphatidylcholine lipids from a gel state to a liquid crystalline state, to form therapeutic containing liposomes.

To prepare multilamellar vesicles of a rather heterogeneous size distribution of around 2 microns, the liposomes may then be mixed gently by hand while keeping the liposome solution at a temperature of about 50° C. The temperature is then lowered to room temperature, and the liposomes remain intact. Extrusion of dipalmitoylphosphatidylcholine liposomes through polycarbonate filters of defined size may, if desired, be employed to make liposomes of a more homogeneous size distribution. A device useful for this technique is an extruder device (Extruder Device™, Lipex Biomembranes, Vancouver, Canada) equipped with a thermal barrel so that extrusion may be conveniently accomplished above the gel state to liquid crystalline state phase transition temperature for lipids.

For lipophilic therapeutics which are sparingly soluble in aqueous media, such therapeutics may be mixed with the lipids themselves prior to forming the liposomes. For example, amphotericin may be suspended with the dried lipids (e.g., 8:2 molar ratio of egg phosphatidylcholine and cholesterol in chloroform and mixed with the lipids). The chloroform is then evaporated (note that other suitable organic solvents may also be used, such as ethanol or ether) and the dried lipids containing a mixture of the lipophilic therapeutics are then resuspended in aqueous media, e.g., sterile water or physiologic saline. This process may be used for a variety of lipophilic therapeutics such as corticosteroids to incorporate lipophilic drugs into the liposome membranes. The resulting liposomes are then dried, subjected to the vacuum gas instillation method as described above.

Alternatively, and again by way of general guidance, conventional freeze-thaw procedures may be used to produce either oligolamellar or unilamellar dipalmitoylphosphatidylcholine liposomes. After the freeze-thaw procedures, extrusion procedures as described above may then be performed on the liposomes.

The therapeutic containing liposomes thus prepared may then be subjected to the vacuum drying gas instillation process of the present invention, to produce the therapeutic containing vacuum dried gas instilled liposomes, and the therapeutic containing temperature activated gaseous precursor-filled liposomes substantially devoid of water in the interior thereof, of the invention. In accordance with the process of the invention, the therapeutic containing liposomes are placed into a vessel suitable for subjecting to the liposomes to negative pressure (that is, reduced pressure or vacuum conditions). Negative pressure is then applied for a time sufficient to remove substantially all water from the liposomes, thereby resulting in substantially dried liposomes. As those skilled in the art would recognize, once armed with the present disclosure, various negative pressures can be employed, the important parameter being that substantially all of the water has been removed from the liposomes. Generally, a negative pressure of at least about 700 mm Hg and preferably in the range of between about 700 mm Hg and about 760 mm Hg (gauge pressure) applied for about 24 to about 72 hours, is sufficient to remove substantially all of the water from the liposomes. Other suitable pressures and time periods will be apparent to those skilled in the art, in view of the disclosures herein.

Finally, a selected gas is applied to the liposomes to instill the liposomes with gas until ambient pressures are achieved, thereby resulting in the drug containing vacuum dried gas instilled liposomes of the invention, and in the drug containing gaseous precursor-filled liposomes substantially devoid of water in the interior thereof. Preferably, gas instillation occurs slowly, that is, over a time period of at least about 4 hours, most preferably over a time period of between about 4 and about 8 hours.

Various biocompatible gases may be employed. Such gases include air, nitrogen, carbon dioxide, oxygen, argon, xenon, neon, helium, or any and all combinations thereof. Other suitable gases will be apparent to those skilled in the art, the gas chosen being only limited by the proposed application of the liposomes. In addition to the gaseous precursors disclosed herein, the precursors may be co-entrapped with other gases. For example, during the transition from the gaseous precursor to a gas in an enclosed environment containing ambient gas (as air), the two gases may mix and upon agitation and formation of microspheres, the gaseous content of the microspheres results in a mixture of two or more gases, dependent upon the densities of the gases mixed.

The above described method for production of liposomes is referred to hereinafter as the vacuum drying gas instillation process.

If desired, the liposomes may be cooled, prior to subjecting the liposomes to negative pressure, and such cooling is preferred. Preferably, the liposomes are cooled to below 0° C., more preferably to between about −10° C. and about −20° C., and most preferably to −10° C., prior to subjecting the liposomes to negative pressure. Upon reaching the desired negative pressure, the liposomes temperature is then preferably increased to above 0° C., more preferably to between about 10° C. and about 20° C., and most preferably to 10° C., until substantially all of the water has been removed from the liposomes and the negative pressure is discontinued, at which time the temperature is then permitted to return to room temperature.

If the liposomes are cooled to a temperature below 0° C., it is preferable that the vacuum drying gas instillation process be carried out with liposomes either initially prepared in the presence of cryoprotectants, or liposomes to which cryoprotectants have been added prior to carrying out the vacuum drying gas instillation process of the invention. Such cryoprotectants, while not mandatorily added, assist in maintaining the integrity of liposome membranes at low temperatures, and also add to the ultimate stability of the membranes. Preferred cryoprotectants are trehalose, glycerol, polyethyleneglycol (especially polyethyleneglycol of molecular weight 400), raffinose, sucrose and sorbitol, with trehalose and propylene glycol being particularly preferred.

It has also been surprisingly discovered that the liposomes of the invention are highly stable to changes in pressure. Because of this characteristic, extrusion of the liposomes through filters of defined pore size following vacuum drying and gas instillation can be carried out, if desired, to create liposomes of relatively homogeneous and defined pore size.

Figure 14:
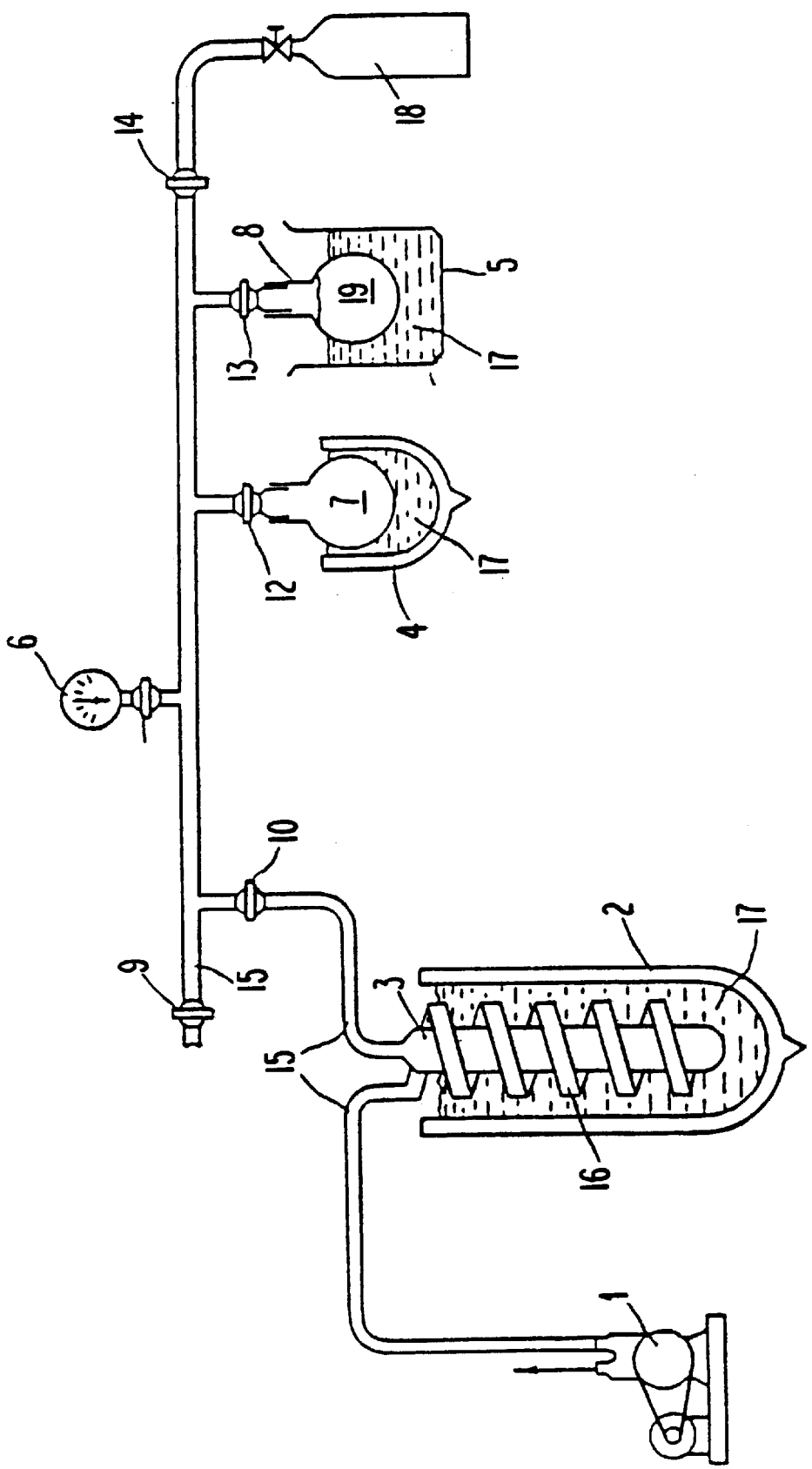
FIG. 14 shows a preferred apparatus for preparing the drug containing vacuum dried gas instilled liposomes, and the drug containing gas-filled liposomes substantially devoid of water in the interior thereof prepared by the vacuum drying gas instillation method.

As another aspect of the invention, useful apparatus for preparing the therapeutic containing vacuum dried gas instilled liposomes, and the therapeutic containing gas-filled liposomes substantially devoid of water in the interior thereof, of the invention is also presented. Specifically, there is shown in FIG. 14 a preferred apparatus for vacuum drying liposomes and instilling a gas into the dried liposomes. The apparatus is comprised of a vessel 8 for containing therapeutic containing liposomes 19. If desired, the apparatus may include an ice bath 5 containing dry ice 17 surrounding the vessel 8. The ice bath 5 and dry ice 17 allow the liposomes to be cooled to below 0° C. A vacuum pump 1 is connected to the vessel 8 via a conduit 15 for applying a sustained negative pressure to the vessel. In the preferred embodiment, the pump 1 is capable of applying a negative pressure of at least about 700 mm Hg, and preferably a negative pressure in the range of about 700 mm Hg to about 760 mm Hg (gauge pressure). A manometer 6 is connected to the conduit 15 to allow monitoring of the negative pressure applied to the vessel 8.

In order to prevent water removed from the liposomes from entering the pump 1, a series of traps are connected to the conduit 15 to assist in collecting the water (and water vapor, all collectively referred to herein as water) drawn from the liposomes. In a preferred embodiment, two traps are utilized. The first trap is preferably comprised of a flask 7 disposed in an ice bath 4 with dry ice 17. The second trap is preferably comprised of a column 3 around which tubing 16 is helically arranged. The column 3 is connected to the conduit 15 at its top end and to one end of the tubing 16 at its bottom end. The other end of the tubing 16 is connected to the conduit 15. As shown in FIG. 14, an ice bath 2 with dry ice 17 surrounds the column 3 and tubing 16. If desired, dry ice 17 can be replaced with liquid nitrogen, liquid air or other cryogenic material. The ice baths 2 and 4 assist in collecting any water and condensing any water vapor drawn from the liposomes for collection in the traps. In preferred embodiments of the present invention the ice traps 2 and 4 are each maintained at a temperature of least about −70° C.

A stopcock 14 is disposed in the conduit 15 upstream of the vessel 8 to allow a selected gas to be introduced into the vessel 8 and into the liposomes 19 from gas bottle 18.

The apparatus may also contain a means for controlling temperature such that apparatus may be maintained at one temperature for the method of making the liposomes. For example, in the preferred embodiment, the methods of making liposomes are performed at a temperature below the boiling point of the gaseous precursor. In the preferred embodiment, a liquid gaseous precursor fills the internal space of the liposomes. Alternatively, the apparatus may be maintained at about the temperature of the liquid to gas transition temperature of the gaseous precursor such that a gas is contained in the liposomes. Further, the temperature of the apparatus may be adjusted throughout the method of making the liposomes such that the gaseous precursor begins as a liquid, however, a gas is incorporated into the resulting liposomes. In this embodiment, the temperature of the apparatus is adjusted during the method of making the liposomes such that the method begins at a temperature below the phase transition temperature and is adjusted to a temperature at about the phase transition temperature of the gaseous precursor.

Apparatus of the present invention are utilized by placing the therapeutic containing liposomes 19 into vessel 8. In a preferable embodiment, ice bath 5 with dry ice 17 is used to lower the temperature of the liposomes to below 0° C., more preferably to between about −10° C. and about −20° C., and most preferably to −10° C. With stopcocks 14 and 9 closed, vacuum pump 1 is turned on. Stopcocks 10, 11, 12 and 13 are then carefully opened to create a vacuum in vessel 8 by means of vacuum pump 1. The pressure is gauged by means of manometer 6 until negative pressure of at least about 700 mm Hg, and preferably in the range of between about 700 mm Hg and about 760 mm Hg (gauge pressure) is achieved. In preferred embodiments of the present invention vessel 7, cooled by ice bath 4 with dry ice 17, and column 3 and coil 16, cooled by ice bath 2 with dry ice 17, together or individually condense water vapor and trap water drawn from the liposomes so as to prevent such water and water vapor from entering the vacuum pump 1. In preferred embodiments of the present invention, the temperature of ice traps 2 and 4 are each maintained at a temperature of at least about −70° C. The desired negative pressure is generally maintained for at least 24 hours as water and water vapor is removed from the liposomes 19 in vessel 8 and frozen in vessels 3 and 7. Pressure within the system is monitored using manometer 6 and is generally maintained for about 24 to about 72 hours, at which time substantially all of the water has been removed from the liposomes. At this point, stopcock 10 is slowly closed and vacuum pump 1 is turned off. Stopcock 14 is then opened gradually and gas is slowly introduced into the system from gas bottle 18 through stopcock 14 via conduit 15 to instill gas into the therapeutic containing liposomes 19 in vessel 8. Preferably the gas instillation occurs slowly over a time period of at least about 4 hours, most preferably over a time period of between about 4 and about 8 hours, until the system reaches ambient pressure.

The therapeutic containing vacuum dried gas instilled liposomes and the therapeutic containing gas-filled liposomes substantially devoid of water in the interior thereof, of the present invention, have superior characteristics as therapeutic delivery vehicles.

The gas-filled liposomes prepared according to the methods of the present invention are believed to differ from the liposomes of the prior art in a number of respects, both in physical and in functional characteristics. For example, the liposomes of the invention are substantially devoid of water in the interior thereof. By definition, liposomes in the prior art have been characterized by the presence of an aqueous medium. See, e.g., *Dorland's Illustrated Medical Dictionary*, p. 946, 27th ed. (W.B. Saunders Company, Philadelphia 1988). Moreover, the present liposomes surprisingly exhibit intense echogenicity on ultrasound, are susceptible to rupture upon application of ultrasound at the peak resonant frequency of the liposomes, and possess a long storage life, characteristics of great benefit to the use of the liposomes as therapeutic delivery systems.

Thus the invention contemplates methods for the controlled delivery of therapetuic to a region of a patient comprising: (i) administering to the patient the gas-filled liposomes prepared by vacuum drying gas instillation methods and having encapsulated therein a therapeutic, and/or gas-filled liposomes substantially devoid of water in the interior thereof and having encapsulated therein a therapeutic; (ii) monitoring the liposomes using ultrasound to determine the phase transition of the gaseous precursor from liquid to gas phase and to determine the presence of the liposomes in the region; and (iii) rupturing the liposomes using ultrasound to release the therapeutic in the region.

There are various other applications for liposomes of the invention, beyond those described in detail herein. Such additional uses, for example, include such applications as hyperthermia potentiators for ultrasound and as contrast agents for ultrasonic imaging. Such additional uses and other related subject matter are described and claimed in Applicant's patent applications, U.S. Ser. No. 716,793 and U.S. Ser. No. 717,084, both of which were filed Jun. 18, 1991, the disclosures of each of which are incorporated herein by reference in their entirety.

The present invention is further described in the following examples. Examples 1 and 2 are an actual example that describes the preparation, testing and use of the gaseous precursor-filled microspheres containing a therapeutic. All of the remaining examples are prophetic. Examples 3–21 describe the preparation, testing and use of the gaseous precursor-filled microspheres containing a therapeutic. Examples 22–29 illustrate the preparation and testing of the gaseous precursor-filled liposomes prepared by shaking an aqueous solution comprising a lipid in the presence of a gas. Examples 30–36 illustrate the preparation and sizing of gaseous precursor-filled liposomes prepared by filtering and autoclaving a lipid suspension, followed by shaking the lipid solution. Examples 37 and 38 are directed to the preparation of therapeutic containing temperature activated gaseous precursor-filled liposomes. The following examples should not be construed as limiting the scope of the appended claims.

EXAMPLE 1

The methods described below demonstrate that a therapeutic such as DNA can be entrapped in gas-filled microspheres and that ultrasound can be used to release a therapeutic from a gas-filled microsphere. As shown below, liposomes entrapping water and DNA failed to release the genetic material after exposure to the same amount of ultrasonic energy. The presence of the gas within the microspheres results in much more efficient capture of the ultrasonic energy so it can be utilized for delivery of a therapeutic such as genetic material.

Gas-filled liposomes were synthesized as follows: Pure dipalmitoylphosphatidylcholine (DPPC), Avanti Polar Lipids, Alabaster, Ala., was suspended in normal saline and then extruded five times through 2 micron polycarbonate filters (Nuclepore, Costar, Pleasanton, Calif.) using an Extruder Device (Lipex Biomembranes, Vancouver, Canada) at 800 p.s.i. The resulting liposomes were then dried under reduced pressure as described in U.S. Ser. No. 716,899, filed Jun. 18, 1991, which is hereby incorporated by reference in its entirety. After thorough drying the dried liposomes were then slowly filled with nitrogen gas, as described in U.S. Ser. No. 716,899. After equilibration with ambient pressure, the resulting liposomes were suspended in saline solution (0.9% NaCl) and shaken vigorously.

The resulting gas-filled liposomes were then tested for size by Coulter Counter (Bedfordshire, England). The machine was calibrated using the calibration procedure described in the reference manual supplied with the Coulter Counter. The gas-filled liposome solution was diluted with Isoton II and placed in a glass container and was stirred at the 3 position of the Coulter Sampling Stand.

A 100 μm aperture tube was used first. With this aperture tube, 500 microliters of solution was tested at a time for each of the selected size ranges. The next size aperture tube that was used was a 30 μm aperture tube. Microspheres can be sized down to about 1 μm with this tube, in which the mean diameter of the gas-filled microspheres was detected.

50 microliters of solution were tested at a time and microspheres were counted for each of the size ranges selected. Data was collected on both the Coulter Counter model ZM and the Coulter Counter Channelyzer 256. Quasi-elastic light scattering (QEL) and light microscopy were also used. Latex beads with predetermined sizes were used to calibrate the grids in the ocular lens. These grids were calibrated for each of the magnifications of 10×, 40×, 100×, 400×, and 1000×. The gas-filled microspheres were then placed on the glass slide and viewed under different magnifications. This technique results in sizing not only of gas-filled liposomes, but also lipid particles.

The gas-filled liposomes were scanned by sonic energy using both an Acoustic Imaging Model 5200 clinical ultrasound device (Acoustic Imaging Technologies Corp., Phoenix, Ariz.) and a custom built bench top device. The bench top acoustic lab consists of a Lecroy 9410 Digital Oscilloscope (Lecroy Corporation Corporate Headquarters, Chestnut Ridge, N.Y.), a Panametrics model 5052PR Pulser/Receiver (Panametrics, Inc., Waltham, Mass.), Panametrics immersion transducers with frequencies of 2.25, 3.5, 5.0, 7.5, and 10.0 MHz (Panametrics, Inc., Waltham, Mass.), and an alignment system by Testech, Inc. (Testech, Inc., Exton, Pa.). A reference standard, a tissue mimicking phantom, was used to set the time-gain compensation (TGC) and thus the average amplitude is set in this manner. The tissue mimicking phantom is made by Radiation Measurements, Inc. (Middleton, Wis.).

As shown in Table III, the reflectivity of the gas-filled liposomes remains constant for the highest energies of pulsed sound used in these experiments over the ranges of frequencies tested. Specifically, dB reflectivity of the gas-filled liposomes remains constant despite continual scanning for 60 minutes at a power setting between 4.5–8.4 mW and an acoustic intensity of 3.25 mW/cm$^2$ (the highest power setting of pulsed sound which could be generated by the Acoustic Imaging AI5200 clinical ultrasound machine).

TABLE III

Reflectivity of Gas-Filled Microspheres

| time (minutes) | Average Amplitude (dB reflectivity) |
| --- | --- |
| 0 | −34.1 |
| 15 | −36.0 |
| 30 | −36.2 |
| 45 | −36.8 |
| 60 | −37.1 |

Solutions of gas-filled liposomes were also subjected to continuous wave ultrasound energy (Table IV) applied with a Rich-Mar Therapeutic ultrasound apparatus model RM-25 (Rich-Mar Corp., Inola, Okla.). Table IV demonstrates the power produced using continuous wave ultrasound. It was found that continuous wave energy of sound caused the gas inside the gas-filled liposomes to escape from the liposomes, thus rupturing the liposomes. It took approximately 20–30 minutes to completely destroy the gas-filled liposomes in a solution of saline at 5 watts of power and at 1 MHz. It took approximately 5 minutes to destroy the gas-filled liposomes at 10 watts and at 1 MHz. When the gas-filled liposomes were examined by light microscopy before and after application of high energy ultrasound the spherical shape of the gas-filled liposomes disappeared after exposure.

TABLE IV

Power Output and Intensity of Continuous Wave Ultrasound

| | Total ultrasonic power output P (mW) | Average Intensity at transducer face $I_{TD}$ (W/m$^2$) |
| --- | --- | --- |
| Continuous wave | 5000 | 9867 |
| Continuous wave | 10000 | 19735 |

Gas-filled microspheres were then tested for their ability to deliver DNA in a series of experiments. Liposomes were prepared from DPPC as described above except that 2 μg of DNA on a 7000 bp plasmid (pCH110: Pharmacia LKB Biotechnology, Piscataway, N.J.), in 1 cc of normal saline were added during resuspension of the dried DPPC. Gas-filled liposomes were then prepared as described above. After resuspension of the gas-filled liposomes, external unentrapped DNA was removed by affinity chromatography. The suspension of gas-filled liposomes and DNA was eluted through a column (DNA specific Sephadex®) using a peristaltic pump (Econopump, Bio-Rad Laboratories, Hercules, Calif.). The DNA affinity substrate binds to and retains the unentrapped DNA. The gas-filled microspheres elute out.

Liposomes filled with water were also prepared as described above to entrap DNA except that the drying gas instillation step was omitted. Unentrapped DNA was removed via chromatography. The gas-filled liposomes were then scanned ultrasonically as described above. The gas-filled liposomes containing DNA were similarly echogenic to pulsed ultrasound as described above. After scanning with continuous wave ultrasound as described above, the microspheres lost their echogenicity.

After treatment with continuous wave ultrasound, a propidium iodide dimer assay for free DNA (i.e., DNA external to the gas-filled liposomes) was performed and compared to control gas-filled liposomes containing DNA (i.e., not exposed to continuous wave ultrasound).

First, a 2 ml aliquot of the gas-filled microspheres was added to a test tube. 2 ml of PBS (phosphate-buffered saline) was then added, and the tube was sealed with parafilm. The test tube was then inverted several times and allowed to stand for about 5 minutes to allow separation of the microspheres. The bottom aqueous layer was then removed from the tube with a Pasteur pipette. This procedure was repeated for a total of three times to wash the microspheres.

Next, a 2 ml aliquot of DNA at 0.05 μg/ml was added to the microsphetes, the test tube was sealed and inverted to mix. After settling for about 5 minutes, the bottom aqueous layer was extracted with a Pasteur pipette. Another 2 ml aliquot of PBS was then added and the procedure repeated to wash off any unbound DNA. This procedure was repeated for a total of five times and the aqueous layers were saved for analysis.

The microspheres were then diluted with 2 ml of PBS and ultrasound was applied until there was no visual evidence of the gas-filled microspheres.

14 μl of propidium iodide dimer (POPO-3 iodide, Molecular Probes, Inc., Eugene, Oreg.), at a concentration of 2×10$^{-5}$ M in DMSO was added to each 2 ml sample after the ultrasound was applied in order to detect released DNA. As a control, 14 µl of propidium iodide was added to PBS alone, and to 0.025 µg/ml DNA in PBS.

Samples were measured for fluorescence in a Spex Fluorolog 2 Spectrophotometer using an excitation frequency of 534 nm. The emissions were recorded at 558 nm as indicated in Table V below. A percentage of the relative amount of DNA found in each sample was determined by extrapolation based upon the control PBS sample, which consisted of the propidium iodide dimer in PBS.

TABLE V

| Sample | Fluorescence (% DNA) |
| --- | --- |
| 1st wash | 58885 (45%) |
| 2nd wash | 40314 (17%) |
| 3rd wash | 33195 (7%) |
| 4th wash | 30062 (8%) |
| 5th wash | 34336 (21%) |
| Ultrasound exposed sample | 43051 (21%) |
| Control - PBS alone | 28878 |
| Control - PBS + DNA | 50563 |

The wash cycles served to remove any unbound DNA. As illustrated in Table V above, after five wash cycles, the gas-filled microspheres still contained about 21% plasmid DNA.

Gas-filled liposomes containing DNA not exposed to high energy ultrasound retained a substantial amount of their DNA internally as indicated by the absence of an appreciable increase in fluorescence from propidium iodide dimer. After exposure to continuous wave ultrasound, however, the fluorescence from propidium iodide was markedly increased indicating the high degree of release of DNA from the gas-filled microspheres caused by the continuous wave ultrasound energy. Thus, DNA was retained by the microspheres until ultrasound was applied. Upon the application of ultrasound, the entrapped DNA was released.

EXAMPLE 2

Binding of DNA by liposomes containing phosphatidic acid and gaseous precursor and gas containing liposomes. A 7 mM solution of distearoyl-sn-glycerophospate (DSPA) (Avanti Polar Lipids, Alabaster, Ala.) was suspended in normal saline and vortexed at 50° C. The material was allowed to cool to room temperature. 40 micrograms of pBR322 plasmid DNA (International Biotechnologies Inc., New Haven, Conn.) was added to the lipid solution and shaken gently. The solution was centrifuged for 10 minutes in a Beckman TJ-6 Centrifuge (Beckman, Fullerton, Calif.). The supernatant and the precipitate were assayed for DNA content using a Hoefer TKO-100 DNA Fluorometer (Hoefer, San Francisco, Calif.). This method only detects double stranded DNA as it uses an intercalating dye, Hoechst 33258 which is DNA specific. It was found that the negatively charged liposomes prepared with phosphatidic acid surprisingly bound the DNA. The above was repeated using neutral liposomes composed of DPPC as a control. No appreciable amount of DNA was detected with the DPPC liposomes. The above was repeated using gas filled liposomes prepared from an 87:8:5 mole percent of DPPC to DPPE-PEG 500 to DPPA mixture of lipids in microspheres. Again the DNA was found to bind to the gas filled liposomes containing dipalmitoylphosphatidic acid.

EXAMPLE 3

A cationic lipid, such as DOTMA is mixed as a 1:3 molar ratio with DPPC. The mixed material is dissolved in chloroform and the chloroform is removed by rotary evaporation. Water is added to the dried material and this mixture is then extruded through a 2 µm filter using an Extruder Device (Lipex Biomembranes, Inc., Vancouver, BC). Then positively charged gaseous precursor-filled liposomes are prepared according to the procedure provided in U.S. Ser. No. 717,084, filed Jun. 18, 1991, which is hereby incorporated by reference in its entirety.

The resulting dried, positively charged gaseous precursor-filled liposomes are rehydrated by adding PBS, saline or other appropriate buffered solution (such as HEPES buffer); a vortexer may be used to insure homogenous mixing. DNA is added and the mixture is again shaken. Since the DNA is attached to the surface of the cationic gaseous precursor-filled liposomes, unattached DNA may be removed with filtering or selective chromatography. Essentially all of the DNA binds up until the point where the cationic lipid is saturated. Alternatively, the DNA may be added prior to the extrusion step and the above procedure followed.

The resulting DNA coated liposomes are then dried and gaseous precursor instilled to create DNA-containing gaseous precursor-filled liposomes. The resulting liposomes are then exposed to continuous wave ultrasound and tested for rupturing by reflectivity and absorbance on ultrasound.

Sound can be used to release the genetic material whether the DNA is entrapped within or on the outside of the gaseous precursor-filled microsphere. Incorporation of the DNA on the outside of the gaseous precursor-filled microsphere may allow more space for packaging gas within the microsphere. By making an effectively larger diameter, the microsphere will generally be more effective at utilizing the sound energy to release the genetic material.

It is believed that cationic lipids binding DNA provide an advantage, for example, since once sonic energy has disrupted the membrane of the liposome, the hydrophobic groups help the DNA to integrate into cells aiding passage through cell membranes and subcellular compartments.

The cationic lipids described above also have an advantage of neutralizing the negative charge of DNA and amphipathicity. When these cationic lipids are released from the liposomes, since the lipids are amphiphilic and the cell membrane is soluble, they tend to facilitate passage of the DNA into cells as well as through subcellular compartments.

EXAMPLE 4

Gaseous precorsor-filled liposomes composed of a 1:2 molar ratio of DOTMA and DPPC are prepared and coated with DNA encoding an HLA (major histocompatibility complex) gene, HLA-B7. The DNA-coated liposomes are injected intravenously into a patient with metastatic melanoma involving the soft tissues. Upon entering the patient, the gaseous precursor undergoes a transition from a liquid to a gas. Continuous wave 1.0 megahertz ultrasound energy is applied to the soft tissues so that the HLA-B7 DNA accumulates in the tumor. It is believed that some of the tumor cells would then be transfected by the HLA-B7 gene, resulting in an immune response which may stimulate the patient's T cells to reject the tumor.

EXAMPLE 5

Antisense oligonucleotides to the Ras oncogene are entrapped within liposomes composed of polyethyleneglycol-dipalmitoylphosphatidylethanolamine. These liposomes are injected i.v. in a patient with metastatic colon cancer. Upon entering the patient, the gaseous precursor undergoes a transition from a liquid to a gas. Continuous wave 1.0 megahertz ultrasound energy is applied to the metastases.

EXAMPLE 6

Gaseous precursor-filled microspheres are made as described above using egg phosphatidylcholine and DOTMA, N-[1-(2,3-dioleoyloxy)propyl]-N,N,N-trimethylammoium chloride, to bind YAC expression vectors carrying the dystrophin gene. The microspheres are injected i.v. into a patient with Duchenne's Muscular Dystrophy (or Becker's MD). Upon entering the patient, the gaseous precursor undergoes a transition from a liquid to a gas. Continuous wave 1.0 megahertz ultrasound energy is applied to the muscle tissue of the patient and may result in an increase in muscular strength and mass.

EXAMPLE 7

The CFTR (Cystic Fibrosis transmembrane conductance regulator) gene on a YAC expression vector is entrapped within a micellar formulation of microspheres entrapping 1-fluorobutane gaseous precursor bearing cationic lipids in a 1:1 molar composition with DPPC. The microspheres are injected i.v. into a patient with Cystic Fibrosis and sonic energy is applied to the affected tissues (e.g., lungs, pancreas, etc.). The gaseous precursor undergoes a transition from a liquid to a gas, upon attaining the patient's body temperature. Patients may show a reduction in mucus accumulation in the lungs and improved functioning of the other affected organs.

EXAMPLE 8

Cationic microspheres containing DNA encoding the gene for Interleukin-2 (IL-2) are injected into a patient with metastatic renal cancer. The transition of the precursor from a liquid to a gas is monitored. A cancerous growth in the patient's abdomen is scanned with ultrasound. The backscatter from the tumor and spectral harmonic signatures of the ultrasound echoes would increase in the tumor as the microspheres accumulate in the tumor. The ultrasound power, pulse duration and pulse repetition are increased until the point at which the spectral ultrasound signature of the gas-filled microspheres disappears from the tumor. By carefully controlling the power, as detected by a hydrophone, cavitation is controlled. The treatment may result in transfection of some of the tumor cells with the gene for IL-2. T-cell lymphocytes may then respond to the cytokine and infiltrate and destroy the tumor.

EXAMPLE 9

Cationic microspheres delivering DNA encoding the gene for Tumor Necrosis Factor (TNF) are injected into a patient with metastatic renal cancer. The transition of the precursor from a liquid to a gas is monitored. A cancerous growth in the patient's abdomen is scanned with ultrasound. The backscatter from the tumor and spectral harmonic signatures of the ultrasound echoes would increase in the tumor as the microspheres accumulate in the tumor. The ultrasound power, pulse duration and pulse repetition are increased until the point at which the spectral ultrasound signature of the gas-filled microspheres disappears from the tumor. By carefully controlling the power, as detected by a hydrophone, cavitation is controlled. The treatment may result in transfection of some of the tumor cells with the gene for TNF. The tumor may then begin to produce TNF locally and massive coagulative necrosis may result.

EXAMPLE 10

Microspheres composed of dipalmitoylphosphotidylcholine and cationic lipids binding DNA are constructed with alkylated derivatives of anti-tumor monoclonal antibodies. In a patient with metastatic melanoma, microspheres coated with anti-melanoma antigen monoclonal antibody and containing Interleukin-2 are injected i.v. The patient is scanned by diagnostic ultrasound and transition of the precursor from a liquid to a gas is monitored. Tumorous deposit within the soft tissues are highlighted by the reflective, gas-filled microspheres. As these nodes are detected by diagnostic ultrasound, the power of the ultrasound is increased to 5 watts and focussed on the metastatic deposits containing the tumor. As the power is delivered, the tumors are monitored ultrasonographically. When all of the high frequency spectral signatures reflecting tumor localized microspheres disappears within a given region of tumor, the sound energy is then focussed on a new area of tumor with sonographic spectral signatures indicating microspheres.

EXAMPLE 11

Cationic gas-filled liposomes with three types of surface-bound antisense DNAs are synthesized as described above. The antisense DNAs are targeted against genes encoding c-myc, c-myb, smooth muscle growth factor, and endothelial cell growth factor. The gaseous precursor-filled liposomes are administered intra-arterially to an angioplasty site. 5 megahertz of continuous wave ultrasound is then applied to the angioplasty site, and the gas phase of the precursor is detected. It is believed that the release of the antisense RNAs upon rupture of the microspheres will cause improved endothelialization and decreased propensity to clotting.

EXAMPLE 12

Dipalmitoylphosphatidylcholine (1 gram) is suspended in 10 ml phosphate buffered saline containing the drug adriamycin, the suspension is heated to about 50° C., and then is swirled by hand in a round bottom flask for about 30 minutes. The heat source is removed, and the suspension is swirled for two additional hours, while allowing the suspension to cool to room temperature, to form drug containing liposomes.

The liposomes thus prepared are placed in a vessel in an apparatus similar to that shown in FIG. 14, cooled to about −10° C., and are then subjected to high negative vacuum pressure. The temperature of the liposomes is then raised to about 10° C. High negative vacuum pressure is maintained for about 48 hours. After about 48 hours, 1-fluorobutane gas, provided by a gaseous precursor, is gradually instilled into the chamber over a period of about 4 hours after which time the pressure is returned to ambient pressure. The resulting drug containing vacuum dried gas instilled liposomes, the gas-filled liposomes being substantially devoid of any water in the interior thereof, are then suspended in 10 cc of phosphate buffered saline and vortexed for 10 minutes, and then stored at about 4° C. for about three months.

EXAMPLE 13

To test the liposomes of Example 11 ultrasonographically, a 250 mg sample of these liposomes is suspended in 300 cc of non-degassed phosphate buffered saline. The liposomes are then scanned in vitro at varying time intervals with a 7.5 MHz transducer using an Acoustic Imaging Model 5200 scanner (Acoustic Imaging, Phoenix, Ariz.) and employing the system test software to measure dB reflectivity. The system is standardized prior to testing the liposomes with a phantom of known acoustic impedance. Good dB reflectivity of the liposomes is shown.

EXAMPLE 14

Dipalmitoylphosphatidylcholine (1 gram) and the cryoprotectant trehalose (1 gram) are suspended in 10 ml phosphate buffered saline containing the drug amphotericin-B, the suspension is heated to about 50° C., and then is swirled by hand in a round bottom flask for about 30 minutes. The heat source is removed, and the suspension is swirled for about two additional hours, while allowing the suspension to cool to room temperature, to form liposomes.

The liposomes thus prepared are then vacuum dried and gas instilled, substantially following the procedures shown in Example 11, resulting in drug containing vacuum dried gas instilled liposomes, the gas-filled liposomes being substantially devoid of any water in the interior thereof. The liposomes are then suspended in 10 cc of phosphate buffered saline and vortexed, and then stored at about 4° C. for several weeks. Prior to use, the gas-filled liposomes are extruded through a 10 μm polycarbonate filter (Nuclepore, Costar, Pleasanton, Calif.) by injection through a syringe with a filter attached to the hub.

EXAMPLE 15

To test the liposomes of Example 13 ultrasonographically, the procedures of Example 12 are substantially followed. Good dB reflectivity of the liposomes is shown.

EXAMPLE 16

Dipalmitoylphosphatidylcholine (1 gram) is suspended in 10 ml phosphate buffered saline containing the drug cytosine arabinosine, the suspension is heated to about 50° C., and then swirled by hand in a round bottom flask for about 30 minutes. The suspension is then subjected to 5 cycles of extrusion through an extruder device jacketed with a thermal barrel (Extruder Device™, Lipex Biomembranes, Vancouver, Canada), both with and without conventional freeze-thaw treatment prior to extrusion, while maintaining the temperature at about 50° C. The heat source is removed, and the suspension is swirled for about two additional hours, while allowing the suspension to cool to room temperature, to form liposomes.

The liposomes thus prepared are then vacuum dried and gas instilled, substantially following the procedures shown in Example 11, resulting in drug containing vacuum dried gas instilled liposomes, the gas-filled liposomes being substantially devoid of any water in the interior thereof. The liposomes are then suspended in 10 cc of phosphate buffered saline, and then stored at about 4° C. for several weeks.

EXAMPLE 17

To test liposomes of Example 15 ultrasonographically, the procedures of Example 12 are substantially followed. Good dB reflectivity of the liposomes is shown.

EXAMPLE 18

In order to test the stability of the drug containing liposomes of the invention, the liposomes suspension of Example 11 are passed by hand through a 10 micron polycarbonate filter in a syringe as shown in FIG. 10. After extrusion treatment, the liposomes are studied ultrasonographically, as described in Example 12. Surprisingly, even after extrusion, the liposomes of the invention substantially retain their echogenicity.

EXAMPLE 19

The liposomes of Example 11 are scanned by ultrasound using transducer frequencies varying from 3 to 7.5 mHz. The results indicate that at a higher frequency of ultrasound, the echogenicity decays more rapidly, reflecting a relatively high resonant frequency and higher energy associated with the higher frequencies.

EXAMPLE 20

A patient with cancer is given an intravenous drug containing vacuum dried gas instilled liposomes, the gas-filled liposomes being substantially devoid of any water in the interior thereof. The drug contained in the liposomes is adriamycin. As the intravenous injection is administered, the tumor is scanned ultrasonographically and via an automated software program, and the resonant frequency of the liposomes is determined. Ultrasonic energy is then focused into the tumor at the peak resonant frequency of the liposomes. The amount of ultrasonic energy is insufficient to cause any appreciable tissue heating (that is, no change in temperature greater than 2° C.), however, this energy is sufficient to cause the liposomes to pop and release the adriamycin at the tumor site. In so doing, local drug delivery is accomplished using the liposomes with ultrasound.

EXAMPLE 21

In a patient with a severe localized fungal infection, drug containing vacuum dried gas instilled liposomes, the gas-filled liposomes being substantially devoid of any water in the interior thereof, are injected intravenously and ultrasound is used in a fashion substantially similar to that described in Example 19 to accomplish local drug delivery. The drug amphotericin-B, which the liposomes contain, is effectively delivered to the site of the infection.

EXAMPLE 22

In order to prepare precursor-filled liposomes, fifty mg of 1,2-Dipalmitoyl-Sn-Glycero-3-Phosphocholine (MW: 734.05, powder, Lot No. 160pc-183) (Avanti-Polar Lipids, Alabaster, Ala.) is weighed and hydrated with 5.0 ml of saline solution (0.9% NaCl) or phosphate buffered saline (0.8% sodium chloride, 0.02% potassium chloride, 0.115% dibasic sodium phosphate and 0.02% monobasic potassium phosphate, pH adjusted to 7.4), 165 μL of 1-fluorobutane in a centrifuge tube. The hydrated suspension is then shaken on a vortex machine (Scientific Industries, Bohemia, N.Y.) for 10 minutes at an instrument setting of 6.5. A total volume of 12 ml is then noted. The saline solution decreased from 5.0 ml to about 4 ml.

The gaseous precursor-filled liposomes made via this new method were then sized by optical microscopy. It will be determined that the largest size of the liposomes range from about 50 to about 60 μm and the smallest size is about 8 μm. The average size range is from about 15 to about 20 μm.

The gaseous precursor-filled liposomes are then filtered through a 10 or 12 μm "NUCLEPORE" membrane using a Swin-Lok Filter Holder, ("NUCLEPORE" Filtration Products, Costar Corp., Cambridge, Mass.) and a 20 cc syringe (Becton Dickinson & Co., Rutherford, N.J.). The membrane is a 10 or 12 μm "NUCLEPORE" membrane (Nuclepore Filtration Products, Costar Corp., Cambridge, Mass.). The 10.0 μm filter is placed in the Swin-Lok Filter Holder and the cap tightened down securely. The liposome solution is shaken up and it transferred to the 20 cc syringe via an 18 gauge needle. Approximately 12 ml of liposome solution is placed into the syringe, and the syringe is screwed onto the Swin-Lok Filter Holder. The syringe and the filter holder assembly are inverted so that the larger of the gas-filled liposomes vesicles could rise to the top. Then the syringe is gently pushed up and the gas-filled liposomes are filtered in this manner.

The survival rate (the amount of the gas-filled liposomes that are retained after the extrusion process) of the gas-filled liposomes after the extrusion through the 10.0 $\mu$m filter is about 83–92%. Before hand extrusion, the volume of foam is about 12 ml and the volume of aqueous solution is about 4 ml. After hand extrusion, the volume of foam is about 10–11 ml and the volume of aqueous solution is about 4 ml.

The optical microscope is used again to determine the size distribution of the extruded gas-filled liposomes. It will be determined that the largest size of the liposomes range from about 25 to about 30 $\mu$m and the smallest size is about 5 $\mu$m. The average size range is from about 8 to about 15 $\mu$m.

It is found that after filtering, greater than 90% of the gas-filled liposomes are smaller than 15 $\mu$m.

EXAMPLE 23

Fifty mg of 1,2-Dipalmitoyl-sn-Glycero-3-Phosphocholine, (MW: 734.05, powder) (Avanti-Polar Lipids, Alabaster, Ala.) is weighed and placed into a centrifuge tube. The lipid is then hydrated with 5.0 ml of saline solution (0.9% NaCl). The lipid is then vortexed for 10 minutes at an instrument setting of 6.5. After vortexing, the entire solution is frozen in liquid nitrogen. Then the sample is put on the lyophilizer for freeze drying. The sample is kept on the lyophilizer for 18 hours. The dried lipid is taken off the lyophilizer and rehydrated in 5 ml of saline solution and vortexed for ten minutes at a setting of 6.5. A small sample of this solution is pipetted onto a slide and the solution is viewed under a microscope. The size of the gas-filled liposomes is then determined. It will be determined that the largest size of the liposomes is about 60 $\mu$m and the smallest size is about 20 $\mu$m. The average size ranges from about 30 to about 40 $\mu$m.

EXAMPLE 24

Fifty mg of 1,2-Dipalmitoyl-Sn-Glycero-3-Phosphocholine (MW: 734.05, powder) (Avanti-Polar Lipids, Alabaster, Ala.) was weighed and placed into a centrifuge tube. Approximately two feet of latex tubing (0.25 in. inner diameter) was wrapped around a conical centrifuge tube in a coil-like fashion. The latex tubing was then fastened down to the centrifuge tube with electrical tape. The latex tubing was then connected to a constant temperature circulation bath (VWR Scientific Model 1131). The temperature of the bath was set to 60° C. and the circulation of water was set to high speed to circulate through the tubing. A thermometer was placed in the lipid solution and found to be between 42° C. and 50° C., which is above the phase transition temperature of the lipid.

The lipid solution was vortexed for a period of 10 minutes at a vortex instrument setting of 6.5. It was noted that very little foaming of the lipid (phase transition temp.=41° C.) did not appreciably form gas-filled liposomes. Optical microscopy revealed large lipidic particles in the solution. The number of gas-filled liposomes that formed at this temperature was less than 3% of the number that form at a temperature below the phase transition temperature. The solution was allowed to sit for 15 minutes until the solution temperature equilibrated to room temperature (25° C.). The solution was then vortexed for a duration of 10 minutes. After 10 minutes, it was noted that gas-filled liposomes formed.

EXAMPLE 25

50 mg of 1,2-Dipalmitoyl-Sn-Glycero-3-Phosphocholine (MW: 734.05, powder) (Avanti-Polar Lipids, Alabaster, Ala.) was weighed and placed into a centrifuge tube. The lipid was then hydrated with 5.0 ml of 0.9% NaCl added. The aqueous lipid solution was vortexed for 10 minutes at an instrument setting of 6.5. After vortexing, the entire solution was frozen in liquid nitrogen. The entire solution was then thawed in a water bath at room temperature (25° C.). The freeze thaw procedure was then repeated eight times. The hydrated suspension was then vortexed for 10 minutes at an instrument setting of 6.5. Gas-filled liposomes were then detected as described in Example 21.

EXAMPLE 26

Two centrifuge tubes were prepared, each having 50 mg of DPPC. 1 mol % (-0.2 mg of Duponol C lot No. 2832) of sodium lauryl sulfate, an emulsifying agent, was added to one of the centrifuge tubes, and the other tube received 10 mol % (2.0 mg of Duponol C lot No. 2832). Five ml of 0.9% NaCl was added to both centrifuge tubes. Both of the tubes were frozen in liquid nitrogen and lyophilized for approximately 16 hours. Both samples were removed from the lyophilizer and 5 ml of saline was added to both of the tubes. Both of the tubes were vortexed at position 6.5 for 10 minutes.

It was determined that the largest size of the gas-filled liposomes with 1 mol % of sodium lauryl sulfate was about 75 $\mu$m and the smallest size detected was about 6 $\mu$m. The average size ranged from about 15 to about 40 $\mu$m. It was determined that the largest size of the gas-filled liposomes with 10 mol % of sodium lauryl sulfate was about 90 $\mu$m and the smallest size detected was about 6 $\mu$m. The average size ranged from about 15 to about 35 $\mu$m.

The volume of foam in the solution containing gas-filled liposomes with 1 mol % sodium lauryl sulfate was about 15 ml and the volume of aqueous solution was about 3–4 ml. The volume of foam in the solution containing gas-filled liposomes with 10 mol % sodium lauryl sulfate was also about 15 ml and the volume of aqueous solution was about 3–4 ml.

EXAMPLE 27

This example determined whether sonication could be used to create gas-filled liposomes. 50 mg of lipid, 1,2-Dipalmitoyl-Sn-Glycero-3-Phosphocholine (Avanti-Polar Lipids, Alabaster, Ala.), was weighed out and hydrated with 5 ml of 0.9% NaCl. Instead of vortexing, the aqueous solution was sonicated using a Heat Systems Sonicator Ultrasonic Processor XL (Heat Systems, Inc., Farmingdale, N.Y.) Model XL 2020. The sonicator, with a frequency of 20 KHz, was set to continuous wave, at position 4 on the knob of the sonicator. A micro tip was used to sonicate for 10 minutes. Following sonication, the solution was viewed under an optical microscope. There was evidence of gas-filled liposomes having been produced.

Next, the micro tip of the sonicator was removed and replaced with the end cap that was supplied with the sonicator. Another solution (50 mg of lipid per 5 ml of saline) was prepared and sonicated with this tip. After 10 minutes, the solution was viewed under the microscope. Again, there was no evidence of gas-filled liposomes.

EXAMPLE 28

This example determined whether a lower concentration limit of the lipid would halt the production of gas-filled liposomes. Ten mg of 1,2-Dipalmitoyl-Sn-Glycero-3-Phosphocholine (Avanti-Polar Lipids, Alabaster, Ala.) was added to 10 ml of saline solution (0.9% w:v NaCl). The lipid/saline solution was vortexed at position 6.5 for 10 minutes. The solution was viewed under an optical microscope for sizing. It was determined that the largest size of the liposomes ranged from about 30 to about 45 μm and the smallest size detected was about 7 μm. The average size ranged from about 30 to about 45 μm.

It appeared that the gas-filled liposomes were more fragile as they appeared to burst more rapidly than previously shown. Thus, it appears that concentration of the lipid is a factor in the generation and stability of gas-filled liposomes.

EXAMPLE 29

Unfiltered gas-filled liposomes were drawn into a 50 ml syringe and passed through a cascade of a "NUCLEPORE" 10 μm filter and 8 μm filter that are a minimum of 150 μm apart, as illustrated in FIGS. 11 and 12. Alternatively, for ekample, the sample may be filtered through a stack of 10 μm and 8 μm filters that are immediately adjacent to each other. Gas-filled liposomes were passed through the filters at such a pressure whereby the flow rate was 2.0 ml min$^{-1}$. The subsequently filtered gas-filled liposomes were then measured for yield of gas-filled lipid microspheres which resulted in a volume of 80–90% of the unfiltered volume.

The resulting gas-filled liposomes were sized by four different methods to determine their size and distribution. Sizing was performed on a Particle Sizing Systems Model 770 Optical Sizing unit, a Zeiss Axiplan optical microscope interfaced to image processing software manufactured by Universal Imaging, and a Coulter Counter (Coulter Electronics Limited, Luton, Beds., England). As can be seen in FIGS. 15 and 16, the size of the gas-filled liposomes were more uniformly distributed around 8–10 μm as compared to the unfiltered gas-filled liposomes. Thus, it can be seen that the filtered gas-filled liposomes are of much more uniform size.

EXAMPLE 30

250 mg DPPC (dipalmitoylphosphatidylcholine) and 10 ml of 0.9% NaCl were added to a 50 ml Falcon centrifuge tube (Becton-Dickinson, Lincoln Park, N.J.) and maintained at an ambient temperature (approx. 20° C.). The suspension was then extruded through a 1 μm "NUCLEPORE" (Costar, Pleasanton, Calif.) polycarbonate membrane under nitrogen pressure. The resultant suspension was sized on a Particle Sizing Systems (Santa Barbara, Calif.) Model 370 laser light scattering sizer. All lipid particles were 1 μm or smaller in mean outside diameter.

In addition, the same amount of DPPC suspension was passed five times through a Microfluidics™ (Microfluidics Corporation, Newton, Mass.) microfluidizer at 18,000 p.s.i. The suspension, which became less murky, was sized on a Particle Sizing Systems (Santa Barbara, Calif.) Sub Micron Particle Sizer Model 370 laser light scattering sizer where it was found that the size was uniformly less than 1 μm. The particle size of microfluidized suspensions is known to remain stable up to six months.

EXAMPLE 31

100 mg DSPC (distearoylphosphatidylcholine) and 10 ml of 0.9% NaCl were added to a 50 ml Falcon centrifuge tube (Becton-Dickinson, Lincoln Park, N.J.). The suspension was then extruded through a 1 μm "NUCLEPORE" (Costar, Pleasanton, Calif.) polycarbonate membrane under nitrogen pressure at 300–800 p.s.i. The resultant suspension was sized on a Particle Sizing Systems (Santa Barbara, Calif.) Sub Micron Particle Sizer Model 370 laser light scattering sizer. It was found that all particles were 1 μm or smaller in size.

In addition, the same amount of DPPC suspension was passed five times through a Microfluidics™ (Microfluidics Corporation, Newton, Mass.), microfluidizer at 18,000 p.s.i. The resultant suspension, which was less murky, was sized on a Sub Micron Particle Sizer Systems Model 370 laser light scattering sizer and it was found that the size was uniformly less than 1 μm.

EXAMPLE 32

The previously sized suspensions of DPPC and DSPC of Examples 29 and 30 were subjected to autoclaving for twenty minutes on a Barnstead Model C57835 autoclave (Barnstead/Thermolyne, Dubuque, Iowa). After equilibration to room temperature (approx. 20° C.), the sterile suspension was used for gas instillation.

EXAMPLE 33

10 ml of a solution of 1,2-dipalmitoylphosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the liquid was vortexed on a VWR Genie-2 (120 V, 0.5 amp, 60 Hz.) (Scientific Industries, Inc., Bohemia, N.Y.) for 10 minutes or until a time that the total volume of gas-filled liposomes was at least double or triple the volume of the original aqueous lipid solution. The solution at the bottom of the tube was almost totally devoid of anhydrous particulate lipid, and a large volume of foam containing gas-filled liposomes resulted. Thus, prior autoclaving does not affect the ability of the lipid suspension to form gas-filled liposomes. Autoclaving does not change the size of the liposomes, and it does not decrease the ability of the lipid suspensions to form gas-filled liposomes.

EXAMPLE 34

10 ml of a solution of 1,2-dipalmitoylphosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was then placed upright on a VWR Scientific Orbital shaker (VWR Scientific, Cerritos, Calif.) and shaken at 300 r.p.m. for 30 minutes. The resultant agitation on the shaker table resulted in the production of gas-filled liposomes.

EXAMPLE 35

10 ml of a solution of 1,2-dipalmitoylphosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was immobilized inside a 1 gallon empty household paint container and subsequently placed in a mechanical paint mixer employing a gyrating motion for 15 minutes. After vigorous mixing, the centrifuge tube was removed, and it was noted that gas-filled liposomes had formed.

EXAMPLE 36

10 ml of a solution of 1,2-dipalmitoylphosphatidylcholine at 25 mg/ml in 0.9% NaCl, which had previously been extruded through a 1 $\mu$m nuclepore filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was shaken forcefully by hand for ten minutes. Upon ceasing agitation, gas-filled liposomes were formed.

EXAMPLE 37

Gas-filled liposomes were produced from DPPC as described in Example 32. The resultant unfiltered liposomes were drawn into a 50 ml syringe and passed through a cascade filter system consisting of a "NUCLEPORE" (Costar, Pleasanton, Calif.) 10 $\mu$m filter followed by an 8 $\mu$m filter spaced a minimum of 150 $\mu$m apart. In addition, on a separate sample, a stacked 10 $\mu$m and 8 $\mu$m filtration assembly was used, with the two filters adjacent to one another. Gas-filled liposomes were passed through the filters at a pressure such that they were filtered a rate of 2.0 ml/min. The filtered gas-filled liposomes yielded a volume of 80–90% of the unfiltered volume.

The resultant gas-filled liposomes were sized by four different methods to determine their size distribution. Sizing was performed on a Particle Sizing Systems (Santa Barbara, Calif.) Model 770 Optical Sizing unit, and a Zeiss (Oberkochen, Germany) Axioplan optical microscope interfaced to image processing software (Universal Imaging, West Chester, Pa.) and a Coulter Counter (Coulter Electronics Limited, Luton, Beds., England). As illustrated in FIG. 18, the size of the gas-filled liposomes was more uniformly distributed around 8–10 $\mu$m as compared to the unfiltered gas-filled liposomes.

EXAMPLE 38

This example involves the production of a microsphere which will be formed in the bloodstream of a human being, by way of example, a gaseous microsphere of 10 microns diameter where the typical temperature would be 37° C. or 310° K. At a pressure of 1 atmosphere $7.54 \times 10^{-17}$ moles of gaseous precursor would be required to fill the volume of a 10 micron diameter microsphere.

1-fluorobutane, which possesses a molecular weight of 76.11, a boiling point of 32.5° C., and a density of 6.7789 grams mL$^{-1}$ at 20° C., may be used as the gaseous precursor. $5.74 \times 10^{-15}$ grams of this precursor will be required to fill a 10 micron diameter microsphere. The density of 1-fluorobutane will require $8.47 \times 10^{-16}$ mLs of liquid precursor to form a microsphere with an upper limit of 10 microns.

An emulsion of lipid droplets with a radius of 0.0272 microns or a corresponding diameter of 0.0544 microns are needed to make a gaseous precursor microsphere whose upper limit would fulfill the criteria of forming a 10 micron microsphere. An emulsion of this particular size could be easily achieved by the use of an appropriately sized filter. In addition, as can be seen by the size of the filter necessary to form gaseous precursor droplets of defined size, the size of the filter would also suffice to remove any possible bacterial contaminants and, hence, can be used as a sterile filtration as well.

In the case of the 1-fluorobutane droplet of liquid precursor necessary to produce a microsphere of 10 $\mu$m diameter, a multilamellar stabilizing liposomal coating would increase the effective particle or droplet size from about 0.0544 $\mu$m to about 0.1344 $\mu$m. This size droplet will easily pass through a 0.22 μm filter. After in vivo phase transition, the gaseous precursor-filled microsphere, in multilamellar form, may change to a unilamellar or oligolamellar coating. The effect on final gas-filled microsphere size due to the bilayer coating may now be minimal. The lipid bilayers may be selected such that the phase transition from the gel state to the liquid-crystalline state of the lipid matches the boiling point of the gaseous precursor. In so doing, the lipidic coating will more readily facilitate microsphere expansion.

EXAMPLE 39

The gaseous precursor, 1-fluorobutane, can be entrapped in liposomes and as the temperature is raised, liposomally entrapped fluorobutane gas results. The gaseous precursor, 1-fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents surprisingly stable gas microspheres result.

EXAMPLE 40

An experiment identical to Example 39 may be performed with the sequential replacement of perfluoropentane by sulfur hexafluoride, hexafluoropropylene, bromochlorofluoromethane, octafluoropropane, 1,1 dichloro, fluoro ethane, hexa fluoroethane, hexafluoro-2-butyne, perfluoropentane, perfluorobutane, octafluoro-2-butene or hexafluorobuta-1,3-diene or octafluorocyclopentene, all with the production of gaseous precursor filled liposomes.

Various modifications of the invention in addition to those shown and described herein will be apparent to those skilled in the art from the foregoing description. Such modifications are also intended to fall within the scope of the appended claims.

What is claimed is:

1. A method for the controlled delivery of therapeutic compounds to a region of a patient comprising:

(i) administering to the patient temperature activated gaseous precursor-filled microspheres comprising a therapeutic compound;

(ii) monitoring the microspheres using energy to determine the liquid to gas phase transition and the presence of the microspheres in the region; and (iii) rupturing the microspheres using energy to release the therapeutic compound in the region.

2. The method of claim 1 wherein said energy is selected from the group consisting of ultrasound, microwave radiofrequency energy, magnetic induction oscillating energy, and light energy.

3. The method of claim 2 wherein said ultrasound energy comprises continuous wave ultrasound energy.

4. The method of claim 2 wherein said ultrasound energy is selected from the group consisting of amplitude and frequency modulated pulses.

5. The method of claim 2 wherein said ultrasound energy is applied as a pulse selected from the group consisting of a PRICH pulse and a CHIRP pulse.

6. The method of claim 2 wherein said light energy is selected from the group consisting of a laser and infrared energy.

7. The method of claim 1 wherein said energy is applied externally to the patient.

8. The method of claim 1 wherein said energy is applied endoscopically to the patient.

9. The method of claim 1 wherein the microspheres are administered intravenously.

10. The method of claim 1 wherein the microspheres are comprised of a lipid selected from the group consisting of fatty acids; lysolipids; phosphatidylcholine; dioleoylphosphatidylcholine; dimyristoylphosphatidylcholine; dipentadecanoylphosphatidyl-choline; dilauroylphosphatidylcholine; dioleoylphosphatidyl-choline; dipalmitoylphosphatidylcholine; distearoylphosphatidylcholine; phosphatidylethanolamine; dioleoylphosphatidylethanolamine; phosphatidylserine; phosphatidylglycerol; phosphatidylinositol; sphingolipids; sphingomyelin; glycolipids; ganglioside GM1; ganglioside GM2; glucolipids; sulfatides; glycosphingolipids; phosphatidic acid; palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol, cholesterol sulfate; cholesterol hemisuccinate; tocopherol hemisuccinate, lipids with ether and ester-linked fatty acids, polymerized lipids, diacetyl phosphate, stearylamine, cardiolipin, phospholipids with short chain fatty acids of 6–8 carbons in length, synthetic phospholipids with asymmetric acyl chains, 6-(5-cholesten-3β-yloxy)-1-thio-β-D-galactopyranoside, digalactosyldiglyceride, 6-(5-cholesten-3β-yloxy)hexyl-6-amino-6-deoxy-1-thio-β-D-galactopyranoside, 6-(5-cholesten-3β-yloxy)hexyl-6-amino-6-deoxyl-1-thio-α-D-mannopyranoside, 12-(((7'-diethylaminocoumarin-3-yl) carbonyl)methylamino)-octadecanoic acid; N-[12-(((7'-diethylaminocoumarin-3-yl)carbonyl)methylamino) octadecanoyl]-2-aminopalmitic acid; cholesteryl)4'-trimethyl-ammonio)butanoate; N-succinyldioleoylphosphatidylethanol-amine; 1,2-dioleoyl-sn-glycerol;1,2-dipalmitoyl-sn-3-succinylglycerol; 1,3-dipalmitoyl-2-succinylglycerol;1-hexadecyl-2-palmitoylglycerophosphoethanolamine; palmitoylhomocysteine; and/or combinations thereof; lauryltrimethylammonium bromide, cetyltrimethylammonium bromide, myristyltrimethylammonium bromide, alkyldimethylbenzylammonium chloride, benzyldimethyldodecylammonium bromide, benzyldimethylhexadecylammonium bromide, benzyldimethyltetradecylammonium bromide, cetyldimethylethylammonium bromide, or cetylpyridinium bromide; pentafluoro octadecyl iodide, perfluorooctylbromide, perfluorodecalin, perfluorododecalin, perfluorooctyliodide, perfluorotripropylamine, and perfluorotributylamine.

11. The method of claim 1 wherein the microspheres are filled with a gas selected from the group consisting of fluorine, perfluoromethane, perfluoroethane, perfluoropropane, perfluorobutane, perfluoropentane, perfluorohexane, sulfur hexafluoride, hexafluoropropylene, bromochlorofluoromethane, octafluoropropane, 1,1 dichloro, fluoro ethane, hexa fluoroethane, hexafluoro-2-butyne, perfluoropentane, perfluorobutane, octafluoro-2-butene, hexafluorobuta-1,3-diene, octafluorocyclopentene, hexafluoroacetone, isopropyl acetylene, allene, tetrafluoro allene, boron trifluoride, 1,2-butadiene, 1,3-butadiene, 1,2, 3-trichloro,2-fluoro-1,3-butadiene, 2-methyl,1,3-butadiene, hexafluoro-1,3-butadiene, butadiene, 1-fluorobutane, 2-methyl-butane, decafluoro butane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1, 1,1,4,4,4-hexafluoro-butyne, 3-methyl-1-butyne, perfluoro-2-butyne, 2-bromo-butyraldehyde, carbonyl sulfide, crotononitrile, cyclobutane, methyl-cyclobutane, octafluoro-cyclobutane, perfluoro-cyclobutene, 3-chloro-cyclopentene, cyclopropane, 1, 2-dimethyl-cyclopropane, 1,1-dimethyl-cyclopropane, 1,2-dimethyl cyclopropane, ethyl cyclopropane, methyl cyclopropane, diacetylene, 3-ethyl-3-methyl diaziridine, 1,1,1-trifluoro-diazoethane, dimethyl amine, hexafluoro-dimethyl amine, dimethylethylamine, bis-(Dimethyl phosphine)amine, 2,3-dimethyl-2-norbornane, perfluoro-dimethylamine, dimethyloxonium chloride, 1,3-dioxolane-2-one, 4-methyl, 1,1,1,2-tetrafluoro ethane, 1,1,1 trifluoroethane, 1,1,2,2-tetrafluoroethane, 1,1,2-trichloro-1,2,2-trifluoroethane, 1,1 dichloro ethane, 1,1-dichloro-1,2,2,2-tetrafluoro ethane, 1,2-difluoro ethane, 1-chloro-1,1,2,2,2-pentafluoro ethane, 2-chloro,1,1-difluoroethane, 1-chloro-1,1,2,2-tetrafluoro ethane, 2-chloro, 1,1-difluoro ethane, chloroethane, chloropentafluoro ethane, dichlorotrifluoroethane, fluoro-ethane, hexafluoro-ethane, nitro-pentafluoro ethane, nitroso-pentafluoro ethane, perfluoro ethane, perfluoro ethylamine, ethyl vinyl ether, 1,1-dichloro ethylene, 1,1-dichloro-1,2-difluoro ethylene, 1,2-difluoro ethylene, Methane, Methane-sulfonyl chloride-trifluoro, Methane-sulfonyl fluoride-trifluoro, Methane-(pentafluorothio)trifluoro, Methane-bromo difluoro nitroso, Methane-bromo fluoro, Methane-bromo chloro-fluoro, Methane-bromo-trifluoro, Methane-chloro difluoro nitro, Methane-chloro dinitro, Methane-chloro fluoro, Methane-chloro trifluoro, Methane-chloro-difluoro, Methane-dibromo difluoro, Methane-dichloro difluoro, Methane-dichloro-fluoro, Methane-difluoro, Methane-difluoro-iodo, Methane-disilano, Methane-fluoro, Methane-iodo-trifluoro, Methane-nitro-trifluoro, Methane-nitroso-trifluoro, Methane-tetrafluoro, Methane-trichlorofluoro, Methane-trifluoro, Methanesulfenylchloride-trifluoro, 2-Methyl butane, Methyl ether, Methyl isopropyl ether, Methyl lactate, Methyl nitrite, Methyl sulfide, Methyl vinyl ether, Neon, Neopentane, Nitrogen, Nitrous oxide, 1,2,3-Nonadecane tricarboxylic acid-2-hydroxytrimethylester, 1-Nonene-3-yne, oxygen, 1,4-Pentadiene, n-Pentane, Pentane-perfluoro, 2-Pentanone-4-amino-4-methyl, 1-Pentene, 2-Pentene {cis}, 2-Pentene {trans}, 1-Pentene-3-bromo, 1-Pentene-perfluoro, Phthalic acid-tetrachloro, Piperidine-2,3,6-trimethyl, Propane, Propane-1,1,1,2,2,3-hexafluoro, Propane-1,2-epoxy, Propane-2,2 difluoro, Propane-2-amino, Propane-2-chloro, Propane-heptafluoro-1-nitro, Propane-heptafluoro-1-nitroso, Propane-perfluoro, Propene, Propyl-1,1,1,2,3,3-hexafluoro-2,3 dichloro, Propylene-1-chloro, Propylene-chloro-{trans}, Propylene-2- chloro, Propylene-3-fluoro, Propylene-perfluoro, Propyne, Propyne-3,3,3-trifluoro, Styrene-3-fluoro, Sulfur hexafluoride, Sulfur (di)-decafluoro (S2F10), Toluene-2,4-diamino, Trifluoroacetonitrile, Trifluoromethyl peroxide, Trifluoromethyl sulfide, Tungsten hexafluoride, Vinyl acetylene, Vinyl ether, and Xenon.

12. The method of claim 1 wherein the microspheres are filled with perfluorobutane.

13. The method of claim 1 wherein said microspheres comprise a lipid bearing a covalently bound polymer.

14. The method of claim 13 wherein said polymer is between 400 and 200,000 molecular weight.

15. The method of claim 13 wherein said polymer is between 1,000 and 20,000 molecular weight.

16. The method of claim 13 wherein said polymer is between 2,000 and 8,000 molecular weight.

17. The method of claim 13 wherein said lipid bearing a covalently bound polymer comprises compounds of the formula XCHY—(CH$_2$)n-O—(CH$_2$)n-YCHX wherein X is an alcohol group, Y is OH or an alkyl group and n is 0 to 10,000.

18. The method of claim 13 wherein said polymer is selected from the group consisting of polyethyleneglycol, polyvinylpyrrolidone, polyvinylalcohol and polypropyleneglycol.

19. The method of claim 13 wherein said polymer is polyethyleneglycol.

20. The method of claim 13 wherein said lipid comprises from about 1 mole % to about 20 mole %.

21. The method of claim 1 comprising a mixed lipid solvent system of saline, glycerol and propylene glycol.

22. The method of claim 1 comprising negatively charged lipid.

23. The method of claim 22 wherein said negatively charged lipid comprises phosphatidic acid and phosphatidylglycerol.

24. The method of claim 22 wherein said negatively charged lipid comprises phosphatidic acid.

25. The method of claim 22 wherein said negatively charged lipid comprises about 1 mole % to about 20 mole %.

26. The method of claim 1 wherein said microspheres are activated in vivo.

27. The method of claim 1 wherein said microspheres are stored suspended in an aqueous medium.

28. The method of claim 1 wherein the microspheres have a reflectivity of between about 2 dB and about 20 dB.

29. The method of claim 1 wherein the microspheres comprise gas-filled liposomes substantially devoid of water in the interior thereof and having encapsulated therein a therapeutic compound.

30. The method of claim 1 wherein the microspheres comprise gaseous precursor-filled liposomes prepared by a gel state shaking gaseous precursor instillation method.

31. The method of claim 1 wherein said microspheres are administered via a nebulizer.

32. The method of claim 31 wherein said microspheres are targeted to the lung.

33. The method of claim 32 wherein said therapeutic is antisense ras/p53.

34. A method for the delivery of therapeutic compounds to a patient comprising administering to the lung of the patient liquid temperature activated gaseous precursor filled microspheres comprising a therapeutic compound.

35. The method of claim 34 wherein said microspheres are administered via a nebulizer.

36. The method of claim 35 wherein the gaseous precursor is a perfluorocarbon.

37. The method of claim 36 wherein the perfluorocarbon is selected from the group consisting of perfluoromethane, perfluoroethane, perfluoropropane, perfluorobutane, perfluoropentane and perfluorohexane.

38. The method of claim 37 wherein the perfluorocarbon is perfluoropentane.

39. The method of claim 34 wherein the gaseous precursor is a perfluorocarbon.

40. The method of claim 39 wherein the perfluorocarbon is selected from the group consisting of perfluoromethane, perfluoroethane, perfluoropropane, perfluorobutane, perfluoropentane and perfluorohexane.

41. The method of claim 40 wherein the perfluorocarbon is perfluoropentane.

42. The method of claim 34 further comprising monitoring the microspheres using ultrasound to determine the presence of the microspheres in the lung of the patient.

43. The method of claim 34 further comprising rupturing the microspheres using ultrasound to release the therapeutic compound.

44. A method for delivery of therapeutic compounds to a patient comprising administering to the lung of the patient a liquid temperature activated gaseous precursor filled emulsion comprising a therapeutic compound.

45. The method of claim 44 wherein said emulsion is administered via a nebulizer.

46. The method of claim 45 wherein the gaseous precursor is a perfluorocarbon.

47. The method of claim 46 wherein the perfluorocarbon is selected from the group consisting of perfluoromethane, perfluoroethane, perfluoropropane, perfluorobutane, perfluoropentane and perfluorohexane.

48. The method of claim 47 wherein the perfluorocarbon is perfluoropentane.

49. The method of claim 44 wherein the gaseous precursor is a perfluorocarbon.

50. The method of claim 49 wherein the perfluorocarbon is selected from the group consisting of perfluoromethane, perfluoroethane, perfluoropropane, perfluorobutane, perfluoropentane and perfluorohexane.

51. The method of claim 50 wherein the perfluorocarbon is perfluoropentane.

52. The method of claim 44 further comprising monitoring the emulsion using ultrasound to determine the presence of the emulsion in the lung of the patient.

53. The method for the delivery of therapeutic compounds to a patient comprising administering to the lung of the patient liquid temperature activated gaseous precursor filled vesicles comprising a therapeutic compound.

54. The method of claim 53 wherein the vesicles are lipid vesicles.

55. The method of claim 53 wherein the vesicles are administered via a nebulizer.

56. The method of claim 55 wherein the gaseous precursor is a perfluorocarbon.

57. The method of claim 56 wherein the perfluorocarbon is selected from the group consisting of perfluoromethane, perfluoroethane, perfluoropropane, perfluorobutane, perfluoropentane and perfluorohexane.

58. The method of claim 57 wherein the perfluorocarbon is perfluoropentane.

59. The method of claim 53 wherein the gaseous precursor is a perfluorocarbon.

60. The method of claim 59 wherein the perfluorocarbon is selected from the group consisting of perfluoromethane, perfluoroethane, perfluoropropane, perfluorobutane, perfluoropentane and perfluorohexane.

61. The method of claim 60 wherein the perfluorocarbon is perfluoropentane.

62. The method of claim 53 further comprising monitoring the vesicles using ultrasound to determine the presence of the vesicles in the lung of the patient.

63. The method of claim 53 further comprising rupturing the vesicles using ultrasound to release the therapeutic compound.

64. The method of claim 1 wherein said microspheres comprise a lipid-containing monolayer.

65. The method of claim 64 wherein said microspheres comprise a polymerized lipid.

66. The method of claim 64 wherein said microspheres further comprise polyethylene glycol.

67. A method for the controlled delivery of a drug to an internal bodily region of a patient comprising:
(a) administering to the patient a drug delivery system comprising a gas-filled lipid containing microsphere prepared by a vacuum drying gas instillation method having encapsulated therein a drug, wherein said gas is provided by a gaseous precursor;
(b) monitoring the microsphere using ultrasound to determine the phase transition of the gaseous precursor from a liquid to a gas and to determine the presence of said microsphere in the region; and
(c) rupturing the microsphere using ultrasound to release the drug in the region.

68. The method according to claim 67 wherein the drug is delivered in the area of the patient's left heart.

69. The method of claim 68 wherein said drug delivery system is activated by energy delivered to the target site.

70. The method of claim 67 wherein said gaseous precursor is a perfluorocarbon.

71. The method of claim 67 wherein said gaseous precursor is selected from the group consisting of nitrogen, perfluoromethane, perfluoroethane, perfluoropropane, perfluorobutane, perfluoropentane, and perfluorohexane.

72. The method of claim 71 wherein said gaseous precursor is a combination of nitrogen and perfluorohexane.

73. The method of claim 71 wherein said gaseous precursor is a combination of nitrogen and perfluoropropane.

74. The method of claim 67 wherein said microspheres have been rehydrated from lyophilized microspheres.

75. A method of administering drugs to ischemic and diseased tissues comprising delivering to the target site of a patient a drug delivery system comprising gas-filled microspheres having encapsulated therein one or more drugs, wherein said gas is provided by a temperature activated gaseous precursor having an activation temperature of about body temperature.

76. The method of claim 75 wherein said microspheres comprise a protein.

77. The method of claim 76 wherein said gas or gaseous precursor is a prefluorocarbon.

78. The method of claim 77 wherein said perfluorocarbon is selected from the group consisting of perfluoromethane, perfluoroethane, perfluoropropane, perfluorobutane, perfluoropentane, and perfluorohexane.

79. The method of claim 78 wherein said perfluorocarbon is perfluoropropane.

80. The method of claim 75 wherein said microspheres have been rehydrated from lyophilized microspheres.

81. The method of claim 75 wherein said microspheres comprise a lipid-containing monolayer.

82. The method of claim 81 wherein said microspheres comprise a polymerized lipid.

83. The method of claim 81 wherein said microspheres further comprise polyethylene glycol.

84. The method of claim 67 wherein said liposomes comprise a monolayer.

85. The method of claim 84 wherein said liposomes comprise a polymerized lipid.

86. The method of claim 84 wherein said liposomes comprise polyethylene glycol.

87. The method of claim 64, 84, or 81 wherein said monolayer comprises a phospholipid.

88. The method of claim 87 wherein said gaseous precursor is selected from the group consisting of perfluoropropane, perfluorobutane, perfluoropentane, perfluorohexane and sulfur hexafluoride.

89. The method of claim 64, 84, or 81 wherein said monolayer comprises a phospholipid and said gaseous precursor is perfluoropentane.

90. The method of claim 64, 84, or 81 wherein said monolayer comprises a phospholipid and said gaseous precursor is sulfur hexafluoride.

91. The method of claim 64, 84, or 81 wherein said monolayer comprises a phospholipid and said gaseous precursor is perfluoropropane.

92. The method of claim 1 wherein said microspheres comprise a protein.

93. The method of claim 92 wherein said gaseous precursor is a perfluorocarbon.

94. The method of claim 93 wherein said perfluorocarbon is selected from the group consisting of perfluoromethane, perfluoroethane, perfluoropropane, perfluorobutane, perfluoropentane, and perfluorohexane.

95. The method of claim 94 wherein said perfluorocarbon is perfluoropropane.

96. The method of claim 1 wherein said microspheres have been rehydrated from lyophilized microspheres.

* * * * *